(12) United States Patent
Barnhill et al.

(10) Patent No.: US 6,789,069 B1
(45) Date of Patent: Sep. 7, 2004

(54) METHOD FOR ENHANCING KNOWLEDGE DISCOVERED FROM BIOLOGICAL DATA USING A LEARNING MACHINE

(75) Inventors: Stephen Barnhill, Savannah, GA (US); Isabelle Guyon, Berkeley, CA (US); Jason Weston, New York, NY (US)

(73) Assignee: BIOwulf Technologies LLC, Savannah, GA (US)

( * ) Notice: Subject to any disclaimer, the term of this patent is extended or adjusted under 35 U.S.C. 154(b) by 348 days.

(21) Appl. No.: 09/633,850

(22) Filed: Aug. 7, 2000

Related U.S. Application Data

(63) Continuation-in-part of application No. 09/578,011, filed on May 24, 2000, now Pat. No. 6,658,395, which is a continuation-in-part of application No. 09/568,301, filed on May 9, 2000, now Pat. No. 6,427,141, which is a continuation of application No. 09/303,387, filed on May 1, 1999, now Pat. No. 6,128,608, which is a continuation of application No. 09/305,345, filed on May 1, 1999, now Pat. No. 6,157,921, which is a continuation of application No. 09/303,386, filed on May 1, 1999, now abandoned, which is a continuation of application No. 09/303,389, filed on May 1, 1999, now abandoned.

(60) Provisional application No. 60/191,219, filed on Mar. 22, 2000, now Pat. No. 6,658,395, provisional application No. 60/184,596, filed on Feb. 24, 2000, provisional application No. 60/168,703, filed on Dec. 2, 1999, provisional application No. 60/161,806, filed on Oct. 27, 1999, provisional application No. 60/135,715, filed on May 25, 1999, and provisional application No. 60/083,961, filed on May 1, 1998.

(51) Int. Cl.$^7$ ............................ G06F 15/18; G06F 17/00
(52) U.S. Cl. ........................................... 706/12; 706/45
(58) Field of Search ...................................... 706/12, 45

(56) References Cited

U.S. PATENT DOCUMENTS

| | | | |
|---|---|---|---|
| 4,881,178 A | | 11/1989 | Holland et al. ............... 706/12 |
| 5,138,694 A | | 8/1992 | Hamilton et al. ............. 706/52 |
| 5,627,945 A | * | 5/1997 | Cohen ........................... 706/56 |
| 5,649,068 A | | 7/1997 | Boser et al. ................... 706/12 |
| 5,809,144 A | | 9/1998 | Sirbu et al. .................... 705/26 |
| 5,950,146 A | | 9/1999 | Vapnik ......................... 702/153 |
| 6,112,195 A | * | 8/2000 | Burges .......................... 706/20 |
| 6,128,608 A | | 10/2000 | Barnhill ........................ 706/16 |
| 6,134,344 A | * | 10/2000 | Burges ......................... 382/155 |
| 6,157,921 A | * | 12/2000 | Barnhill ........................ 706/16 |
| 6,427,141 B1 | * | 7/2002 | Barnhill ........................ 706/16 |

OTHER PUBLICATIONS

Yan, Yonghong et al., "Experiments for an approach to language identification with conversational telephone speech" 1995 IEEE International Conference, pp. 789–792.

Osuna, Edgar et al., "An Improved Training Algorithm for Support Vector Machines", 1997 IEEE International Conference, pp. 276–285.

Osuna, Edgar et al., "Training Support Vector Machines: an Application to Face Detection", 1997 IEEE Conference, pp. 130–136.

(List continued on next page.)

*Primary Examiner*—George B. Davis
(74) *Attorney, Agent, or Firm*—Kilpatrick Stockton LLP

(57) ABSTRACT

A learning machine is used to extract useful information from vast quantities of biological data. The method includes pre-processing of training data and test data to add dimensionality or to identify missing or erroneous data points. The training data is used to train the learning machine after which the success of the training is tested using the test data. The test output is pre-processed to determine whether the knowledge discovered from the pre-processed test data set is desirable. After the training has been confirmed, live biological data can be pre-processed then input into the trained learning machine for extraction of useful information. In the preferred embodiment, the learning machine is one or more support vector machines.

51 Claims, 33 Drawing Sheets

OTHER PUBLICATIONS

Osuna, Edgar et al., "Support Vector Machines: Training and Applications", Massachusetts Institute of Technology, Artificial Intelligence Laboratory and Center for Biological and Computational Learning Department of Brain and Cognitive Sciences, Copyright 1996, Published Mar. 1997, pp. 1–41.

Pontil, Massimiliano et al., "Properties of Support Vector Machines", Massachusetts Institute of Technology, Artificial Intelligence Laboratory and Center for Biological and Computational Learning Department of Brain and Cognitive Sciences, Copyright 1999, Published Aug. 1997, 1994, pp. 1–6.

Sung, Kah–Kay et al., "Example–based Learning for View–based Human Face Detection", Massachusetts Institute of Technology, Artificial Intelligence Laboratory and Center for Biological and Computational Learning Department of Brain and Cognitive Sciences, Copyright 1994, Published Dec. 1994, pp. 1–16.

Alpaydin, Ethem, "Multiple Neural Networks and Weighted Voting", 1992 IEEE, Department of Computer Engineering, Bogazici University, pp. 29–32.

Kim, Jongryeol et al., "A Systematic Approach to Classifier Selection on Combining Multiple Classifiers for Handwritten Digit Recognition", 1997 IEEE, Soongsil University, pp. 459–461.

Kato, Yoshinaga et al., "An Application of SVM: Alphanumeric Character Recognition", IEEE International Joint Conference on Neural Networks, Jun. 1989 (Abstract only).

Scholkopf, Bernhard et al., "Comparing Support Vector Machines with Gaussian Kernels to Radial Basis Function Classifiers", IEEE Transactions on Signal Processing, vol. 45, No. 11, Nov. 1997, pp. 2758–2765.

de Chazal, P et al., "Improving ECG Diagnostic Classification by Combining Multiple Neural Networks", 1997 IEEE, Computers in Cardiology, vol. 24, 1997, pp. 473–476.

U.S. patent application Ser. No. 09/303,389 filed May 1, 1999; Inventor: Stephen Barnhill; entitled: "Optimal Categorization of a Continuous Variable".

U.S. patent application Ser. No. 09/305,345 filed May 1, 1999; Inventor: Stephen Barnhill; entitled: "Enhancing Knowledge Discovery Using Support Vector Machines in a Distributed Network Environment".

U.S. patent application Ser. No. 09/303,386 filed Nov. 17, 2000; Inventor: Stephen Barnhill entitled: "Pre–Processing and Post Processing for Enhancing Knowledge Discovery Using Support Vector Machines".

U.S. patent application Ser. No. 09/568,301 filed May 9, 2000; Inventor: Stephen Barnhill; entitled: Enhancing Knowledge Discovery Using Multiple Support Vector Machines.

U.S. patent application Ser. No. 09/578,011 filed May 24, 2000; Inventor: Stephen Barnhill; entitled: "Enhancing Knowledge Discovery from Multiple Data Sets Using Multiple Support Vector".

Brown, Michael S., et al. "Knowledge–based analysis of microarray gene expression data by using support vector machines", PNAS, vol. 97, Jan. 4, 2000, pp. 262–267.

Alon, U., et al., "Broad patterns of gene expression revealed by clustering analysis of tumor normal colon tissues probed by oligonucleotide arrays", PNAS, vol. 96, Jun. 1999, pp. 6745–6750 (Abstract only).

Eisen, M.B., et al., "Cluster analysis and display of genome–wide expression pattersn", Proc. Natl. Acad. Sci. USA, vol. 95, Dec. 1998, pp. 14863–14868 (Abstract only).

Golub, T.R., et al., "Molecular classification of cancer: class discovery and class prediction by gene expression monitoring", Science, vol. 286, Oct. 1999, pp. 531–537 (Abstract only).

Alizadeh, A.A., et al., "Distinct types of diffuse large B–cell lymphoma identified by gene expression profiling", Nature, vol. 403, Issued 3, Feb. 2000, pp. 503–511 (Abstract only).

Thorsteinsdottir, U., et al., "The oncoprotein E2A–Pbx 1A collaborates with Hoxa9 to acutely transform primary bone marrow cells", Molecular Cell Biology, vol. 19, Issue 9, Sep. 1999, pp. 6355–6366 (Abstract only).

Osaka, M., et al., "MSF (MLL septin–like fusion), a fusion partner gene of MLL, in a therapy–related acute myeloid leukemia with a t(II; 17)(q23;125)", Proc. Natl. Acad. Sci. USA, vol. 96, Issue 11, May 1999, pp. 6428–6433 (Abstract only).

Macalma, T., et al., "Molecular characterization of human zyxin", Journal of Biological Chemistry, vol. 271, Issue 49, Dec. 1996, pp. 31470–31478 (Abstract only).

Harlan, D.M., et al., "The human myristoylated alanine rich C kinase substrate (MARCKS) gene (MACS). Analysis of its gene product, promoter, and chromosomal localization", Journal of Biological Chemistry, vol. 266, Issue 12, Aug. 1991, pp. 14399–14405 (Abstract only).

Moser, T.L., et al., "Angiostatin binds ATP Synthase on the surface of human endothelial cells", PNAS, vol. 96, Issue 6, Mar. 1999, pp. 2811–2816 (Abstract only).

Karakiulakis, G., et al., "Increased type IV collagen–degrading activity in metastases originating from primary tumors of the human colon", Invasion and Metastasis, vol. 17, No. 3, 1997, pp. 158–168 (Abstract only).

Ghigna, C., et al., "Altered expression of heterogenous nuclear ribonucleoproteins and SR factors in human colon adenocarcinomas", Cancer Research, vol. 58, Dec. 1998, pp. 5818–5824 (Abstract only).

Perou, C.M., et al., "Distinctive gene expression patterns in human mammary cell epithelial cells and breast cancers", Proc. Natl. Acad. Sci. USA, vol. 96, Aug. 1999, pp. 9212–9217 (Abstract only).

* cited by examiner

| 406a | 406b | 406c | 406d | 406e | 406f |
|---|---|---|---|---|---|
| 41 | 75 | 95 | 29 | 8 | 1 |
| 47 | 64 | 45 | 26 | 4 | 1 |
| 34 | 35 | 17 | 11 | 5 | 1 |
| 48 | 5 | 137 | 18 | 2 | 1 |
| 35 | 29 | 48 | 21 | 9 | 1 |
| 49 | 19 | 69 | 11 | 7 | 1 |
| 42 | 8 | 10 | 12 | 2 | 1 |
| 44 | 3 | 12 | 14 | 1 | 1 |
| 37 | 57 | 19 | 20 | 7 | 1 |
| 48 | 17 | 14 | 12 | 1 | 1 |
| 39 | 1 | 10 | 17 | 8 | 1 |
| 44 | 21 | 14 | 17 | 1 | 1 |
| 34 | 2 | 9 | 12 | 1 | 1 |
| 31 | 10 | 10 | 16 | 0 | 1 |
| 42 | 252 | 452 | 25 | 0 | 1 |
| 42 | 59 | 693 | 19 | 1 | -1 |
| 36 | 5 | 51 | 12 | 1 | -1 |
| 38 | 1 | 10 | 19 | 1 | -1 |
| 36 | 43 | 89 | 9 | 1 | -1 |
| 42 | 16 | 10 | 13 | 4 | -1 |
| 47 | 19 | 20 | 12 | 1 | -1 |
| 49 | 14 | 128 | 21 | 4 | -1 |
| 38 | 169 | 315 | 36 | 0 | -1 |
| 33 | 2 | 12 | 8 | 0 | -1 |
| 46 | 41 | 308 | 23 | 5 | -1 |
| 44 | 54 | 115 | 29 | 2 | -1 |
| 31 | 4 | 3 | 20 | 1 | -1 |
| 49 | 1 | 18 | 27 | 2 | -1 |
| 48 | 34 | 355 | 19 | 3 | -1 |
| 44 | 29 | 19 | 20 | 2 | -1 |
| 42 | 207 | 11 | 10 | 3 | -1 |
| 43 | 62 | 53 | 26 | 1 | -1 |
| 43 | 108 | 293 | 4 | 0 | -1 |
| 35 | 25 | 13 | 24 | 1 | -1 |
| 35 | 5 | 5 | 16 | 1 | -1 |
| 45 | 54 | 17 | 19 | 8 | -1 |
| 41 | 4 | 10 | 15 | 4 | -1 |
| 40 | 8 | 12 | 8 | 0 | -1 |
| 42 | 25 | 78 | 21 | 2 | -1 |
| 46 | 30 | 105 | 11 | 5 | -1 |
| 48 | 72 | 94 | 15 | 1 | -1 |
| 36 | 3 | 10 | 7 | 0 | -1 |
| 46 | 165 | 12 | 17 | 5 | -1 |
| 47 | 22 | 10 | 26 | 2 | -1 |
| 48 | 3 | 10 | 21 | 0 | -1 |
| 40 | 4 | 10 | 12 | 0 | -1 |
| 32 | 3 | 10 | 14 | 6 | 1 |
| 36 | 51 | 167 | 11 | 3 | 1 |
| 39 | 4 | 15 | 31 | 25 | 1 |
| 46 | 2 | 10 | 8 | 0 | 1 |
| 28 | 12 | 36 | 25 | 23 | 1 |
| 32 | 23 | 50 | 19 | 0 | 1 |
| 44 | 26 | 10 | 21 | 4 | 1 |
| 47 | 32 | 11 | 21 | 7 | 1 |
| 42 | 32 | 41 | 21 | 18 | -1 |
| 42 | 2 | 10 | 14 | 0 | -1 |
| 36 | 10 | 1 | 16 | 1 | -1 |
| 47 | 5 | 6 | 22 | 1 | -1 |
| 34 | 18 | 6 | 13 | 2 | -1 |
| 34 | 9 | 10 | 29 | 0 | -1 |
| 37 | 6 | 10 | 16 | 0 | -1 |
| 38 | 42 | 46 | 14 | 6 | -1 |
| 32 | 98 | 11 | 11 | 0 | -1 |
| 37 | 39 | 10 | 13 | 1 | -1 |
| 45 | 17 | 267 | 20 | 4 | -1 |
| 39 | 93 | 134 | 12 | 1 | -1 |
| 43 | 47 | 11 | 19 | 11 | -1 |
| 46 | 6 | 10 | 13 | 1 | -1 |
| 49 | 1 | 4 | 19 | 6 | -1 |
| 46 | 172 | 302 | 9 | 3 | -1 |

Rows 1–46 of the table belong to group 402; rows 47–68 belong to group 404.

FIG.4

Vapnik's Polynomial

Alphas bounded up to 1000.
Input values will be individually scaled to be between 0 and 1.
SV zero threshold: 1e-16.
Margin threshold: 0.1
Objective zero tolerance: 1e-07
Degree of polynomial: 2.

Test set:
Total samples:      24
Positive samples:   8
of which errors:    4
Negative samples:  16
of which errors:    6

FIG.5

| 606a | 606a1 | 606a3 | 606b1-3 | | | 606c1-3 | | | 606d1-3 | | | 606e1-3 | | | 606f |
|---|---|---|---|---|---|---|---|---|---|---|---|---|---|---|---|
| | 606a2 | | 606b | | | 606c | | | 606d | | | 606e | | | |
| 41 | 0 | 0 | 1 | 75 | 0 | 0 | 1 | 95 | 0 | 0 | 1 | 29 | 0 | 0 | 1 | 8 | 0 | 0 | 1 | 1 |

(table data is a large numeric grid; see figure)

Vapnik's Polynomial

Alphas bounded up to 1000.
Input values will be individually scaled to be between 0 and 1.
SV zero threshold: 1e-16.
Margin threshold: 0.1
Objective zero tolerance: 1e-07
Degree of polynomial: 2.

Test set:
Total samples:      24
Positive samples:    8
of which errors:     4
Negative samples:   16
of which errors:     4

FIG. 7

| 801 | | |
|---|---|---|
| 802 | 804 | 808 |

| Cut Point | Correctly Classified Recurrence | Correctly Class Non-Recurrenc |
|---|---|---|
| Clinical (≥3.0) | 7 of 15 (47%) | 22 of 31 (71%) |
| Optimal (≥5.5) | 5 of 15 (33%) | 30 of 31 (97%) |

| 802 | 804 |
|---|---|
| 8 | 0 |
| 4 | 0 |
| 5 | 0 |
| 2 | 0 |
| 9 | 0 |
| 7 | 0 |
| 2 | 0 |
| 1 | 0 |
| 7 | 0 |
| 1 | 0 |
| 8 | 0 |
| 1 | 0 |
| 1 | 0 |
| 0 | 0 |
| 0 | 0 |
| 1 | 1 |
| 1 | 1 |
| 1 | 1 |
| 1 | 1 |
| 4 | 1 |
| 1 | 1 |
| 4 | 1 |
| 0 | 1 |
| 0 | 1 |
| 5 | 1 |
| 2 | 1 |
| 1 | 1 |
| 2 | 1 |
| 3 | 1 |
| 2 | 1 |
| 3 | 1 |
| 1 | 1 |
| 0 | 1 |
| 1 | 1 |
| 1 | 1 |
| 8 | 1 |
| 4 | 1 |
| 0 | 1 |
| 2 | 1 |
| 5 | 1 |
| 1 | 1 |
| 0 | 1 |
| 5 | 1 |
| 2 | 1 |
| 0 | 1 |
| 0 | 1 |

Number of subintervals: 2
Number of classes: 2
Number of data points: 46
Lower bound: -1
Upper bound: 10
Number of bins: 22

Regularization constant: 1
Data file: posnodes.prn
Min Entropy - 0.568342
5.500000 ←———— 806

Simple Dot Product

Alphas bounded up to 1000.
Input values will not be scaled.
SV zero threshold: 1e-16.
Margin threshold: 0.1
Objective zero tolerance: 1e-07

Test set:
Total samples: 24
Positive samples: 8
of which errors: 6
Negative samples: 16
of which errors: 3

904

Valpik's Polynomial

Alphas bounded up to 1000.
Input values will not be scaled.
SV zero threshold: 1e-16.
Margin threshold: 0.1
Objective zero tolerance: 1e-07
Degree of Polynomial: 2.

Test set:
Total samples: 24
Positive samples: 8
of which errors: 2
Negative samples: 16
of which errors: 4

FIG. 9

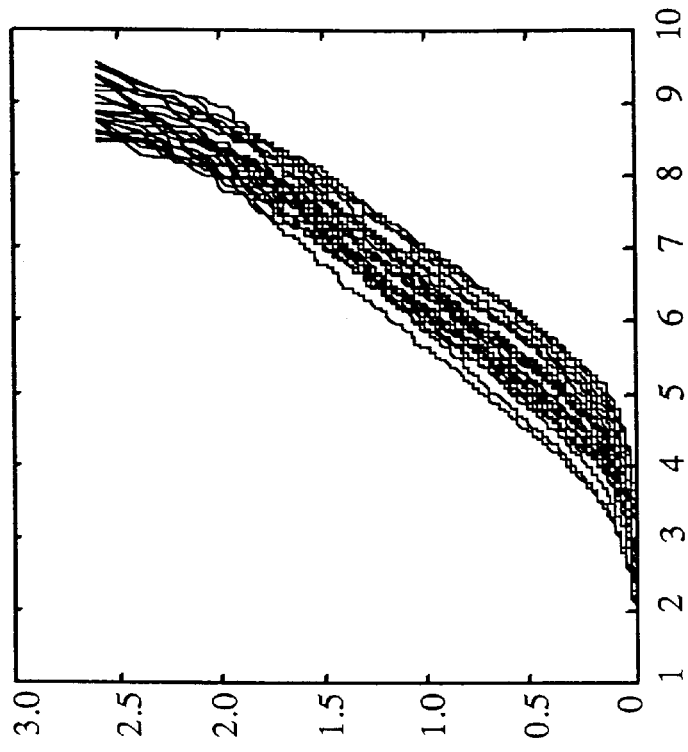
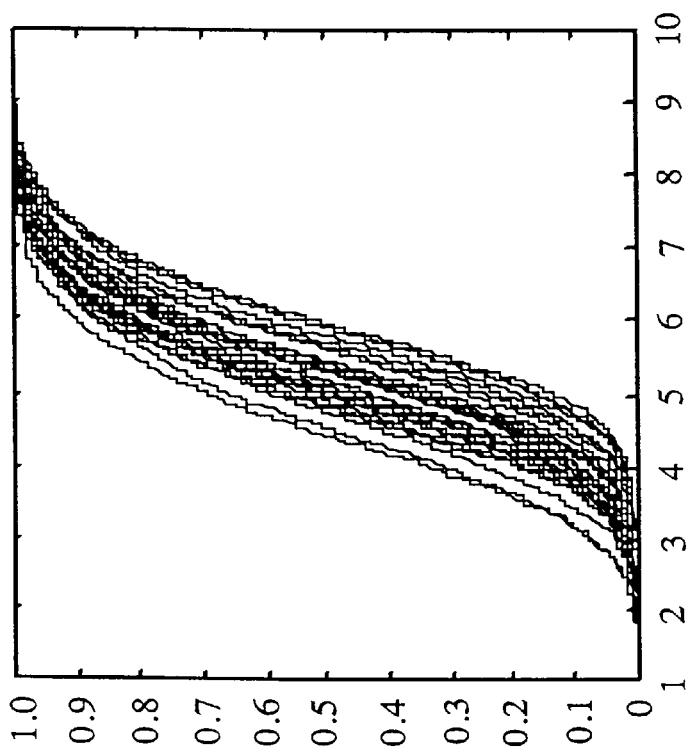
FIG. 16A
FIG. 16B

- ● test success rate
- ■ leave-one-out quality criterion
- ♦ (smoothed) predictor of optimum test success rate
- ▲ epsilon (theoretical error bar)

- ● test success rate
- ■ leave-one-out quality criterion
- ♦ (smoothed) predictor of optimum test success rate
- ▲ epsilon (theoretical error bar)

- ● test success rate
- ■ leave-one-out quality criterion
- ▲ epsilon (theoretical error bar)
- ♦ (smoothed) predictor of optimum test success rate

- ● training success rate
- — leave-one-out success rate
- ■ leave-one-out quality criterion
- ◆ (smoothed) predictor of optimum test success rate
- ▲ epsilon (theoretical error bar)

- ● training success rate
- — leave-one-out success rate
- ■ leave-one-out quality criterion
- ◆ epsilon (theoretical error bar)
- ▲ (smoothed) predictor of optimum test success rate

FIG. 28A   FIG. 28B
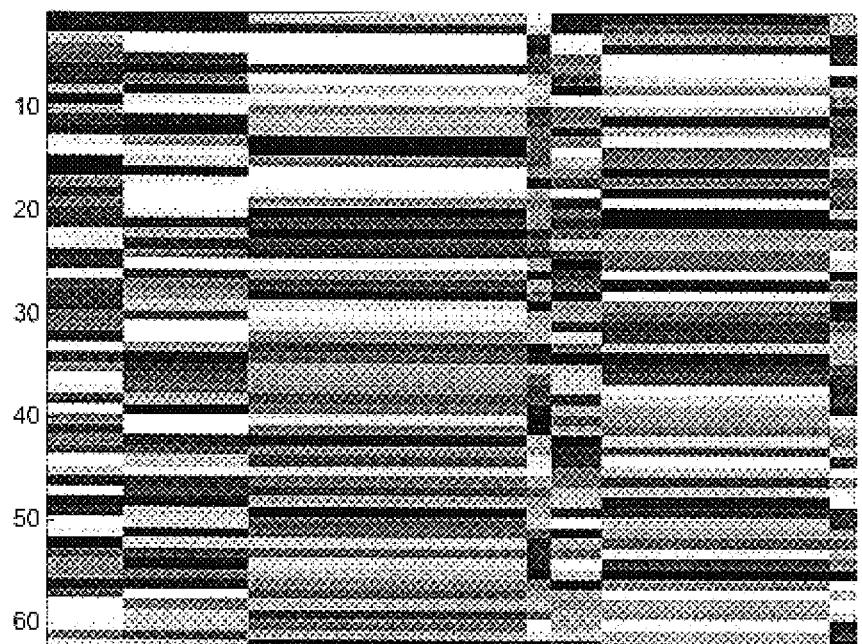
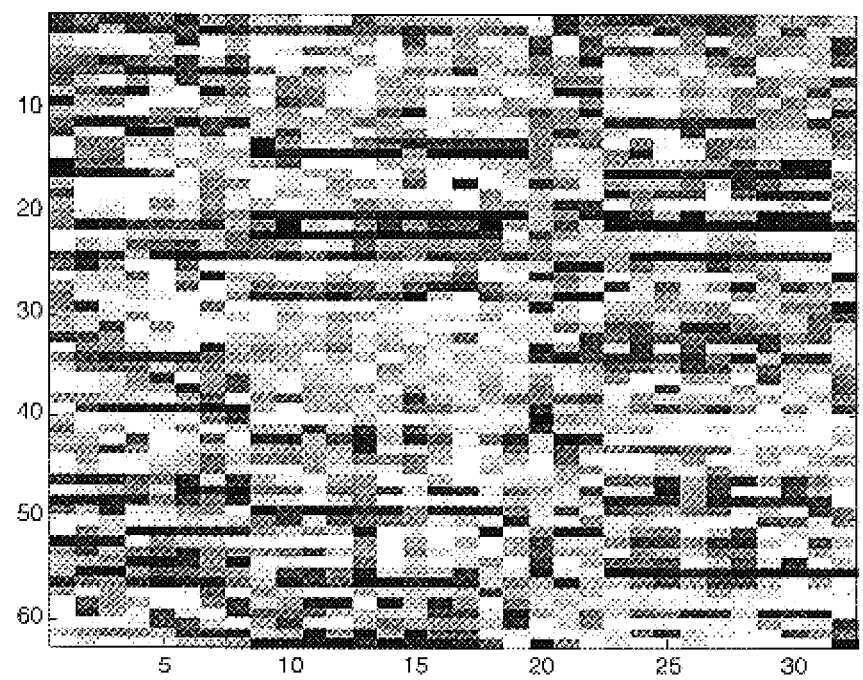
FIG. 28C

FIG. 29A    FIG. 29B
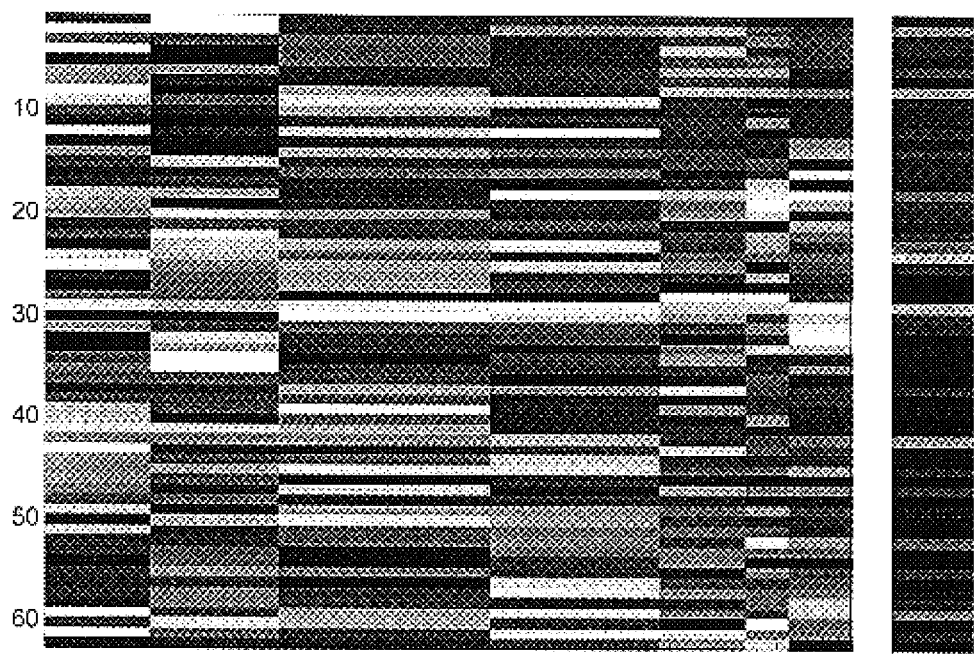
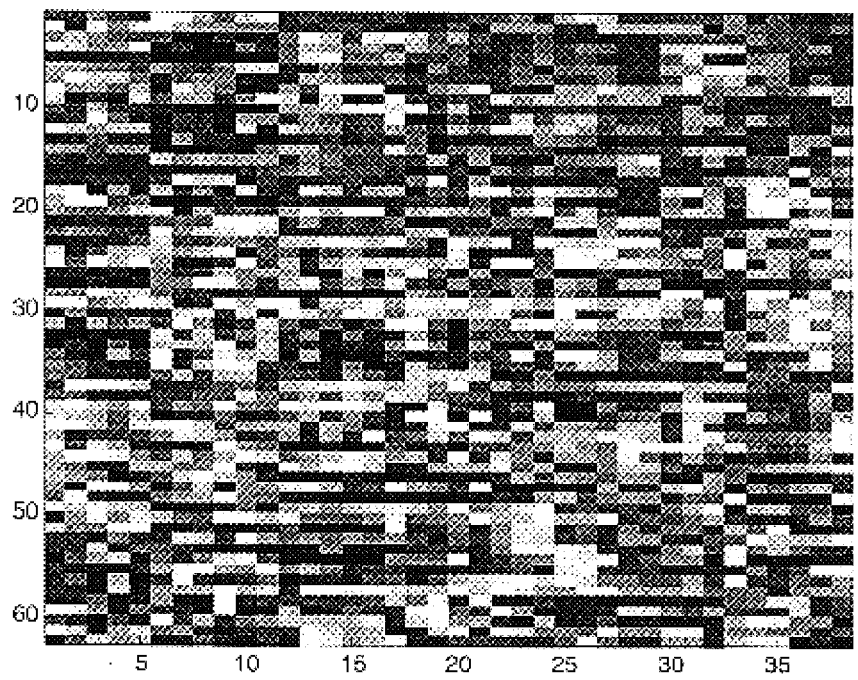
FIG. 29C

- ● SVM
- ◆ MSE
- ■ LD
- ▲ Baseline

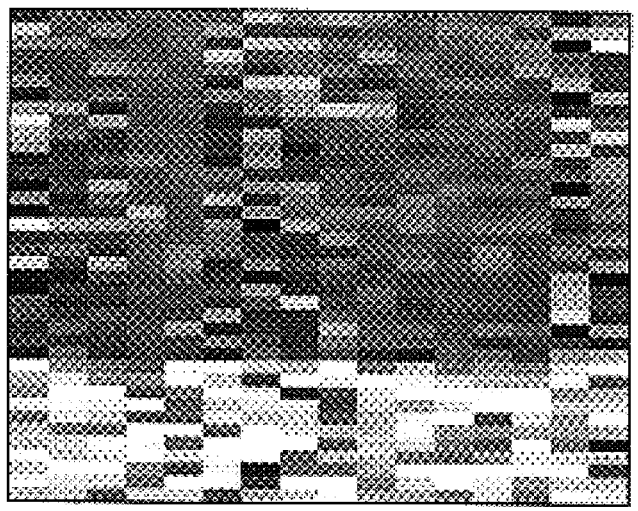 
FIG. 33A      FIG. 33B
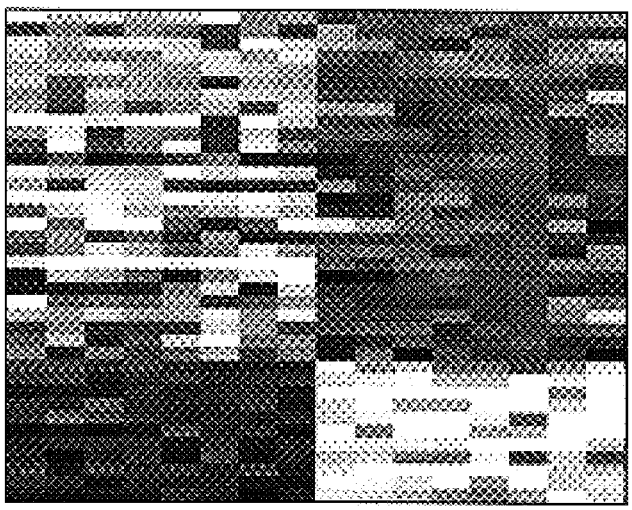 
FIG. 33C      FIG. 33D

- ● error rate on the test set
- ■ scaled quality criterion (Q/4)
- ▲ scaled theoretical error bar (e/2)
- ♦ result of locally smoothing the C/4

- ● error rate on the test set
- ■ scaled quality criterion (Q/4)
- ▲ scaled theoretical error bar (e/2)
- ♦ result of locally smoothing the C/4

METHOD FOR ENHANCING KNOWLEDGE DISCOVERED FROM BIOLOGICAL DATA USING A LEARNING MACHINE

RELATED APPLICATIONS

This appln claims benefit of 60/161,806 Oct. 27, 1999 and claims benefit of 60/168,703 Dec. 27, 1999 and claims benefit of 60/184,596 Feb. 24, 2000 and claims benefit of 60/191,219 Mar. 22, 2000 U.S. Pat. No. 6,658,395 and is a CIP of Ser. No. 09/578,011 May 24, 2000 now U.S. Pat. No. 6,658,395 which claims benefit of 60/135,715 May 25, 1999 and is a CIP of Ser. No. 09/568,301 May 9, 2000 U.S. Pat. No. 6,427,141 which is a CON of Ser. No. 09/303,387 May 1, 1999 U.S. Pat. No. 6,128,608 and is a CON of Ser. No. 09/305,345 May 1, 1999 U.S. Pat. No. 6,157,921 and is a CON of Ser. No. 09/303,386 May 1, 1999 abandoned and is a CON of Ser. No. 09/303,389 May 1, 1999 abandoned which claims benefit of 60/083,961 May 1, 1998

TECHNICAL FIELD

The present invention relates to the use of learning machines to identify relevant patterns in biological systems such as genes, gene products, proteins, lipids, and combinations of the same. These patterns in biological systems can be used to diagnose and prognose abnormal physiological states. In addition, the patterns that can be detected using the present invention can be used to develop therapeutic agents.

BACKGROUND OF THE INVENTION

Enormous amounts of data about organisms are being generated in the sequencing of genomes. Using this information to provide treatments and therapies for individuals will require an in-depth understanding of the gathered information. Efforts using genomic information have already led to the development of gene expression investigational devices. One of the most currently promising devices is the gene chip. Gene chips have arrays of oligonucleotide probes attached a solid base structure. Such devices are described in U.S. Pat. Nos. 5,837,832 and 5,143,854, herein incorporated by reference in their entirety. The oligonucleotide probes present on the chip can be used to determine whether a target nucleic acid has a nucleotide sequence identical to or different from a specific reference sequence. The array of probes comprise probes that are complementary to the reference sequence as well as probes that differ by one of more bases from the complementary probes.

The gene chips are capable of containing large arrays of otiogonucleotides on very small chips. A variety of methods for measuring hybridization intensity data to determine which probes are hybridizing is known in the art. Methods for detecting hybridization include fluorescent, radioactive, enzymatic, chemoluminescent, bioluminescent and other detection systems.

Older, but still usable, methods such as gel electrophosesis and hybridization to gel blots or dot blots are also useful for determining genetic sequence information. Capture and detection systems for solution hybridization and in situ hybridization methods are also used for determining information about a genome. Additionally, former and currently used methods for defining large parts of genomic sequences, such as chromosome walking and phage library establishment, are used to gain knowledge about genomes.

Large amounts of information regarding the sequence, regulation, activation, binding sites and internal coding signals can be generated by the methods known in the art. In fact, the amount of data being generated by such methods hinders the derivation of useful information. Human researchers, when aided by advanced learning tools such as neural networks can only derive crude models of the underlying processes represented in the large, feature-rich datasets.

Another area of biological investigation that can generate a huge amount of data is the emerging field of proteomics. Proteomics is the study of the group of proteins encoded and regulated by a genome. This field represents a new focus on analyzing proteins, regulation of protein levels and the relationship to gene regulation and expression. Understanding the normal or pathological state of the proteome of a person or a population provides information for the prognosis or diagnosis of disease, development of drug or genetic treatments, or enzyme replacement therapies. Current methods of studying the proteome involve 2-dimensional (2-D) gel electrophoresis of the proteins followed by analysis by mass spectrophotometry. A pattern of proteins at any particular time or stage in pathologenesis or treatment can be observed by 2-D gel electrophoresis. Problems arise in identifying the thousands of proteins that are found in cells that have been separated on the 2-D gels. The mass spectrophotometer is used to identify a protein isolated from the gel by identifying the amino acid sequence and comparing it to known sequence databases. Unfortunately, these methods require multiple steps to analyze a small portion of the proteome.

In recent years, technologies have been developed that can relate gene expression to protein production structure and function. Automated high-throughput analysis, nucleic acid analysis and bioinformatics technologies have aided in the ability to probe genomes and to link gene mutations and expression with disease predisposition and progression. The current analytical methods are limited in their abilities to manage the large amounts of data generated by these technologies.

One of the most recent advances in determining the functioning parameters of biological systems is the analysis of correlation of genomic information with protein functioning to elucidate the relationship between gene expression, protein function and interaction, and disease states or progression. Genomic activation or expression does not always mean direct changes in protein production levels or activity. Alternative processing of mRNA or post-transcriptional or post-translational regulatory mechanisms may cause the activity of one gene to result in multiple proteins, all of which are slightly different with different migration patterns and biological activities. The human genome potentially contains 100,000 genes but the human proteome is believed to be 50 to 100 times larger. Currently, there are no methods, systems or devices for adequately analyzing the data generated by such biological investigations into the genome and proteome.

Knowledge discovery is the most desirable end product of data collection. Recent advancements in database technology have lead to an explosive growth in systems and methods for generating, collecting and storing vast amounts of data. While database technology enables efficient collection and storage of large data sets, the challenge of facilitating human comprehension of the information in this data is growing ever more difficult. With many existing techniques the problem has become unapproachable. Thus, there remains a need for a new generation of automated knowledge discovery tools.

As a specific example, the Human Genome Project is populating a multi-gigabyte database describing the human genetic code. Before this mapping of the human genome is complete, the size of the database is expected to grow significantly. The vast amount of data in such a database overwhelms traditional tools for data analysis, such as spreadsheets and ad hoc queries. Traditional methods of data analysis may be used to create informative reports from data, but do not have the ability to intelligently and automatically assist humans in analyzing and finding patterns of useful knowledge in vast amounts of data. Likewise, using traditionally accepted reference ranges and standards for interpretation, it is often impossible for humans to identify patterns of useful knowledge even with very small amounts of data.

One recent development that has been shown to be effective in some examples of machine learning is the back-propagation neural network. Back-propagation neural networks are learning machines that may be trained to discover knowledge in a data set that may not be readily apparent to a human. However, there are various problems with back-propagation neural network approaches that prevent neural networks from being well-controlled learning machines. For example, a significant drawback of back-propagation neural networks is that the empirical risk function may have many local minimums, a case that can easily obscure the optimal solution from discovery by this technique. Standard optimization procedures employed by back-propagation neural networks may converge to an answer, but the neural network method cannot guarantee that even a localized minimum is attained much less the desired global minimum. The quality of the solution obtained from a neural network depends on many factors. In particular the skill of the practitioner implementing the neural network determines the ultimate benefit, but even factors as seemingly benign as the random selection of initial weights can lead to poor results. Furthermore, the convergence of the gradient based method used in neural network learning is inherently slow. A further drawback is that the sigmoid activation function has a scaling factor, which affects the quality of approximation. Possibly the largest limiting factor of neural networks as related to knowledge discovery is the "curse of dimensionality" associated with the disproportionate growth in required computational time and power for each additional feature or dimension in the training data.

The shortcomings of neural networks are overcome using support vector machines. In general terms, a support vector machine maps input vectors into high dimensional feature space through non-linear mapping function, chosen a priori. In this high dimensional feature space, an optimal separating hyperplane is constructed. The optimal hyperplane is then used to determine things such as class separations, regression fit, or accuracy in density estimation.

Within a support vector machine, the dimensionally of the feature space may be huge. For example, a fourth degree polynomial mapping function causes a 200 dimensional input space to be mapped into a 1.6 billionth dimensional feature space. The kernel trick and the Vapnik-Chervonenkis dimension allow the support vector machine to thwart the "curse of dimensionality" limiting other methods and effectively derive generalizable answers from this very high dimensional feature space. Patent applications directed to support vector machines include, U.S. patent application Ser. Nos. 09/303,386; 09/303,387; 09/303,389; 09/305,345; all filed May 1, 1999; and U.S. patent application Ser. No. 09/568,301, filed May 9, 2000; and U.S. patent application Ser. No. 09/578,011, filed May 24, 2000 and also claims the benefit of U.S. Provisional Patent Application No. 60/161, 806, filed Oct. 27, 1999; of U.S. Provisional Patent Application No. 60/168,703, filed Dec. 2, 1999; of U.S. Provisional Patent Application No. 60/184,596, filed Feb. 24, 2000; and of U.S. Provisional Patent Application Serial No. 60/191,219, filed Mar. 22, 2000; all of which are herein incorporated in their entireties.

If the training vectors are separated by the optimal hyperplane (or generalized optimal hyperplane), then the expectation value of the probability of committing an error on a test example is bounded by the examples in the training set. This bound depends neither on the dimensionality of the feature space, nor on the norm of the vector of coefficients, nor on the bound of the number of the input vectors. Therefore, if the optimal hyperplane can be constructed from a small number of support vectors relative to the training set size, the generalization ability will be high, even in infinite dimensional space.

The data generated from genomic and proteomic tests can be analyzed from many different viewpoints. For example, the literature shows simple approaches such as studies of gene clusters discovered by unsupervised learning techniques (Alon, 1999). Clustering is often also done along the other dimension of the data. For example, each experiment may correspond to one patient carrying or not carrying a specific disease (see e.g. (Golub, 1999)). In this case, clustering usually groups patients with similar clinical records. Supervised learning has also been applied to the classification of proteins (Brown, 2000) and to cancer classification (Golub, 1999).

Support vector machines provide a desirable solution for the problem of discovering knowledge from vast amounts of input data. However, the ability of a support vector machine to discover knowledge from a data set is limited in proportion to the information included within the training data set. Accordingly, there exists a need for a system and method for pre-processing data so as to augment the training data to maximize the knowledge discovery by the support vector machine.

Furthermore, the raw output from a support vector machine may not fully disclose the knowledge in the most readily interpretable form. Thus, there further remains a need for a system and method for post-processing data output from a support vector machine in order to maximize the value of the information delivered for human or further automated processing.

In addition, the ability of a support vector machine to discover knowledge from data is limited by the selection of a kernel. Accordingly, there remains a need for an improved system and method for selecting and/or creating a desired kernel for a support vector machine.

What is also needed are methods, systems and devices that can be used to manipulate the information contained in the databases generated by investigations of proteomics and genomics. Also, methods, systems and devices are needed that can integrate information from genomic, proteomic and traditional sources of biological information. Such information is needed for the diagnosis and prognosis of diseases and other changes in biological and other systems.

Furthermore, what are needed are methods and compositions for treating the diseases and other changes in biological systems that are indentified by the support vector machine. Once patterns or the relationships between the data are identified by the support vector machines of the present invention and are used to detect or diagnose a particular disease state, what is needed are diagnostic tests, including gene chips and test of bodily fluids or bodily changes, and methods and compositions for treating the condition.

SUMMARY OF THE INVENTION

The present invention comprises systems and methods for enhancing knowledge discovered from data using a learning machine in general and a support vector machine in particular. In particular, the present invention comprises methods of using a learning machine for diagnosing and prognosing changes in biological systems such as diseases. Further, once the knowledge discovered from the data is determined, the specific relationships discovered are used to diagnose and prognose diseases, and methods of detecting and treating such diseases are applied to the biological system.

One embodiment of the present invention comprises preprocessing a training data set in order to allow the most advantageous application of the learning machine. Each training data point comprises a vector having one or more coordinates. Pre-processing the training data set may comprise identifying missing or erroneous data points and taking appropriate steps to correct the flawed data or as appropriate remove the observation or the entire field from the scope of the problem. Pre-processing the training data set may also comprise adding dimensionality to each training data point by adding one or more new coordinates to the vector. The new coordinates added to the vector may be derived by applying a transformation to one or more of the original coordinates. The transformation may be based on expert knowledge, or may be computationally derived. In a situation where the training data set comprises a continuous variable, the transformation may comprise optimally categorizing the continuous variable of the training data set.

In a preferred embodiment, the support vector machine is trained using the pre-processed training data set. In this manner, the additional representations of the training data provided by the preprocessing may enhance the learning machine's ability to discover knowledge therefrom. In the particular context of support vector machines, the greater the dimensionality of the training set, the higher the quality of the generalizations that may be derived therefrom. When the knowledge to be discovered from the data relates to a regression or density estimation or where the training output comprises a continuous variable, the training output may be post-processed by optimally categorizing the training output to derive categorizations from the continuous variable.

A test data set is pre-processed in the same manner as was the training data set. Then, the trained learning machine is tested using the pre-processed test data set. A test output of the trained learning machine may be post-processing to determine if the test output is an optimal solution. Post-processing the test output may comprise interpreting the test output into a format that may be compared with the test data set. Alternative postprocessing steps may enhance the human interpretability or suitability for additional processing of the output data.

In the context of a support vector machine, the present invention also provides for the selection of at least one kernel prior to training the support vector machine. The selection of a kernel may be based on prior knowledge of the specific problem being addressed or analysis of the properties of any available data to be used with the learning machine and is typically dependant on the nature of the knowledge to be discovered from the data. Optionally, an iterative process comparing postprocessed training outputs or test outputs can be applied to make a determination as to which configuration provides the optimal solution. If the test output is not the optimal solution, the selection of the kernel may be adjusted and the support vector machine may be retrained and retested. When it is determined that the optimal solution has been identified, a live data set may be collected and pre-processed in the same manner as was the training data set. The pre-processed live data set is input into the learning machine for processing. The live output of the learning machine may then be post-processed by interpreting the live output into a computationally derived alphanumeric classifier or other form suitable to further utilization of the SVM derived answer.

In an exemplary embodiment a system is provided enhancing knowledge discovered from data using a support vector machine. The exemplary system comprises a storage device for storing a training data set and a test data set, and a processor for executing a support vector machine. The processor is also operable for collecting the training data set from the database, pre-processing the training data set to enhance each of a plurality of training data points, training the support vector machine using the pre-processed training data set, collecting the test data set from the database, pre-processing the test data set in the same manner as was the training data set, testing the trained support vector machine using the pre-processed test data set, and in response to receiving the test output of the trained support vector machine, post-processing the test output to determine if the test output is an optimal solution. The exemplary system may also comprise a communications device for receiving the test data set and the training data set from a remote source. In such a case, the processor may be operable to store the training data set in the storage device prior pre-processing of the training data set and to store the test data set in the storage device prior pre-processing of the test data set. The exemplary system may also comprise a display device for displaying the post-processed test data. The processor of the exemplary system may further be operable for performing each additional function described above. The communications device may be further operable to send a computationally derived alphanumeric classifier or other SVM-based raw or post-processed output data to a remote source.

In an exemplary embodiment, a system and method are provided for enhancing knowledge discovery from data using multiple learning machines in general and multiple support vector machines in particular. Training data for a learning machine is pre-processed in order to add meaning thereto. Pre-processing data may involve transforming the data points and/or expanding the data points. By adding meaning to the data, the learning machine is provided with a greater amount of information for processing. With regard to support vector machines in particular, the greater the amount of information that is processed, the better generalizations about the data that may be derived. Multiple support vector machines, each comprising distinct kernels, are trained with the pre-processed training data and are tested with test data that is pre-processed in the same manner. The test outputs from multiple support vector machines are compared in order to determine which of the test outputs if any represents an optimal solution. Selection of one or more kernels may be adjusted and one or more support vector machines may be retrained and retested. When it is determined that an optimal solution has been achieved, live data is pre-processed and input into the support vector machine comprising the kernel that produced the optimal solution. The live output from the learning machine may then be post-processed into a computationally derived alphanumeric classifier for interpretation by a human or computer automated process.

In another exemplary embodiment, systems and methods are provided for optimally categorizing a continuous variable. A data set representing a continuous variable comprises data points that each comprise a sample from the continuous variable and a class identifier. A number of distinct class identifiers within the data set is determined and a number of candidate bins is determined based on the range of the samples and a level of precision of the samples within the data set. Each candidate bin represents a sub-range of the samples. For each candidate bin, the entropy of the data points falling within the candidate bin is calculated. Then, for each sequence of candidate bins that have a minimized collective entropy, a cutoff point in the range of samples is defined to be at the boundary of the last candidate bin in the sequence of candidate bins. As an iterative process the collective entropy for different combinations of sequential candidate bins may be calculated.

Also the number of defined cutoff points may be adjusted in order to determine the optimal number of cutoff points, which is based on a calculation of minimal entropy. As mentioned, the exemplary system and method for optimally categorizing a continuous variable may be used for pre-processing data to be input into a learning machine and for post-processing output of a learning machine.

In still another exemplary embodiment, a system and method are provided for for enhancing knowledge discovery from data using a learning machine in general and a support vector machine in particular in a distributed network environment. A customer may transmit training data, test data and live data to a vendor's server from a remote source, via a distributed network. The customer may also transmit to the server identification information such as a user name, a password and a financial account identifier. The training data, test data and live data may be stored in a storage device. Training data may then be pre-processed in order to add meaning thereto. Pre-processing data may involve transforming the data points and/or expanding the data points. By adding meaning to the data, the learning machine is provided with a greater amount of information for processing. With regard to support vector machines in particular, the greater the amount of information that is processed, the better generalizations about the data that may be derived. The learning machine is therefore trained with the pre-processed training data and is tested with test data that is pre-processed in the same manner. The test output from the learning machine is post-processed in order to determine if the knowledge discovered from the test data is desirable. Post-processing involves interpreting the test output into a format that may be compared with the test data. Live data is pre-processed and input into the trained and tested learning machine. The live output from the learning machine may then be post-processed into a computationally derived alpha-numerical classifier for interpretation by a human or computer automated process. Prior to transmitting the alpha numerical classifier to the customer via the distributed network, the server is operable to communicate with a financial institution for the purpose of receiving funds from a financial account of the customer identified by the financial account identifier.

BRIEF DESCRIPTION OF THE DRAWINGS

FIG. 4 illustrates an exemplary unexpanded data set that may be input into a support vector machine.

FIG. 5 illustrates an exemplary post-processed output generated by a support vector machine using the data set of FIG. 4.

FIG. 6 illustrates an exemplary expanded data set that may be input into a support vector machine based on the data set of FIG. 4.

FIG. 7 illustrates an exemplary post-processed output generated by a support vector machine using the data set of FIG. 6.

FIG. 8 illustrates exemplary input and output for a standalone application of the optimal categorization method of FIG. 3.

FIG. 9 is a comparison of exemplary post-processed output from a first support vector machine comprising a Linear kernel and a second support vector machine comprising a polynomial kernel.

FIGS. 16A and 16B show the of gene expression values across genes for all tissue samples.

FIGS. 28A, 28B and 28C show the top ranked genes discovered by SVM RFE in order of increasing importance from left to right.

FIGS. 29A, 29B and 29C show the 7 top ranked genes discovered by Golub's methods in order of increasing importance from left to right.

FIGS. 33A, 33B, 33C and 33D shows the best set of 16 genes for the leukemia data.

DETAILED DESCRIPTION

Figure 1:
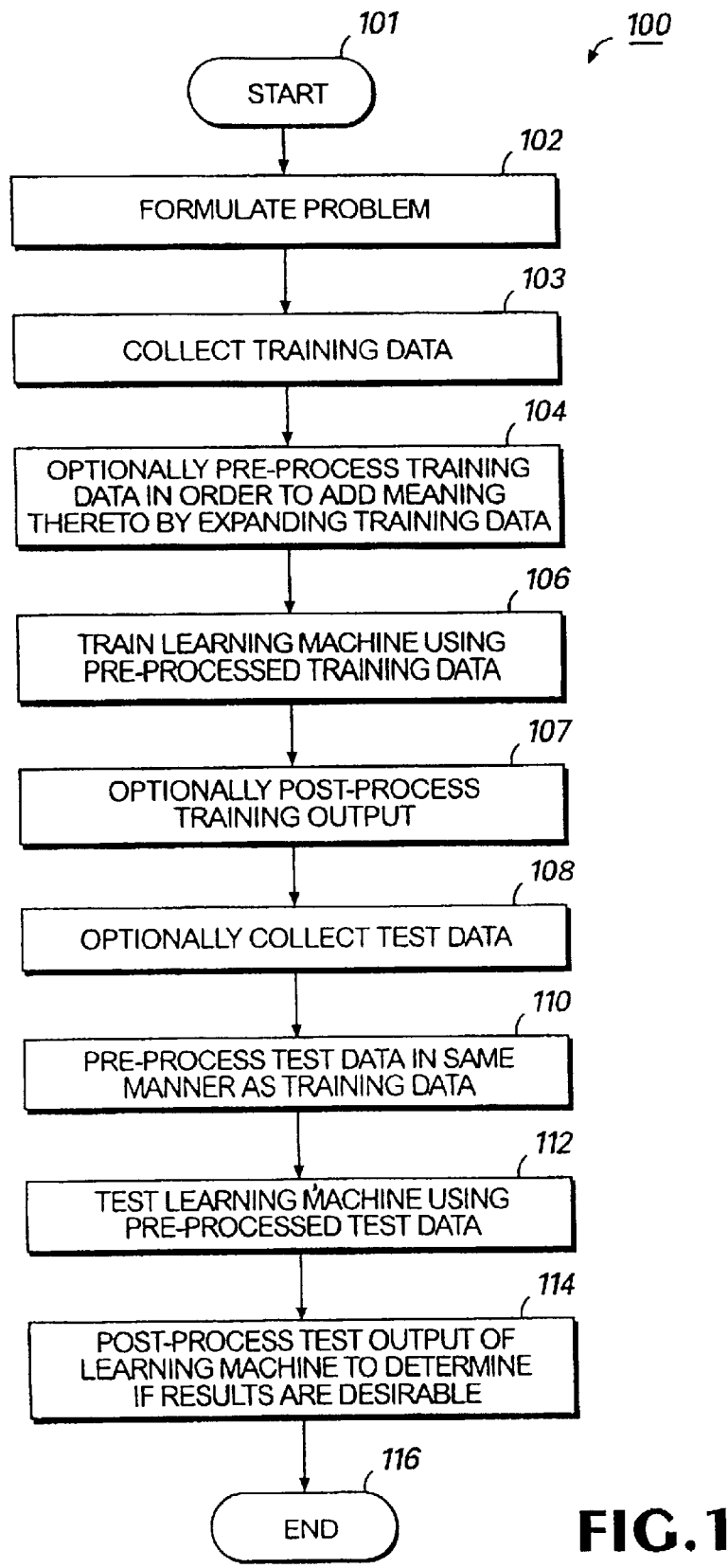
FIG. 1 is a flowchart illustrating an exemplary general method for increasing knowledge that may be discovered from data using a learning machine.

The following detailed description utilizes a number of acronyms, which are generally well known in the art. While definitions are typically provided with the first instance of each acronym,, for convenience, Table 1A and Table 1B below provide a list of the acronyms and abbreviations used along with their respective definitions. Table 1A lists acronyms and abbreviations generally associated with computer technology, whereas Table 1B lists acronyms and abbreviations generally associated with biotechnology.

TABLE 1A

| Acronym | Description |
| --- | --- |
| 2-D | 2 Dimensional |
| ATAPI | Attachment Packet Interface |
| BSVP | Biowulf Support Vector Processor |
| CD-ROM | Compact Disk Read Only Memory |
| DAT | Digital Audio Tape |
| DMA | Direct Memory Access |
| EIDE | Enhanced Integrated Drive Electronics |
| GFLOPS | Giga Floating Operations Per Second |
| I/O | Input/Output |
| IDE | Integrated Drive Electronics |
| KVM Switch | Keyboard/Video/Mouse |
| LAN | Local Area Network |
| MPI | Message Passing Interface |
| NFS | Network File System |
| NIC | Network Interface Card |
| NIS | Network Information Service |
| PVM | Parallel Virtual Machine |
| RAM | Random Access Memory |
| SCSI | Small Computer System Interface |
| SMP | Symmetric Multi Processing |
| SVM | Support Vector Machine |
| WAN | Wide Area Network |

TABLE 1B

| Acronym | Description |
| --- | --- |
| ADP | Adenosine 5'-diphosphate |
| ALL | Acute Lymphocytic Leukemia |
| AML | Acute Myelogenous Leukemia |

TABLE 1B-continued

| Acronym | Description |
| --- | --- |
| ATP | Adenosine 5'-triphosphate |
| CCD | Charge Couple Device |
| CRP | Cysteine-rich Protein |
| DNA | Deoxyribonucleic acid |
| ELISA | Enzyme Linked Immuno- Sorbent Assay |
| EST | Expressed Sequence Tags |
| GAN | Gene Accession Number |
| GCAP | Globular Activator Protein |
| LDA | Linear Discriminant Analysis |
| mRNA | Messenger RNA |
| MSE | Mean-Squared-Error |
| ORF | Open Reading Frames |
| PCR | Polymerase Chain Reaction |
| PIM | Protein Interaction Maps |
| RFE | Recursive Feature Elimination |
| RNA | Ribonucleic acid |

The present invention provides methods, systems and devices for discovering knowledge from data using learning machines. Particularly, the present invention is directed to methods, systems and devices for knowledge discovery from data using learning machines that are provided information regarding changes in biological systems. More particularly, the present invention comprises methods of use of such knowledge for diagnosing and prognosing changes in biological systems such as diseases. Additionally, the present invention comprises methods, compositions and devices for applying such knowledge to the testing and treating of individuals with changes in their individual biological systems.

As used herein, "biological data" means any data derived from measuring biological conditions of human, animals or other biological organisms including microorganisms, viruses, plants and other living organisms. The measurements may be made by any tests, assays or observations that are known to physicians, scientists, diagnosticians, or the like. Biological data may include, but is not limited to, clinical tests and observations, physical and chemical measurements, genomic determinations, proteomic determinations, drug levels, hormonal and immunological tests, neurochemical or neurophysical measurements, mineral and vitamin level determinations, genetic and familial histories, and other determinations that may give insight into the state of the individual or individuals that are undergoing testing. Herein, the use of the term "data" is used interchangeably with "biological data".

While several examples of learning machines exist and advancements are expected in this field, the exemplary embodiments of the present invention focus on the support vector machine. As is known in the art, learning machines comprise algorithms that may be trained to generalize using data with known outcomes. Trained learning machine algorithms may then be applied to cases of unknown outcome for prediction. For example, a learning machine may be trained to recognize patterns in data, estimate regression in data or estimate probability density within data. Learning machines may be trained to solve a wide variety of problems as known to those of ordinary skill in the art. A trained learning machine may optionally be tested using test data to ensure that its output is validated within an acceptable margin of error. Once a learning machine is trained and tested, live data may be input therein. The live output of a learning machine comprises knowledge discovered from all of the training data as applied to the live data.

The present invention comprises methods, systems and devices for analyzing patterns found in biological data, data such as that generated by examination of genes, transcriptional and translational products and proteins. Genomic information can be found in patterns generated by hybridization reactions of genomic fragments and complementary nucleic acids or interacting proteins. One of the most recent tools for investigating such genomic or nucleic acid interactions is the DNA gene chip or mnicroarray. The microarray allows for the processing of thousands of nucleic interactions. DNA microarrays enable researchers to screen thousands of genes in one experiment. For example, the microarray could contain 2400 genes on a small glass slide and can be used to determine the presence of DNA or RNA in the sample. Such microarray tests can be used in basic research and biomedical research including tumor biology, neurosciences, signal transduction, transcription regulation, and cytokine and receptor studies. Additionally, there are applications for pharmaceutical drug discovery, target identification, lead optimization, pharmacokinetics, pharmacogenomics and diagnostics. The market for microarray technology was approximately $98 million in 1999 and the amount of data generated and stored in databases developed from multiple microarray tests is enormous. The present invention provides for methods, systems and devices that can use the data generated in such mnicroarray and nucleic acid chip tests for the diagnosis and prognosis of diseases and for the development of therapeutic agents to treat such diseases.

The present invention also comprises devices comprising microarrays with specific sequence identifying probes that can be used to diagnose or prognose the specific change in the biological system. Once the learning machine of the present invention has identified specific relationships among the data that are capable of diagnosing or prognosing a change in a biological system, specific devices then incorporate tests for those specific relationships. For example, the learning machine of the present invention identifies specific genes that are related to the presence or future occurrence of a change in a biological system, such as the presence or appearance of a tumor. Knowing the sequence of these genes allows for the making of a specific treating device for those identified genes. For example, a nucleic acid chip, comprising DNA, RNA or specific binding proteins, or any such combination, that specifically binds to specifically identified genes is used to easily identify individuals having a particular tumor or the likelihood of developing the tumor. Additionally, specific proteins, either identified by the learning machine or that are associated with the genes identified by the learning machine, can be tested for using serological tests directed to specifically detecting the identified proteins, gene products or antibodies or antibody fragments directed to the proteins or gene products. Such tests include, but are not limited to, antibody nicroarrays on chips, Western blotting tests, ELISA, and other tests known in the art wherein binding between specific binding partners is used for detection of one of the partners.

Furthermore, the present invention comprises methods and compositions for treating the conditions resulting from changes in biological systems or for treating the biological system to alter the biological system to prevent or enhance specific conditions. For example, if the diagnosis of an individual includes the detection of a tumor, the individual can be treated with anti-tumor medications such as chemotherapeutic compositions. If the diagnosis of an individual includes the predisposition or prognosis of tumor development, the individual may be treated prophalactically with chemotherapeutic compositions to prevent the occurrence of the tumor. If specific genes are identified with the occurrence of tumors, the individual may be treated with specific antisense or other gene therapy methods to suppress the expression of such genes. Additionally, if specific genes or gene products are identified with the occurrence of tumors, then specific compositions that inhibit or functionally effect the genes or gene products are administered to the individual. The instances described herein are merely exemplary and are not to be construed as limiting the scope of the invention.

Proteomic investigations provide for methods of determining the proteins involved in normal and pathological states. Current methods of determining the proteome of a person or a population at any particular time or stage comprise the use of gel electrophoresis to separate the proteins in a sample. Preferably, 2-D gel electrophoresis is used to separate the proteins more completely. Additionally, the sample may be preprocessed to remove known proteins. The proteins may be labeled, for example, with fluorescent dyes, to aid in the determination of the patterns generated by the selected proteome. Patterns of separated proteins can be analyzed using the learning machines of the present invention. Capturing the gel image can be accomplished by image technology methods known in the art such as densitometry, CCD camera and laser scanning and storage phosphor instruments. Analysis of the gels reveals patterns in the proteome that are important in diagnosis and prognosis of pathological states and shows changes in relation to therapeutic interventions.

Further steps of investigating proteomes involve isolation of proteins at specific sites in the gels. Robotic systems for isolating specific sites are currently available. Isolation is followed by determination of the sequence and thus, the identity of the proteins. Studying the proteome of individuals or a population involves the generation, capture, analysis and integration of an enormous amount of data. Automation is currently being used to help manage the physical manipulations needed for the data generation. The learning machines of the present invention are used to analyze the biological data generated and to provide the information desired.

Additionally, using modifications of detection devices, such as chip detection devices, large libraries of biological data can be generated. Methods for generating libraries include technologies that use proteins covalently linked to their mRNA to determine the proteins made, for example, as rarely translated proteins. Such a technology comprises translating mRNA in vitro and covalently attaching the translated protein to the mRNA. The sequence of the mRNA and thus the protein is then determined using amplification methods such as PCR. Libraries containing $10^{14}$ to $10^{15}$ members can be established from this data. These libraries can be used to determine peptides that bind receptors or antibody libraries can be developed that contain antibodies that avidly bind their targets.

Libraries called protein domain libraries can be created from cellular mRNA where the entire proteins are not translated, but fragments are sequenced. These libraries can be used to determine protein function.

Other methods of investigating the proteome do not use gel electrophoresis. For example, mass spectrophotometry can be used to catalog changes in protein profiles and to define nucleic acid expression in normal or diseased tissues or in infectious agents to identify and validate drug and diagnostic targets. Analysis of this data is accomplished by the methods, systems and devices of the present invention. Further, technologies such as 2-hybrid and 2+1 hybrid systems that use proteins to capture the proteins with which they interact, currently found in yeast and bacterial systems, generate genome-wide protein interaction maps (PIMs). Large libraries of information such as PIMs can be manipulated by the present invention.

Antibody chips have been developed that can be used to separate or identify specific proteins or types of proteins. Additionally, phage antibody libaries can be used to determine protein function. Genomic libraries can be searched for open reading frames (ORFS) or ESTs (expressed sequence tags) of interest and from the sequence, peptides are synthesized. Peptides for different genes are placed in 96 well trays for selection of antibodies from phage libraries. The antibodies are then used to locate the protein relating to the original ORFs or ESTs in sections of normal and diseased tissue.

The present invention can be used to analyze biological data generated at multiple stages of investigation into biological functions, and further, to integrate the different kinds of data for novel diagnostic and prognostic determinations. For example, biological data obtained from clinical case information, such as diagnostic test data, family or genetic histories, prior or current medical treatments, and the clinical outcomes of such activities, can be utilized in the methods, systems and devices of the present invention. Additionally, clinical samples such as diseased tissues or fluids, and normal tissues and fluids, and cell separations can provide biological data that can be utilized by the current invention. Proteomic determinations such as 2-D gel, mass spectrophotometry and antibody screening can be used to establish databases that can be utilized by the present invention. Genomic databases can also be used alone or in combination with the above-described data and databases by the present invention to provide comprehensive diagnosis, prognosis or predictive capabilities to the user of the present invention.

A first aspect of the present invention seeks to enhance knowledge discovery by optionally pre-processing data prior to using the data to train a learning machine and/or optionally post-processing the output from a learning machine. Generally stated, pre-processing data comprises reformatting or augmenting the data in order to allow the learning machine to be applied most advantageously. Similarly, post-processing involves interpreting the output of a learning machine in order to discover meaningful characteristics thereof. The meaningful characteristics to be ascertained from the output may be problem or data specific. Post-processing involves interpreting the output into a form that is comprehendible by a human or one that is comprehendible by a computer.

Exemplary embodiments of the present invention will hereinafter be described with reference to the drawing, in which like numerals indicate like elements throughout the several figures. FIG. 1 is a flowchart illustrating a general method 100 for enhancing knowledge discovery using learning machines. The method 100 begins at starting block 101 and progresses to step 102 where a specific problem is formalized for application of knowledge discovery through machine learning. Particularly important is a proper formulation of the desired output of the learning machine. For instance, in predicting future performance of an individual equity instrument, or a market index, a learning machine is likely to achieve better performance when predicting the expected future change rather than predicting the future price level. The future price expectation can later be derived in a post-processing step as will be discussed later in this specification.

After problem formalization, step 103 addresses training data collection. Training data comprises a set of data points having known characteristics. Training data may be collected from one or more local and/or remote sources. The collection of training data may be accomplished manually or by way of an automated process, such as known electronic data transfer methods. Accordingly, an, exemplary embodiment of the present invention may be implemented in a networked computer environment. Exemplary operating environments for implementing various embodiments of the present invention will be described in detail with respect to FIGS. 10–12.

Next, at step 104 the collected training data is optionally pre-processed in order to allow the learning machine to be applied most advantageously toward extraction of the knowledge inherent to the training data. During this preprocessing stage the training data can optionally be expanded through transformations, combinations or manipulation of individual or multiple measures within the records of the training data. As used herein, expanding data is meant to refer to altering the dimensionality of the input data by changing the number of observations available to determine each input point (alternatively, this could be described as adding or deleting columns within a database table). By way of illustration, a data point may comprise the coordinates (1,4,9). An expanded version of this data point may result in the coordinates (1,1,4,2,9,3). In this example, it may be seen that the coordinates added to the expanded data point are based on a square-root transformation of the original coordinates. By adding dimensionality to the data point, this expanded data point provides a varied representation of the input data that is potentially more meaningful for knowledge discovery by a learning machine. Data expansion in this sense affords opportunities for learning machines to discover knowledge not readily apparent in the unexpanded training data.

Expanding data may comprise applying any type of meaningful transformation to the data and adding those transformations to the original data. The criteria for determining whether a transformation is meaningful may depend on the input data itself and/or the type of knowledge that is sought from the data. Illustrative types of data transformations include: addition of expert information; labeling; binary conversion; sine, cosine, tangent, cotangent, and other trigonometric transformation; clustering; scaling; probabilistic and statistical analysis; significance testing; strength testing; searching for 2-D regularities; Hidden Markov Modeling; identification of equivalence relations; application of contingency tables; application of graph theory principles; creation of vector maps; addition, subtraction, multiplication, division, application of polynomial equations and other algebraic transformations; identification of proportionality; determination of discriminatory power; etc. In the context of medical data, potentially meaningful transformations include: association with known standard medical reference ranges; physiologic truncation; physiologic combinations; biochemical combinations; application of heuristic rules; diagnostic criteria determinations; clinical weighting systems; diagnostic transformations; clinical transformations; application of expert knowledge; labeling techniques; application of other domain knowledge; Bayesian network knowledge; etc. These and other transformations, as well as combinations thereof, will occur to those of ordinary skill in the art.

Those skilled in the art should also recognize that data transformations may be performed without adding dimensionality to the data points. For example a data point may comprise the coordinate (A, B, C). A transformed version of this data point may result in the coordinates (1, 2, 3), where the coordinate "1" has some known relationship with the coordinate "A," the coordinate "2" has some known relationship with the coordinate "B," and the coordinate "3" has some known relationship with the coordinate "C." A transformation from letters to numbers may be required, for example, if letters are not understood by a learning machine. Other types of transformations are possible without adding dimensionality to the data points, even with respect to data that is originally in numeric form. Furthermore, it should be appreciated that pre-processing data to add meaning thereto may involve analyzing incomplete, corrupted or otherwise "dirty" data. A learning machine cannot process "dirty" data in a meaningful manner. Thus, a pre-processing step may involve cleaning up a data set in order to remove, repair or replace dirty data points.

Returning to FIG. 1, the exemplary method 100 continues at step 106, where the learning machine is trained using the pre-processed data. As is known in the art, a learning machine is trained by adjusting its operating parameters until a desirable training output is achieved. The determination of whether a training output is desirable may be accomplished either manually or automatically by comparing the training output to the known characteristics of the training data. A learning machine is considered to be trained when its training output is within a predetermined error threshold from the known characteristics of the training data. In certain situations, it may be desirable, if not necessary, to post-process the training output of the learning machine at step 107. As mentioned, post-processing the output of a learning machine involves interpreting the output into a meaningful form. In the context of a regression problem, for example, it may be necessary to determine range categorizations for the output of a learning machine in order to determine if the input data points were correctly categorized. In the example of a pattern recognition problem, it is often not necessary to post-process the training output of a learning machine.

At step 108, test data is optionally collected in preparation for testing the trained learning machine. Test data may be collected from one or more local and/or remote sources. In practice, test data and training data may be collected from the same source(s) at the same time. Thus, test data and training data sets can be divided out of a common data set and stored in a local storage medium for use as different input data sets for a learning machine. Regardless of how the test data is collected, any test data used must be pre-processed at step 110 in the same manner as was the training data. As should be apparent to those skilled in the art, a proper test of the learning may only be accomplished by using testing data of the same format as the training data. Then, at step 112 the learning machine is tested using the pre-processed test data, if any. The test output of the learning machine is optionally post-processed at step 114 in order to determine if the results are desirable. Again, the post processing step involves interpreting the test output into a meaningful form. The meaningful form may be one that is comprehendible by a human or one that is comprehendible by a computer. Regardless, the test output must be post-processed into a form which may be compared to the test data to determine whether the results were desirable. Examples of post-processing steps include but are not limited of the following: optimal categorization determinations, scaling techniques (linear and non-linear), transformations (linear and non-linear), and probability estimations. The method 100 ends at step 116.

Figure 2:
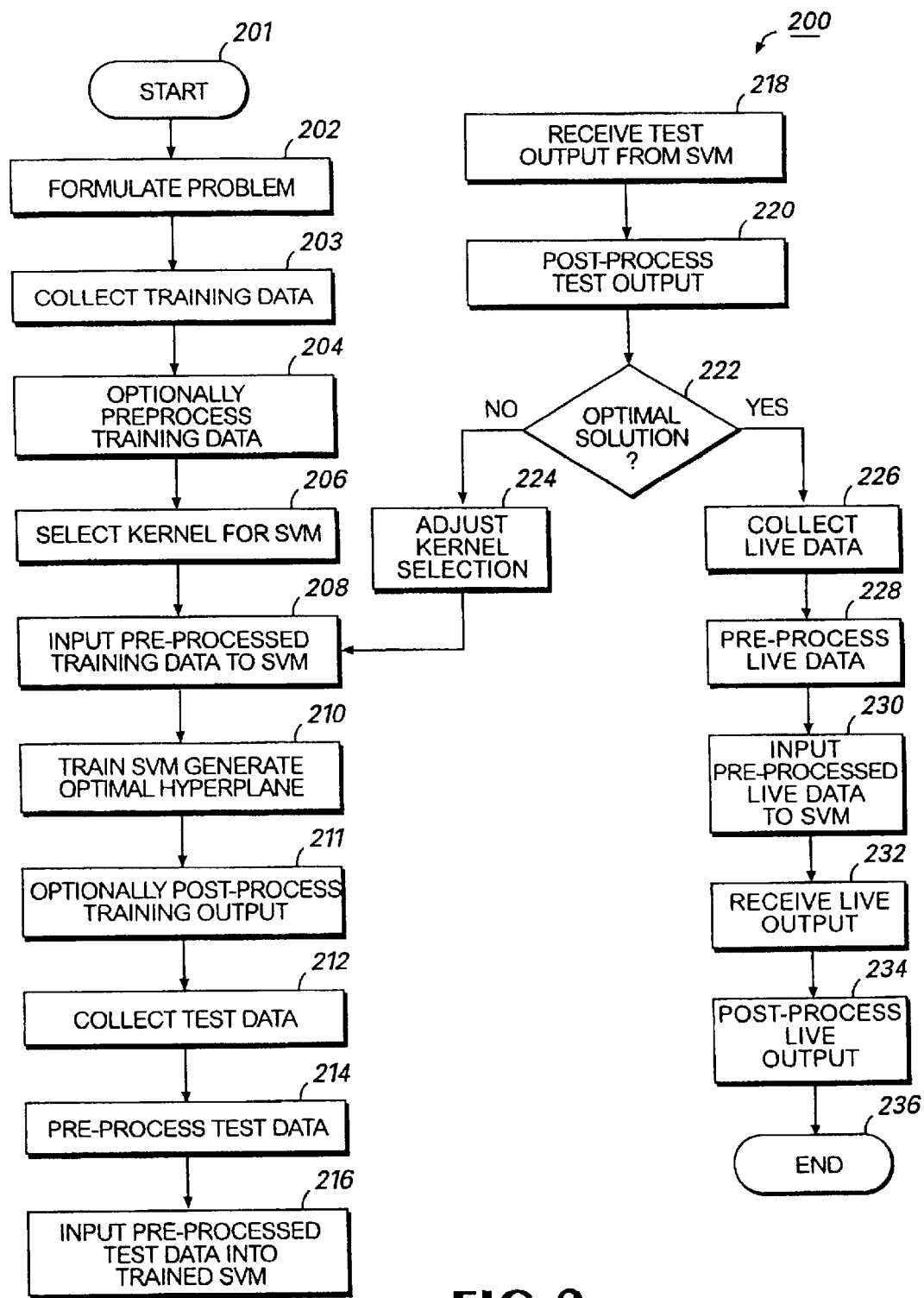
FIG. 2 is a flowchart illustrating an exemplary method for increasing knowledge that may be discovered from data using a support vector machine.

FIG. 2 is a flow chart illustrating an exemplary method 200 for enhancing knowledge that may be discovered from data using a specific type of learning machine known as a support vector machine (SVM). An SVM implements a specialized algorithm for providing generalization when estimating a multi-dimensional function from a limited collection of data. An SVM may be particularly useful in solving dependency estimation problems. More specifically, an SVM may be used accurately in estimating indicator functions (e.g. pattern recognition problems) and real-valued functions (e.g. function approximation problems, regression estimation problems, density estimation problems, and solving inverse problems). The concepts underlying the SVM are explained in detail in a book by Vladimir N. Vapnikv, entitled *Statistical Learning Theory* (John Wiley & Sons, Inc. 1998), which is herein incorporated by reference in its entirety. Accordingly, a familiarity with SVMs and the terminology used therewith are presumed throughout this specification.

Support vector machines were introduced in 1992 and the "kernel trick" was described. See Boser, B, et al., in Fifth Annal Workshop on Computational Learning Theory, p 144–152, Pittsburgh, ACM which is herein A training algorithm that maximizes the margin between the training patterns and the decision boundary was presented. The techniques was applicable to a wide variety of classification functions, including Perceptrons, polynomials, and Radial Basis Functions. The effective number of parameters was adjusted automaticaly to match the complexity of the problem. The solution was expressed as alinear combination of supporting patterns. These are the subset of training patterns that are closest to the decision boundary. Bounds on the generalization performance based on the leave-one-out method and the VC-dimension are given. Experimental results on optical character recognition problems demonstrate the good generalization obtained when compared with other learning algorithms.

A pattern recognition system using support vectors was disclosed in U.S. Pat. No. 5,649,068, which is herein incorporated in its entirety. A method is described in the patent wherein the dual representation mathematical principle was used for the design of decision systems. This principle permits some decision functions that are weighted sums of predefined functions to be represented as memory-based decision function. Using this principle, a memory-based decision system with optimum margin was designed wherein weights and prototypes of training patterns of a memory-based decision function were determined such that the corresponding dual decision function satisfies the criterion of margin optimality.

The exemplary method 200 begins at starting block 201 and advances to step 202, where a problem is formulated and then to step 203, where a training data set is collected. As was described with reference to FIG. 1, training data may be collected from one or more local and/or remote sources, through a manual or automated process. At step 204 the training data is optionally pre-processed. Again, pre-processing data comprises enhancing meaning within the training data by cleaning the data, transforming the data and/or expanding the data. Those skilled in the art should appreciate that SVMs are capable of processing input data having extremely large dimensionality. In fact, the larger the dimensionality of the input data, the better generalizations an SVM is able to calculate. Though merely increasing the dimensionality of the input space through preprocessing does not guarantee better generalization with an SVM. However, intelligent preprocessing that substantially increase input space dimensionality can be sucessfully modeled with an SVM unlike neural networks and traditional statistical models. The ability to handle higher dimensional data can often lead to better, more generalized models. Therefore, while training data transformations are possible that do not expand the training data, in the specific context of SVMs it is preferable that training data be expanded by adding meaningful information thereto.

At step 206 a kernel is selected for the SVM. As is known in the art, different kernels will cause an SVM to produce varying degrees of quality in the output for a given set of input data. Therefore, the selection of an appropriate kernel may be essential to the desired quality of the output of the SVM. In one embodiment of the present invention, a kernel may be chosen based on prior performance knowledge. As is known in the art, exemplary kernels include polynomial kernels, radial basis function kernels, linear kernels, etc. In an alternate embodiment, a customized kernel may be created that is specific to a particular problem or type of data set. In yet another embodiment, the multiple SVMs may be trained and tested simultaneously, each using a different kernel. The quality of the outputs for each simultaneously trained and tested SVM may be compared using a variety of selectable or weighted metrics (see step 222) to determine the most desirable kernel.

Next, at step 208 the pre-processed training data is input into the SVM. At step 210, the SVM is trained using the pre-processed training data to generate an optimal hyperplane. Optionally, the training output of the SVM may then be post-processed at step 211. Again, post-processing of training output may be desirable, or even necessary, at this point in order to properly calculate ranges or categories for the output. At step 212 test data is collected similarly to previous descriptions of data collection. The test data is pre-processed at step 214 in the same manner as was the training data above. Then, at step 216 the pre-processed test data is input into the SVM for processing in order to determine whether the SVM was trained in a desirable manner. The test output is received from the SVM at step 218 and is optionally post-processed at step 220.

Based on the post-processed test output, it is determined at step 222 whether an optimal minimum was achieved by the SVM. Those skilled in the art should appreciate that an SVM is operable to ascertain an output having a global minimum error. However, as mentioned above output results of an SVM for a given data set will typically vary in relation to the selection of a kernel. Therefore, there are in fact multiple global minimums that may be ascertained by an SVM for a given set of data. As used herein, the term "optimal minimum" or "optimal solution" refers to a selected global minimum that is considered to be optimal (e.g. the optimal solution for a given set of problem specific, pre-established criteria) when compared to other global minimums ascertained by an SVM. Accordingly, at step 222 determining whether the optimal minimum has been ascertained may involve comparing the output of an SVM with a historical or predetermined value. Such a predetermined value may be dependant on the test data set. For example, in the context of a pattern recognition problem where data points are classified by an SVM as either having a certain characteristic or not having the characteristic, a global minimum error of 50% would not be optimal. In this example, a global minimum of 50% is no better than the result that would be achieved by chance. As another example, in the case where multiple SVMs are trained and tested simultaneously with varying kernels, the outputs for each SVM may be compared with each other SVM's outputs to determine the practical optimal solution for that particular set of kernels. The determination of whether an optimal solution has been ascertained may be performed manually or through an automated comparison process.

If it is determined that the optimal minimum has not been achieved by the trained SVM, the method advances to step 224, where the kernel selection is adjusted. Adjustment of the kernel selection may comprise selecting one or more new kernels or adjusting kernel parameters. Furthermore, in the case where multiple SVMs were trained and tested simultaneously, selected kernels may be replaced or modified while other kernels may be re-used for control purposes. After the kernel selection is adjusted, the method 200 is repeated from step 208, where the previously pre-processed training data is input into the SVM for training purposes. When it is determined at step 222 that the optimal minimum has been achieved, the method advances to step 226, where live data is collected similarly as described above. The desired output characteristics that were known with respect to the training data and the test data are not known with respect to the live data.

At step 228 the live data is pre-processed in the same manner as was the training data and the test data. At step 230, the live pre-processed data is input into the SVM for processing. The live output of the SVM is received at step 232 and is post-processed at step 234. In one embodiment of the present invention, post-processing comprises converting the output of the SVM into a computationally derived alpha-numerical classifier, for interpretation by a human or computer. Preferably, the alphanumerical classifier comprises a single value that is easily comprehended by the human or computer. The method 200 ends at step 236.

Figure 3:
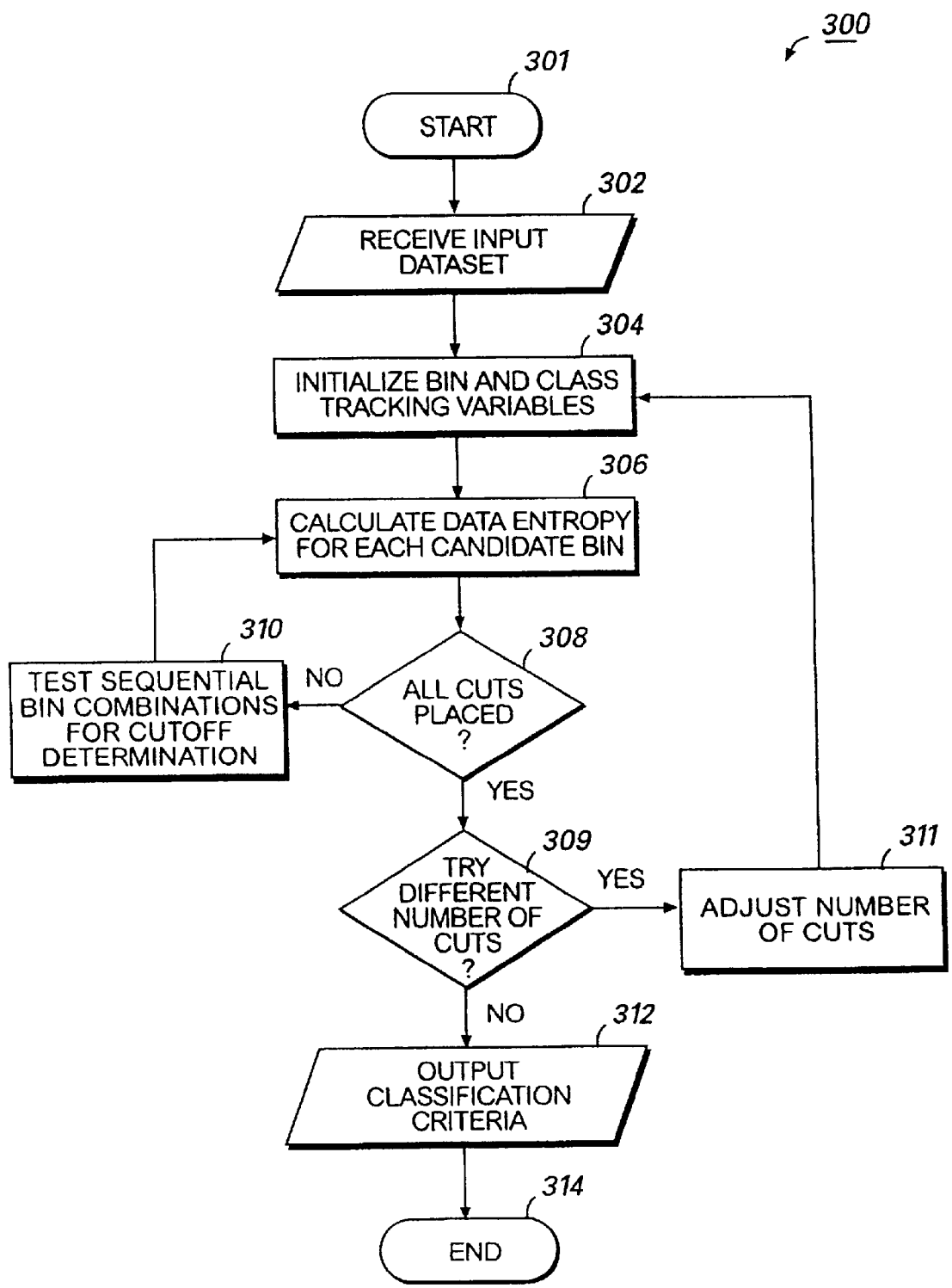
FIG. 3 is a flowchart illustrating an exemplary optimal categorization method that may be used in a stand-alone configuration or in conjunction with a learning machine for pre-processing or post-processing techniques in accordance with an exemplary embodiment of the present invention.

FIG. 3 is a flow chart illustrating an exemplary optimal categorization method 300 that may be used for pre-processing data or post-processing output from a learning machine in accordance with an exemplary embodiment of the present invention. Additionally, as will be described below, the exemplary optimal categorization method may be used as a stand-alone categorization technique, independent from learning machines. The exemplary optimal categorization method 300 begins at starting block 301 and progresses to step 302, where an input data set is received. The input data set comprises a sequence of data samples from a continuous variable. The data samples fall within two or more classification categories. Next, at step 304 the bin and class-tracking variables are initialized. As is known in the art, bin variables relate to resolution and class-tracking variables relate to the number of classifications within the data set. Determining the values for initialization of the bin and class-tracking variables may be performed manually or through an automated process, such as a computer program from analyzing the input data set. At step 306, the data entropy for each bin is calculated. Entropy is a mathematical quantity that measures the uncertainty of a random distribution. In the exemplary method 300, entropy is used to gauge the gradations of the input variable so that maximum classification capability is achieved.

The method 300 produces a series of "cuts" on the continuous variable, such that the continuous variable may be divided into discrete categories. The cuts selected by the exemplary method 300 are optimal in the sense that the average entropy of each resulting discrete category is minimized. At step 308, a determination is made as to whether all cuts have been placed within input data set comprising the continuous variable. If all cuts have not been placed, sequential bin combinations are tested for cutoff determination at step 310. From step 310, the exemplary method 300 loops back through step 306 and returns to step 308 where it is again determined whether all cuts have been placed within input data set comprising the continuous variable. When all cuts have been placed, the entropy for the entire system is evaluated at step 309 and compared to previous results from testing more or fewer cuts. If it cannot be concluded that a minimum entropy state has been determined, then other possible cut selections must be evaluated and the method proceeds to step 311. From step 311 a heretofore untested selection for number of cuts is chosen and the above process is repeated from step 304. When either the limits of the resolution determined by the bin width has been tested or the convergence to a minimum solution has been identified, the optimal classification criteria is output at step 312 and the exemplary optimal categorization method 300 ends at step 314.

The optimal categorization method 300 takes advantage of dynamic programming techniques. As is known in the art, dynamic programming techniques may be used to significantly improve the efficiency of solving certain complex problems through carefully structuring an algorithm to reduce redundant calculations. In the optimal categorization problem, the straightforward approach of exhaustively searching through all possible cuts in the continuous variable data would result in an algorithm of exponential complexity and would render the problem intractable for even moderate sized inputs. By taking advantage of the additive property of the target function, in this problem the average entropy, the problem may be divide into a series of sub-problems. By properly formulating algorithmic sub-structures for solving each sub-problem and storing the solutions of the sub-problems, a great amount of redundant computation may be identified and avoided. As a result of using the dynamic programming approach, the exemplary optimal categorization method 300 may be implemented as an algorithm having a polynomial complexity, which may be used to solve large sized problems.

As mentioned above, the exemplary optimal categorization method 300 may be used in pre-processing data and/or post-processing the output of a learning machine. For example, as a pre-processing transformation step, the exemplary optimal categorization method 300 may be used to extract classification information from raw data. As a post-processing technique, the exemplary optimal range categorization method may be used to determine the optimal cut-off values for markers objectively based on data, rather than relying on ad hoc approaches. As should be apparent, the exemplary optimal categorization method 300 has applications in pattern recognition, classification, regression problems, etc. The exemplary optimal categorization method 300 may also be used as a stand-alone categorization technique, independent from SVMs and other learning machines. An exemplary stand-alone application of the optimal categorization method 300 will be described with reference to FIG. 8.

FIG. 4 illustrates an exemplary unexpanded data set 400 that may be used as input for a support vector machine. This data set 400 is referred to as "unexpanded" because no additional information has been added thereto. As shown, the unexpanded data set comprises a training data set 402 and a test data set 404. Both the unexpanded training data set 402 and the unexpanded test data set 404 comprise data points, such as exemplary data point 406, relating to historical clinical data from sampled medical patients. The data set 400 may be used to train an SVM to determine whether a breast cancer patient will experience a recurrence or not.

Each data point includes five input coordinates, or dimensions, and an output classification shown as 406a–f which represent medical data collected for each patient. In particular, the first coordinate 406a represents "Age," the second coordinate 406b represents "Estrogen Receptor Level," the third coordinate 406c represents "Progesterone Receptor Level," the fourth coordinate 406d represents "Total Lymph Nodes Extracted," the fifth coordinate 406e represents "Positive (Cancerous) Lymph Nodes Extracted," and the output classification 406f, represents the "Recurrence Classification." The important known characteristic of the data 400 is the output classification 406f (Recurrence Classification), which, in this example, indicates whether the sampled medical patient responded to treatment favorably without recurrence of cancer ("−1") or responded to treatment negatively with recurrence of cancer ("1"). This known characteristic will be used for learning while processing the training data in the SVM, will be used in an evaluative fashion after the test data is input into the SVM thus creating a "blind" test, and will obviously be unknown in the live data of current medical patients.

FIG. 5 illustrates an exemplary test output 502 from an SVM trained with the unexpanded training data set 402 and tested with the unexpanded data set 404 shown in FIG. 4. The test output 502 has been post-processed to be comprehensible by a human or computer. As indicated, the test output 502 shows that 24 total samples (data points) were examined by the SVM and that the SVM incorrectly identified four of eight positive samples (50%) and incorrectly identified 6 of sixteen negative samples (37.5%).

FIG. 6 illustrates an exemplary expanded data set 600 that may be used as input for a support vector machine. This data set 600 is referred to as "expanded" because additional information has been added thereto. Note that aside from the added information, the expanded data set 600 is identical to the unexpanded data set 400 shown in FIG. 4. The additional information supplied to the expanded data set has been supplied using the exemplary optimal range categorization method 300 described with reference to FIG. 3. As shown, the expanded data set comprises a training data set 602 and a test data set 604. Both the expanded training data set 602 and the expanded test data set 604 comprise data points, such as exemplary data point 606, relating to historical data from sampled medical patients. Again, the data set 600 may be used to train an SVM to learn whether a breast cancer patient will experience a recurrence of the disease.

Through application of the exemplary optimal categorization method 300, each expanded data point includes twenty coordinates (or dimensions) $606a1$–$3$ through $606e1$–$3$, and an output classification $606f$, which collectively represent medical data and categorization transformations thereof for each patient. In particular, the first coordinate $606a$ represents "Age," the second coordinate through the fourth coordinate $606a1$–$606a3$ are variables that combine to represent a category of age. For example, a range of ages may be categorized, for example, into "young" "middle-aged" and "old" categories respective to the range of ages present in the data. As shown, a string of variables "0" ($606a1$), "0" ($606a2$), "1" ($606a3$) may be used to indicate that a certain age value is categorized as "old." Similarly, a string of variables "0" ($606a1$), "1" ($606a2$), "0" ($606a3$) may be used to indicate that a certain age value is categorized as "middle-aged." Also, a string of variables "1" ($606a1$), "0" ($606a2$), "0" ($606a1$) may be used to indicate that a certain age value is categorized as "young." From an inspection of FIG. 6, it may be seen that the optimal categorization of the range of "Age" $606a$ values, using the exemplary method 300, was determined to be 31–33= "young," 34="middle-aged" and 35–49 ="old." The other coordinates, namely coordinate 606b "Estrogen Receptors Level," coordinate 606c "Progesterone Receptor Level," coordinate 606d "Total Lymph Nodes Extracted," and coordinate 606e "Positive (Cancerous) Lymph Nodes Extracted," have each been optimally categorized in a similar manner.

FIG. 7 illustrates an exemplary expanded test output 702 from an SVM trained with the expanded training data set 602 and tested with the expanded data set 604 shown in FIG. 6. The expanded test output 702 has been post-processed to be comprehensible by a human or computer. As indicated, the expanded test output 702 shows that 24 total samples (data points) were examined by the SVM and that the SVM incorrectly identified four of eight positive samples (50%) and incorrectly identified four of sixteen negative samples (25%). Accordingly, by comparing this expanded test output 702 with the unexpanded test output 502 of FIG. 5, it may be seen that the expansion of the data points leads to improved results (i.e. a lower global minimum error), specifically a reduced instance of patients who would unnecessarily be subjected to follow-up cancer treatments.

FIG. 8 illustrates an exemplary input and output for a stand alone application of the optimal categorization method 300 described in FIG. 3. In the example of FIG. 8, the input data set 801 comprises a "Number of Positive Lymph Nodes" 802 and a corresponding "Recurrence Classification" 804. In this example, the optimal categorization method 300 has been applied to the input data set 801 in order to locate the optimal cutoff point for determination of treatment for cancer recurrence, based solely upon the number of positive lymph nodes collected in a post-surgical tissue sample. The well-known clinical standard is to prescribe treatment for any patient with at least three positive nodes. However, the optimal categorization method 300 demonstrates that the optimal cutoff 806, based upon the input data 801, should be at the higher value of 5.5 lymph nodes, which corresponds to a clinical rule prescribing follow-up treatments in patients with at least six positive lymph nodes.

As shown in the comparison table 808, the prior art accepted clinical cutoff point ($\geq 3.0$) resulted in 47% correctly classified recurrences and 71% correctly classified non-recurrences. Accordingly, 53% of the recurrences were incorrectly classified (further treatment was improperly not recommended) and 29% of the non-recurrences were incorrectly classified (further treatment was incorrectly recommended). By contrast, the cutoff point determined by the optimal categorization method 300 ($\geq 5.5$) resulted in 33% correctly classified recurrences and 97% correctly classified non-recurrences. Accordingly, 67% of the recurrences were incorrectly classified (further treatment was improperly not recommended) and 3% of the non-recurrences were incorrectly classified (further treatment was incorrectly recommended).

As shown by this example, it may be feasible to attain a higher instance of correctly identifying those patients who can avoid the post-surgical cancer treatment regimes, using the exemplary optimal categorization method 300. Even though the cutoff point determined by the optimal categorization method 300 yielded a moderately higher percentage of incorrectly classified recurrences, it yielded a significantly lower percentage of incorrectly classified non-recurrences. Thus, considering the trade-off, and realizing that the goal of the optimization problem was the avoidance of unnecessary treatment, the results of the cutoff point determined by the optimal categorization method 300 are mathematically superior to those of the prior art clinical cutoff point. This type of information is potentially extremely useful in providing additional insight to patients weighing the choice between undergoing treatments such as chemotherapy or risking a recurrence of breast cancer.

FIG. 9 is a comparison of exemplary post-processed output from a first support vector machine comprising a linear kernel and a second support vector machine comprising a polynomial kernel. FIG. 9 demonstrates that a variation in the selection of a kernel may affect the level of quality of the output of an SVM. As shown, the post-processed output of a first SVM 902 comprising a linear dot product kernel indicates that for a given test set of twenty-four samples, six of eight positive samples were incorrectly identified and three of sixteen negative samples were incorrectly identified. By way of comparison, the post-processed output for a second SVM 904 comprising a polynomial kernel indicates that for the same test set only two of eight positive samples were incorrectly identified and four of sixteen negative samples were identified. By way of comparison, the polynomial kernel yielded significantly improved results pertaining to the identification of positive samples and yielded only slightly worse results pertaining to the identification of negative samples. Thus, as will be apparent to those of skill in the art, the global minimum error for the polynomial kernel is lower than the global minimum error for the linear kernel for this data set.

Figure 10:
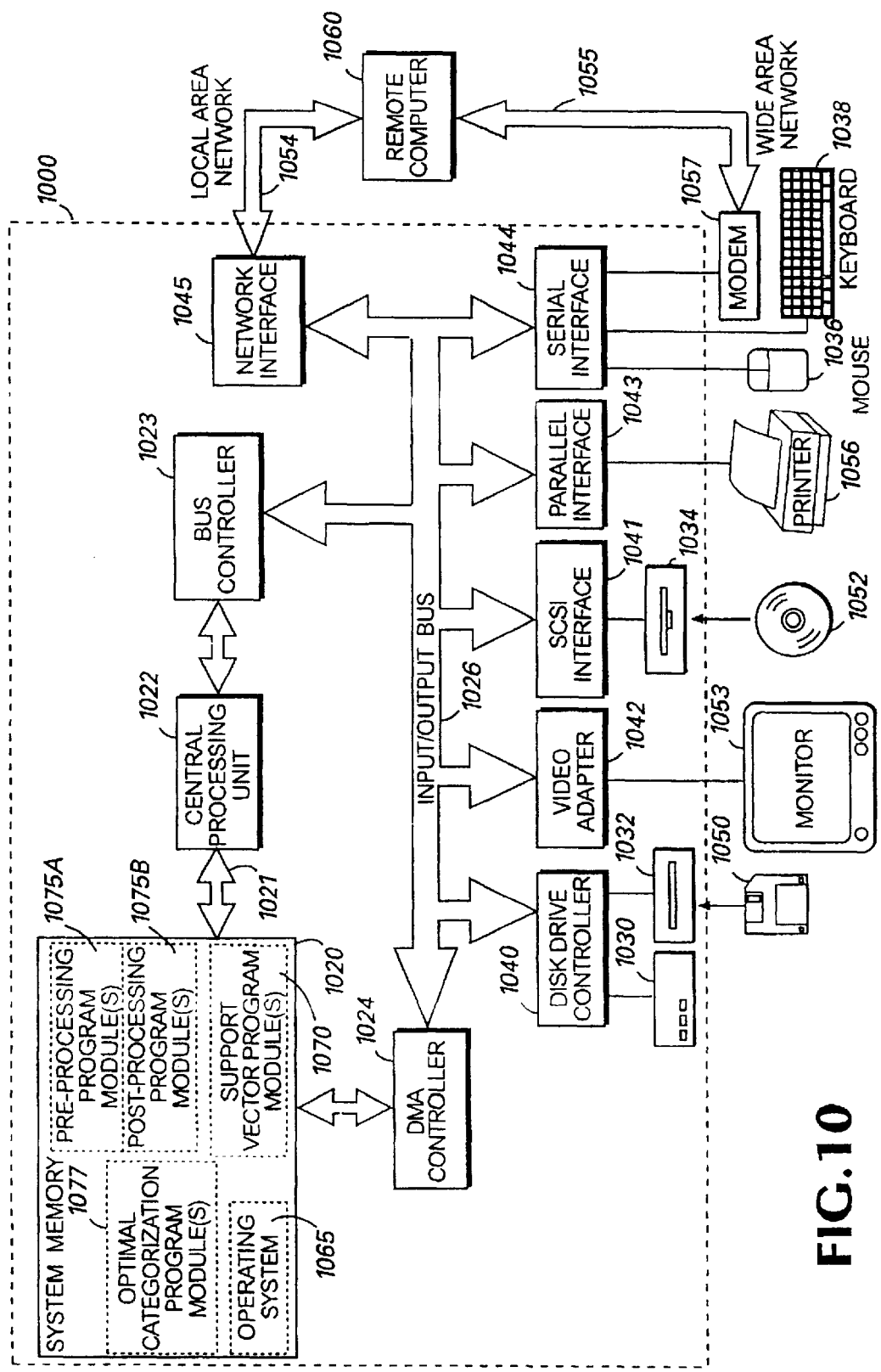
FIG. 10 is a functional block diagram illustrating an exemplary operating environment for an exemplary embodiment of the present invention.

FIG. 10 and the following discussion are intended to provide a brief and general description of a suitable computing environment for implementing the present invention. Although the system shown in FIG. 10 is a conventional personal computer 1000, those skilled in the art will recognize that the invention also may be implemented using other types of computer system configurations. The computer 1000 includes a central processing unit 1022, a system memory 1020, and an Input/Output ("I/O") bus 1026. A system bus 1021 couples the central processing unit 1022 to the system memory 1020. A bus controller 1023 controls the flow of data on the I/O bus 1026 and between the central processing unit 1022 and a variety of internal and external I/O devices. The I/O devices connected to the I/O bus 1026 may have direct access to the system memory 1020 using a Direct Memory Access ("DMA") controller 1024.

The I/O devices are connected to the I/O bus 1026 via a set of device interfaces. The device interfaces may include both hardware components and software components. For instance, a hard disk drive 1030 and a floppy disk drive 1032 for reading or writing removable media 1050 may be connected to the I/O bus 1026 through disk drive controllers 1040. An optical disk drive 1034 for reading or writing optical media 1052 may be connected to the I/O bus 1026 using a Small Computer System Interface ("SCSI") 1041. Alternatively, an IDE (ATAPI) or EIDE interface may be associated with an optical drive such as a may be the case with a CD-ROM drive. The drives and their associated computer-readable media provide nonvolatile storage for the computer 1000. In addition to the computer-readable media described above, other types of computer-readable media may also be used, such as ZIP drives, or the like.

A display device 1053, such as a monitor, is connected to the I/O bus 1026 via another interface, such as a video adapter 1042. A parallel interface 1043 connects synchronous peripheral devices, such as a laser printer 1056, to the I/O bus 1026. A serial interface 1044 connects communication devices to the I/O bus 1026. A user may enter commands and information into the computer 1000 via the serial interface 1044 or by using an input device, such as a keyboard 1038, a mouse 1036 or a modem 1057. Other peripheral devices (not shown) may also be connected to the computer 1000, such as audio input/output devices or image capture devices.

A number of program modules may be stored on the drives and in the system memory 1020. The system memory 1020 can include both Random Access Memory ("RAM") and Read Only Memory ("ROM"). The program modules control how the computer 1000 functions and interacts with the user, with I/O devices or with other computers. Program modules include routines, operating systems 1065, application programs, data structures, and other software or firmware components. In an illustrative embodiment, the present invention may comprise one or more pre-processing program modules 1075A, one or more post-processing program modules 1075B, and/or one or more optimal categorization program modules 1077 and one or more SVM program modules 1070 stored on the drives or in the system memory 1020 of the computer 1000. Specifically, pre-processing program modules 1075A, post-processing program modules 1075B, together with the SVM program modules 1070 may comprise computer-executable instructions for pre-processing data and post-processing output from a learning machine and implementing the learning algorithm according to the exemplary methods described with reference to FIGS. 1 and 2. Furthermore, optimal categorization program modules 1077 may comprise computer-executable instructions for optimally categorizing a data set according to the exemplary methods described with reference to FIG. 3.

The computer 1000 may operate in a networked environment using logical connections to one or more remote computers, such as remote computer 1060. The remote computer 1060 may be a server, a router, a peer device or other common network node, and typically includes many or all of the elements described in connection with the computer 1000. In a networked environment, program modules and data may be stored on the remote computer 1060. The logical connections depicted in FIG. 10 include a local area network ("LAN") 1054 and a wide area network ("WAN") 1055. In a LAN environment, a network interface 1045, such as an Ethernet adapter card, can be used to connect the computer 1000 to the remote computer 1060. In a WAN environment, the computer 1000 may use a telecommunications device, such as a modem 1057, to establish a connection. It will be appreciated that the network connections shown are illustrative and other devices of establishing a communications link between the computers may be used.

Figure 11:
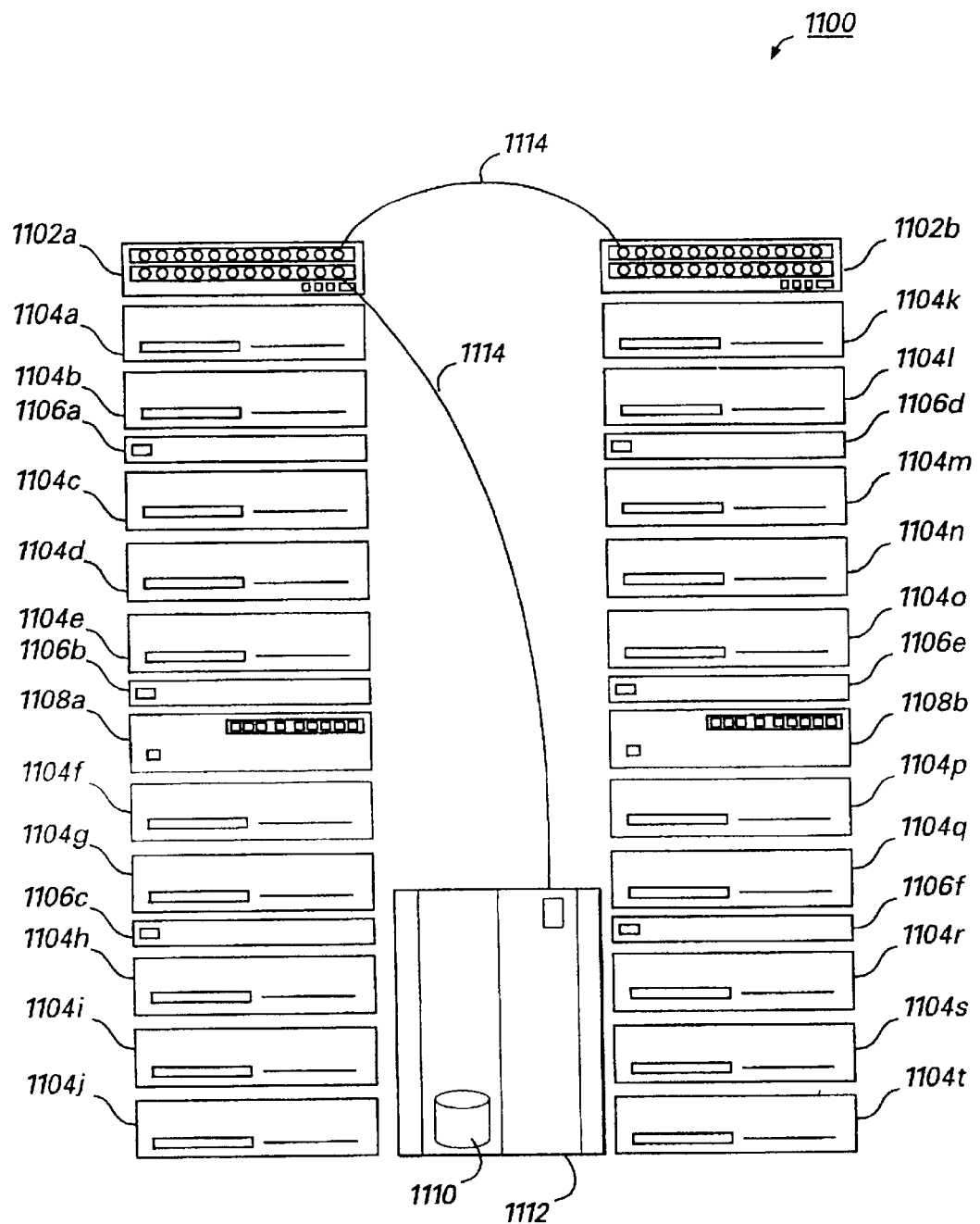
FIG. 11 is a functional block diagram illustrating an alternate exemplary operating environment for an alternate embodiment of the present invention.

FIG. 11 is a functional block diagram illustrating an alternate exemplary operating environment for implementation of the present invention. The present invention may be implemented in a specialized configuration of multiple computer systems. An example of a specialized configuration of multiple computer systems is referred to herein as the BIOWulf™ Support Vector Processor (BSVP). The BSVP combines the latest advances in parallel computing hardware technology with the latest mathematical advances in pattern recognition, regression estimation, and density estimation. While the combination of these technologies is a unique and novel implementation, the hardware configuration is based upon Beowulf supercomputer implementations pioneered by the NASA Goddard Space Flight Center.

The BSVP provides the massively parallel computational power necessary to expedite SVM training and evaluation on large-scale data sets. The BSVP includes a dual parallel hardware architecture and custom parallelized software to enable efficient utilization of both multithreading and message passing to efficiently identify support vectors in practical applications. Optimzation of both hardware and software enables the BSVP to significantly outperform typical SVM implementations. Furthermore, as commodity computing technology progresses the upgradability of the BSVP is ensured by its foundation in open source software and standardized interfacing technology. Future computing platforms and networking technology can be assimilated into the BSVP as they become cost effective with no effect on the software implementation.

As shown in FIG. 11, the BSVP comprises a Beowulf class supercomputing cluster with twenty processing nodes 1104a–t and one host node 1112. The processing nodes 1104a–j are interconnected via switch 1102a, while the processing nodes 1104k–t are interconnected via switch 1102b. Host node 1112 is connected to either one of the network switches 1102a or 1102b (1102a shown) via an appropriate Ethernet cable 1114. Also, switch 1102a and switch 1102b are connected to each other via an appropriate Ethernet cable 1114 so that all twenty processing nodes 1104a–t and the host node 1112 are effectively in communication with each other. Switches 1102a and 1102b preferably comprise Fast Ethernet interconnections. The dual parallel architecture of the BSVP is accomplished through implementation of the Beowulf supercomputer's message passing multiple machine parallel configuration and utilizing a high performance dual processor SMP computer as the host node 1112.

In this exemplary configuration, the host node 1112 contains glueless multi-processor SMP technology and consists of a dual 450 Mhz Pentium II Xeon based machine with 18 GB of Ultra SCSI storage, 256 MB memory, two 100 Mbit/sec NIC's, and a 24 GB DAT network backup tape device. The host node 1112 executes NIS, MPI and/or PVM under Linux® to manage the activity of the BSVP. The host node 1112 also provides the gateway between the BSVP and the outside world. As such, the internal network of the BSVP is isolated from outside interaction, which allows the entire cluster to appear to function as a single machine.

The twenty processing nodes 1104a–t are identically configured computers containing 150 MHz Pentium processors, 32 MB RAM, 850 MB HDD, 1.44 MB FDD, and a Fast Ethernet mb100 Mb/s NIC. The processing nodes 1104a–t are interconnected with each other and the host node through NFS connections over TCP/IP. In addition to BSVP computations, the processing nodes are configured to provide demonstration capabilities through an attached bank of monitors with each node's keyboard and mouse routed to a single keyboard device and a single mouse device through the KVM switches 1108a and 1108b.

Software customization and development allow optimization of activities on the BSVP. Concurrency in sections of SVM processes is exploited in the most advantageous manner through the hybrid parallelization provided by the BSVP hardware. The software implements full cycle support from raw data to implemented solution. A database engine provides the storage and flexibility required for pre-processing raw data. Custom developed routines automate the pre-processing of the data prior to SVM training. Multiple transformations and data manipulations are performed within the database environment to generate candidate training data.

The peak theoretical processing capability of the BSVP is 3.90GFLOPS. Based upon the benchmarks performed by NASA Goddard Space Flight Center on their Beowulf class machines, the expected actual performance should be about 1.56GFLOPS. Thus the performance attained using commodity component computing power in this Beowulf class cluster machine is in line with that of supercomputers such as the Cray J932/8. Further Beowulf testing at research and academic institutions indicates that a performance on the order of 18 times a single processor can generally be attained on a twenty node Beowulf cluster. For example, an optimization problem requiring 17 minutes and 45 seconds of clock time on a single Pentium processor computer was solved in 59 seconds on a Beowulf with 20 nodes. Therefore, the high performance nature of the BSVP enables practical analysis of data sets currently considered too cumbersome to handle by conventional computer systems.

The massive computing power of the BSVP renders it particularly useful for implementing multiple SVMs in parallel to solve real-life problems that involve a vast number of inputs. Examples of the usefulness of SVMs in general and the BSVP in particular comprise: genetic research, in particular the Human Genome Project; evaluation of managed care efficiency; therapeutic decisions and follow up; appropriate therapeutic triage; pharmaceutical development techniques; discovery of molecular structures; prognostic evaluations; medical informatics; billing fraud detection; inventory control; stock evaluations and predictions; commodity evaluations and predictions; and insurance probability estimates.

Those skilled in the art should appreciate that the BSVP architecture described above is illustrative in nature and is not meant to limit the scope of the present invention. For example, the choice of twenty processing nodes was based on the well known Beowulf architecture. However, the BSVP may alternately be implemented using more or less than twenty processing nodes. Furthermore the specific hardware and software components recited above are by way of example only. As mentioned, the BSVP embodiment of the present invention is configured to be compatible with alternate and/or future hardware and software components.

Figure 12:
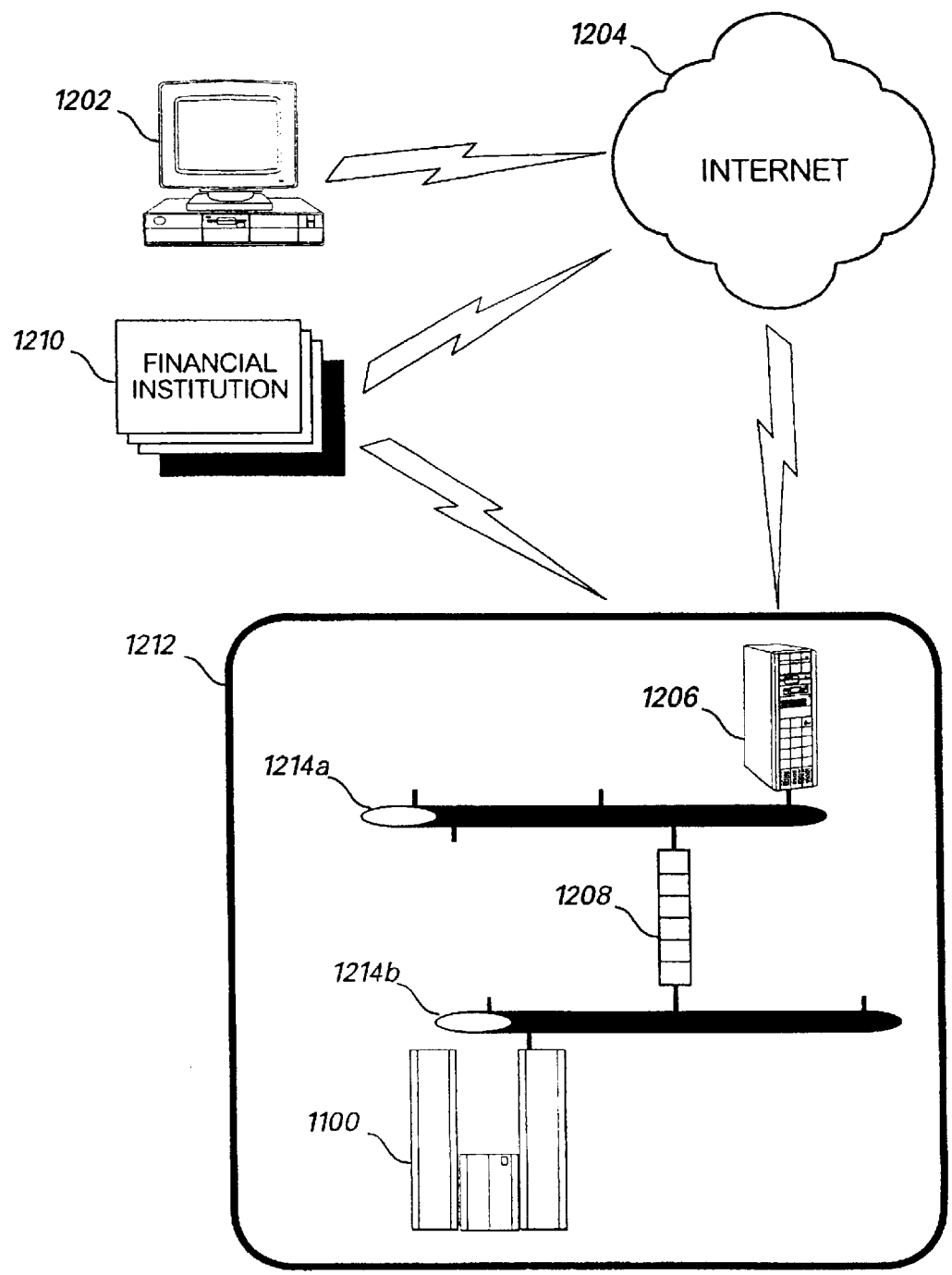
FIG. 12 is a functional block diagram illustrating an exemplary network operating environment for implementation of a further alternate embodiment of the present invention.
Figure 13A:
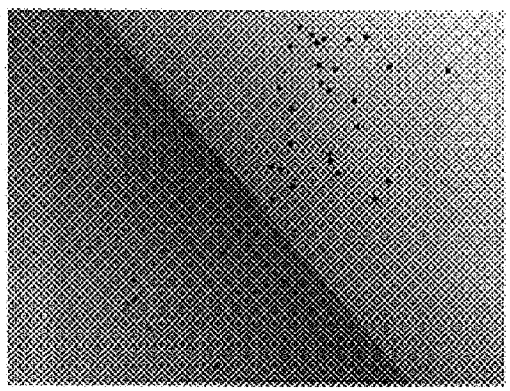
FIGS. 13A, 13B, 13C and 13D graphically illustrate use of a linear discriminant classifier 13A) Separation of the training examples with an SVM. 13B) Separation of the training and test examples with the same SVM. 13C) Separation of the training examples with the baseline method. 13D) Separation of the training and test examples with the baseline method.
Figure 13B:
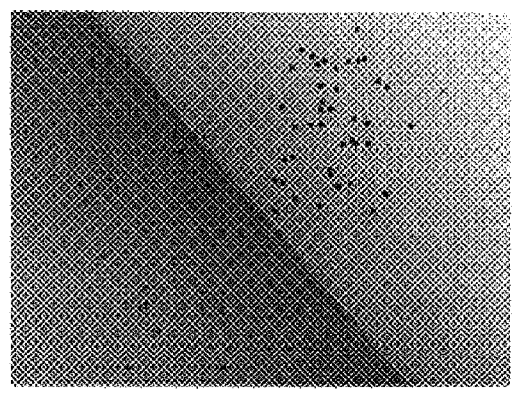
Figure 13C:
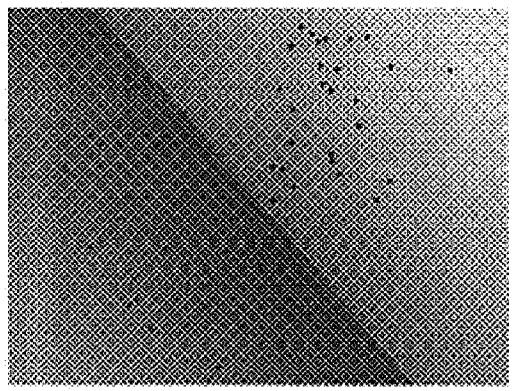
Figure 13D:
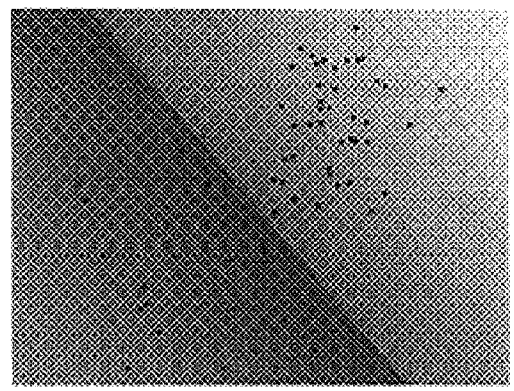

FIG. 12 is a functional block diagram illustrating an exemplary network operating environment for implementation of a further alternate embodiment of the present invention. In the exemplary network operating environment, a customer 1202 or other entity may transmit data via a distributed computer network, such as the Internet 1204, to a vendor 1212. Those skilled in the art should appreciate that the customer 1202 may transmit data from any type of computer or lab instrument that includes or is in communication with a communications device and a data storage device. The data transmitted from the customer 1202 may be training data, test data and/or live data to be processed by a learning machine. The data transmitted by the customer is received at the vendor's web server, 1206, which may transmit the data to one or more learning machines via an internal network 1214*a–b*. As previously described, learning machines may comprise SVMs, BSVPs 1100, neural networks, other learning machines or combinations thereof. Preferable, the web server 1206 is isolated from the learning machine(s) by way of a firewall 1208 or other security system. The vendor 1212 may also be in communication with one or more financial institutions 1210, via the Internet 1204 or any dedicated or on-demand communications link. The web server 1206 or other communications device may handle communications with the one or more financial institutions. The financial institution(s) may comprise banks, Internet banks, clearing houses, credit or debit card companies, or the like.

In operation, the vendor may offer learning machine processing services via a web-site hosted at the web-server 1206 or another server in communication with the web-server 1206. A customer 1202 may transmit data to the web server 1206 to be processed by a learning machine. The customer 1202 may also transmit identification information, such as a username, a password and/or a financial account identifier, to the web-server. In response to receiving the data and the identification information, the web server 1206 may electronically withdraw a pre-determined amount of funds from a financial account maintained or authorized by the customer 1202 at a financial institution 1210. In addition, the web server may transmit the customer's data to the BSVP 1100 or other learning machine. When the BSVP 1100 has completed processing of the data and post-processing of the output, the post-processed output is returned to the web-server 1206. As previously described, the output from a learning machine may be post-processed in order to generate a single-valued or multi-valued, computationally derived alpha-numerical classifier, for human or automated interpretation. The web server 1206 may then ensure that payment from the customer has been secured before the post-processed output is transmitted back to the customer 1202 via the Internet 1204.

SVMs may be used to solve a wide variety of real-life problems. For example, SVMs may have applicability in analyzing accounting and inventory data, stock and commodity market data, insurance data, medical data, etc. As such, the above-described network environment has wide applicability across many industries and market segments. In the context of inventory data analysis, for example, a customer may be a retailer. The retailer may supply inventory and audit data to the web server 1206 at predetermined times. The inventory and audit data may be processed by the BSVP and/or one or more other learning machine in order to evaluate the inventory requirements of the retailer. Similarly, in the context of medical data analysis, the customer may be a medical laboratory and may transmit live data collected from a patient to the web server 1206 while the patient is present in the medical laboratory. The output generated by processing the medical data with the BSVP or other learning machine may be transmitted back to the medical laboratory and presented to the patient.

A preferred embodiment of the methods, systems and devices of the present invention is herein described. As used herein, data input is a vector called a "pattern" of components called "features". In this embodiment, the features are gene expression coefficients and patterns correspond to patients. A two-class classification problem is shown. A training set of a number of patterns with known class labels was used. The training patterns were used to build a decision function or a discriminant function that is a scalar function of an input pattern. New patterns are classified according to the sign of the decision function. Decision functions that are simple weighted sums of the training patterns plus a bias are called linear discriminiant functions. A data set is said to be "linearly separable" if a linear discriminant function can separate it without error.

A known problem in classification, and machine learning in general, is to find means to reduce the dimensionality of input space to overcome the risk of "overfitting". Data overfitting arises when the number of features is large, such as the thousands of genes studied in a microarray and the number of training patterns is comparatively small, such as the few dozens of patients. In such situations, one can find a decision function that separates the training data, even a linear decision function, and yet performs poorly on test data. Training techniques that use regularization avoid over-fitting the data without requiring space dimensionality reduction. Such is the case, for instance, of Support Vector Machines (SVMs) though even SVMs can benefit from space dimensionality reduction.

Other methods of reduction include projecting on the first few principal directions of the data. With such method, new features are obtained that are linear combinations of the original features. One disadvantage of projection methods is that none of the original input features can be discarded. Preferred methods comprise pruning techniques that eliminate some of the original input features and retain a minimum subset of features that yield a better classification performance. For diagnostic tests, it is of practical importance to be able to select a small subset of genes for reasons such as cost effectiveness and so that the relevance of the genes selected can be verified more easily.

The problem of feature selection is well known in pattern recognition. Given a particular classification technique, one can select the best subset of features satisfying a given "model selection" criterion by exhaustive enumeration of all subsets of features. This method is impractical for large numbers of features, such as thousands of genes, because of the combinatorial explosion of the number of subsets.

Performing feature selection in large dimensional input spaces involves greedy algorithms. Among various possible methods, feature ranking techniques are particularly preferred. A fixed number of top ranked features may be selected for further analysis or to design a classifier. Alternatively, a threshold can be set on the ranking criterion. Only the features whose criterion exceed the threshold are retained. A preferred method is to use the ranking to define nested subsets of features and select an optimum subset of features with a model selection criterion by varying a single parameter: the number of features.

The present invention also comprises methods, systems and devices of multiple support vector machines for discovering knowledge from multiple data sets. The present invention contemplates that a plurality of support vector machines may be configured to hierarchically process multiple data sets in parallel or in sequence. In particular, one or more first-level support vector machines may be trained and tested to process a first type of data and one or more first-level support vector machines may be trained and tested to process a second type of data. Additional types of data may be processed by other first-level support vector machines as well. The output from some or all of the first-level support vector machines may be combined in a logical manner so as to produce an input data set for one or more second-level support vector machines. In a similar fashion, output from a plurality of second-level support vector machines may be combined in a logical manner to produce input data for one or more third-level support vector machine. The hierarchy of support vector machines may be expanded to any number of levels as may be appropriate.

Each support vector machine in the hierarchy or each hierarchical level of support vector machines may be configured with a distinct kernel. For example, support vector machines used to process a first type of data may be configured with a first type of kernel, whereas support vector machines used to process a second type of data may be configured with a second type of kernel. In addition, multiple support vector machines in the same or different hierarchical level may be configured to process the same type of data using distinct kernels.

In an example, presented for illustrative purposes only, a first-level support vector machine may be trained and tested to process mammography data pertaining to a sample of medical patients. An additional first-level support vector machine may be trained and tested to process genomic data for the same or a different sample of medical patients. The output from the two first-level support vector machines may be combined to form a new multi-dimensional data set relating to mammography and genomic data. The new data set may then be processed by an appropriately trained and tested second-level support vector machine. The resulting output from the second-level support vector machine may identify causal relationships between the mammography and genomic data points. As should be apparent to those of ordinary skill in the art, the contemplated hierarchy of support vector machines may have applications in any field or industry in which analysis of data by a learning machine is desired.

The hierarchical processing of multiple data sets using multiple support vector machines may be used as a method for pre-processing or post-processing data that is to be input to or output from still other support vector machines or learning machines. In addition, pre-processing or post-processing of data according to the methods described below may be performed to the input data and/or output of the above-described hierarchical architecture of support vector machines.

Figure 36:
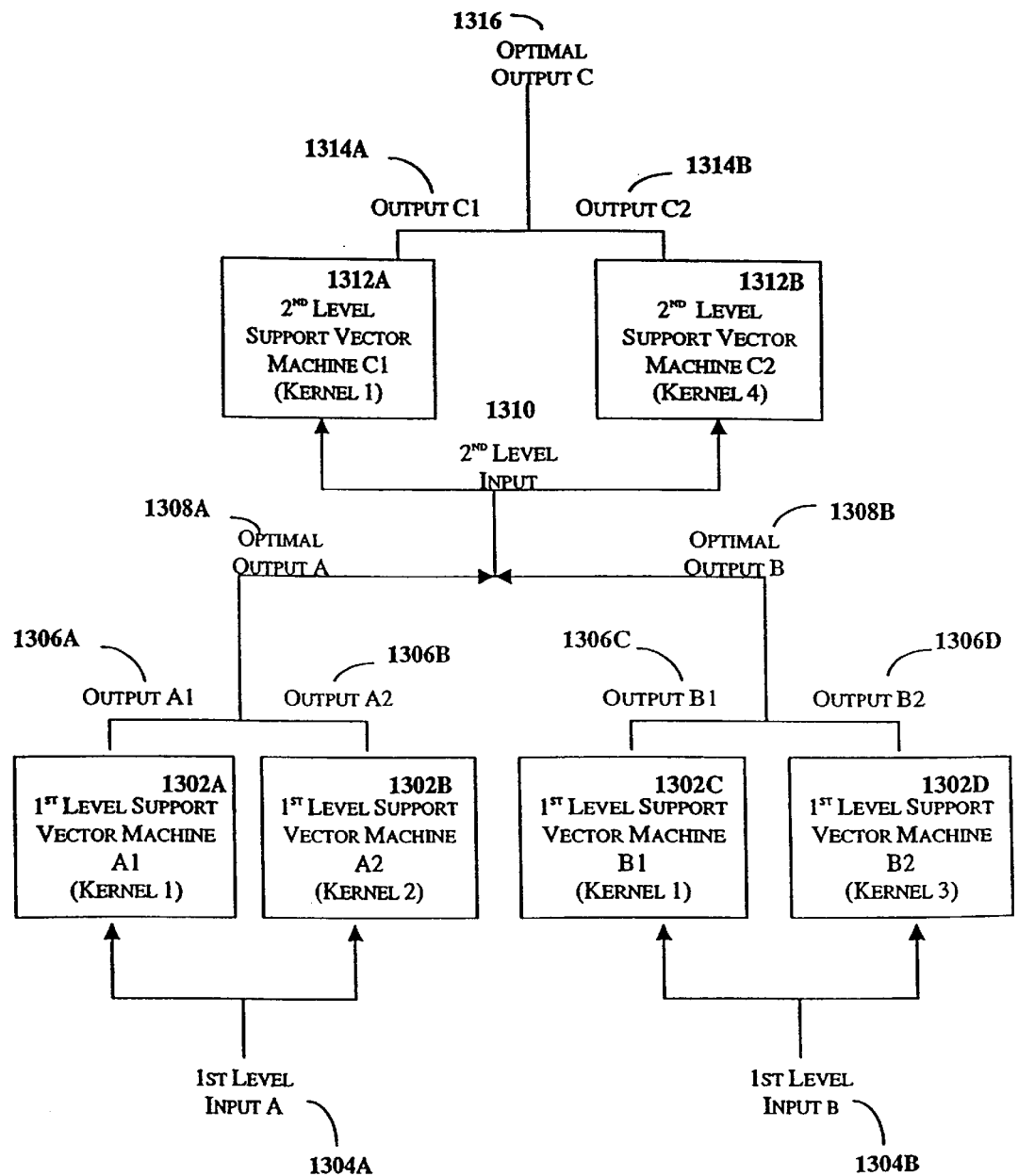
FIG. 36 is a functional block diagram illustrating a hierarchical system of multiple support vector machine.

FIG. 36 is presented by way of example only to illustrate a hierarchical system of support vector machines. As shown, one or more first-level support vector machines 1302A1 and 1302A2 may be trained and tested to process a first type of input data 1304A, such as mamography data, pertaining to a sample of medical patients. One or more of these support vector machines may comprise a distinct kernel (shown as kernel 1 and kernel 2). Also one or more additional first-level support vector machines 1302B1 and 1302B2 may be trained and tested to process a second type of data 1304B, such as genomic data, for the same or a different sample of medical patients. Again one or more of the additional support vector machines may comprise a distinct kernel (shown as kernel 1 and kernel 3). The output from each of the like first level support vector machines may be compared with each other (i.e., output A1 1306A compared with output A2 1306B; output B1 1306C compared with output B2 1306D) in order to determine optimal outputs (1308A and 1308B). Then, the optimal outputs from the two types of first-level support vector machines 1308A and 1308B may be combined to form a new multi-dimensional input data set 1310, for example relating to mamography and genomic data. The new data set may then be processed by one or more appropriately trained and tested second-level support vector machines 1312A and 1312B. The resulting outputs 1314A and 1314B from the second-level support vector machines 1312A and 1312B may be compared to determine an optimal output 1316. The optimal output 1316 may identify causal relationships between the mamography and genomic data points. As should be apparent to those of ordinary skill in the art, the contemplated hierarchy of support vector machines may have applications in any field or industry in which analysis of data by a learning machine is desired.

The hierarchical processing of multiple data sets using multiple support vector machines may be used as a method for pre-processing or post-processing data that is to be input to or output from still other support vector machines or learning machines. In addition, pre-processing or post-processing of data may be performed to the input data and/or output of the above-described hierarchical architecture of support vector machines.

The examples included herein show preferred methods for determining the genes that are most correlated to the presence of colon cancer or can be used to predict colon cancer occurance in an individual. The present invention comprises these methods, and other methods, including other computational methods, usable in a learning machine for determining genes, proteins or other measurable criteria for the diagnosis or prognosis of changes in a biological system. There is no limitation to the source of the data and the data can be combinations of measurable criteria, such as genes, proteins or clinical tests, that are capable of being used to differentiate between normal conditions and changes in conditions in biological systems.

In the following examples, preferred numbers of genes were determined. These numbers are not limiting to the methods of the present invention. Preferable, for colon cancer, the preferred optimum number of genes is a range of approximately from 1 to 100, more preferably, the range is from 1 to 50, even more preferably the range is from 1 to 32, still more preferably the range is from 1 to 21 and most preferably, from 1 to 10. The preferred optimum number of genes can be affected by the quality and quantity of the original data and thus can be determined for each application by those skilled in the art.

Once the determinative genes are found by the learning machines of the present invention, methods and compositions for treaments of the biological changes in the organisms can be employed. For example, for the treatment of colon cancer, therapeutic agents can be administered to antagonize or agonize, enhance or inhibit activities, presence, or synthesis of the gene products. Therapeutic agents include, but are not limited to, gene therapies such as sense or antisense polynucleotides, DNA or RNA analogs, pharmaceutical agents, plasmaphoresis, antiangiogenics, and derivatives, analogs and metabolic products of such agents.

Such agents are administered via parenteral or noninvasive routes. Many active agents are administered through parenteral routes of administration, intravenous, intramuscular, subcutaneous, intraperitoneal, intraspinal, intrathecal, intracerebroventricular, intraarterial and other routes of injection. Noninvasive routes for drug delivery include oral, nasal, pulmonary, rectal, buccal, vaginal, transdermal and occular routes.

Another embodiment of the present invention comprises use of testing remote from the site of determination of the patterns through means such as the internet or telephone lines. For example, a genomic test to identify the presence of genes known to be related to a specific medical condition is performed in a physician's office. Additionally, other information such as clinical data or proteomic determinations may also be made at the same time or a different time. The results of one, some or all of the tests are transmitted to a remote site that houses the SVMs. Such testing could be used for the diagnosis stages, for determining the prognosis of the disease, for determining the results of therapy and for prescriptive applications such as determining which therapy regimine is better for individual patients.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Analysis of Gene Patterns Related to Colon Cancer

Errorless separation can be achieved with any number of genes, from one to many. Preferred methods comprise use of larger numbers of genes. Classical gene selection methods select the genes that individually classify the training data best. These methods include correlation methods and expression ratio methods. They eliminate genes that are useless for discrimination (noise), but do not yield compact gene sets because genes are redundant. Moreover, complementary genes that individually do not separate well the data are missed.

A simple feature (gene) ranking can be produced by evaluating how well an individual feature contributes to the separation (e.g. cancer vs. normal). Various correlation coefficients are used as ranking criteria. The coefficient used is defined as:

$$P = (\mu_1 - \mu_2)/(\sigma_1 + \sigma_2)$$

where $\mu_i$ and $\sigma_i$ are the mean and standard deviation of the gene expression values of a particular gene for all the patients of class i, i=1 or 2. Large positive P values indicate strong correlation with class 1 whereas large negative P values indicate strong correlation with class 2.

What characterizes feature ranking with correlation methods is the implicit independence assumptions that are made. Each coefficient P is computed with information about a single feature (gene) and does not take into account mutual information between features.

One use of feature ranking is the design of a class predictor (or classifier) based on a pre-selected subset of genes. Each gene which is correlated (or anti-correlated) with the separation of interest is by itself such a class predictor, albeit an imperfect one. A simple method of classification based on weighted voting: the genes vote proportionally to their correlation coefficient. Such is the method used in Golub, 1999. The weighted voting scheme yields a classifier which is a particular linear discriminant classifier.

A preferred method for the present invention comprises using the gene ranking coefficients as classifier weights. Reciprocally, the weights multiplying the inputs of a given classifier can be used as gene ranking coefficients. The inputs that are weighted by the largest values have the most influence in the classification decision. Therefore, if the classifier performs well, those inputs with largest weights correspond to the most informative genes. Other methods comprise algorithms to train linear discriminant functions that provide a better gene ranking because they do not make any implicit independence assumption.

A preferred method of the present invention is to use the weights of a classifier to produce a feature ranking with an SVM (Support Vector Machine). The present invention contemplates methods of SVMs used for non-linear decision boundaries of arbitrary complexity, though the example provided here is directed to linear SVMs because of the nature of the data set under investigation. FIG. 13A, 13B, 13C and 13D graphically illustrate use of a linear discriminant classifier. In this example, the x and y coordinates represent the expression coefficients of two genes. A linear discriminant classifier makes its decision according to the sign of a weighted sum of the x and y inputs plus a bias value. There exist many methods to choose appropriate weights, using training examples. If the training data set is linearly separable, SVMs are maximum margin classifiers in their input components. See FIG. 13A and 13B. The decision boundary (a straight line in the case of a two-dimensional separation) is positioned to leave the largest possible margin on either side. A particularity of SVMs is that the weights of the decision function are a function only of a small subset of the training examples, called "'support vectors". Those are the examples that are closest to the decision boundary and lie on the margin. The existence of such support vectors is at the origin of the computational properties of SVM and their competitive classification performance. While SVMs base their decision function on the support vectors that are the borderline cases, other methods such as the method used by Golub et al (1999) base their decision function on the average case. See FIG. 13C and 13D. 13A shows separation of the training examples with an SVM. The training examples are separated without error. The margin on either side of the decision boundary is maximized. 13B shows separation of the training and test examples with the same SVM. Only one example is misclassified. 13C shows separation of the training examples with the baseline method of Golub, 1999. The decision boundary is perpendicular to the direction defined by the class centroids. 13D shows separation of the training and test examples with the baseline method. Three examples are misclassified.

In the preferred embodiment shown herein, one of the variants of the soft-margin algorithm described in Cortes, 1995, was used. Solve the following quadratic programming problem:

Minimize over $\alpha_i$:

$$(\tfrac{1}{2})\Sigma_{ij} y_i y_j \alpha_i \alpha_j (x_i . x_j + \zeta \delta_{ij}) - \Sigma_i \alpha_i$$

subject to:

$$0 \leq \alpha_i \leq C \text{ and } \Sigma_i \alpha_i y_i = 0$$

where the summations run over all training patterns $x_i$ that are vectors of features (genes), $x_i . x_j$ denotes the scalar product, $y_i$ encodes the class label as a binary value +1 or −1, $\delta_{ij}$ is the Kronecker symbol ($\delta_{ij}=1$ if i=j and 0 otherwise), and $\zeta$ and C are positive constants (soft margin parameters). The soft margin parameters ensure convergence even when the problem is non-linearly separable or poorly conditioned. In such cases, some of the support vectors may not lie on the margin.

The resulting decision function of an input vector x is:

$$D(x) = w.x + b$$

with $$w = \Sigma_i \alpha_i y_i x_i \text{ and } b = \langle y_i - w.x_i \rangle$$

The weight vector w is a linear combination of training patterns. Most weights $\alpha_i$ are zero. The training patterns with non zero weights are support vectors. Those with weight satisfying the strict inequality $0 < \alpha_i < C$ are marginal support vectors. The bias value b is an average over marginal support vectors.

Recursive Feature Elimination (RFE)

Because the mutual information between features is used in the computation of the classifier weights for the SVM classifier, removing a subset of features affects the value of the weights. In contrast, correlation methods that make implicit independence assumptions yield weight values that are independent on the subset of features considered.

Rather than ranking the features once with the weights of an SVM classifier obtained by training on all features, a more refined ranking is obtained by removing one feature at a time. At each iteration, a new classifier is trained with the remaining features. The feature corresponding to the smallest weight in the new classifier is eliminated. The order of elimination yields a particular ranking. By convention, the last feature to be eliminated is ranked first. This method can be optimized for computational efficiency. However, it may eventually become too computationally expensive for large numbers of features (millions of genes). Other methods comprise elimination of chunks of genes at a time. At the first iteration, the number of genes which is the closest power of 2 was reached. At subsequent iterations, half of the remaining genes were eliminated. Thus, nested subsets of genes of increasing informative density were obtained.

The original data for training and testing the learning machine of the present invention for this application regarding colon cancer was derived from the data presented in Alon et al., 1999. Gene expression information was extracted from microarray data resulting, after pre-processing, in a table of 62 tissues×2000 genes. The 62 tissues include 22 normal tissues and 40 colon cancer tissues. The matrix contains the expression of the 2000 genes with highest minimal intensity across the 62 tissues. One problem in the colon cancer data set was that tumor samples and normal samples differed in cell composition. Tumor samples were normally rich in epithelial cells wherein normal samples were a mixture of cell types, including a large fraction of smooth muscle cells. Though the samples could be easily separated on the basis of cell composition, this separation was not very informative for tracking cancer-related genes.

Alon et al. provides an analysis of the data based on top down clustering, a method of unsupervised learning and also clusters genes by showing that some genes correlate with a cancer vs normal separation scheme but do not suggest a specific method of gene selection. They show that some genes are correlated with the cancer vs. normal separation but do not suggest a specific method of gene selection.

The gene selection method of this embodiment of present invention comprises a reference gene selection method like that of Example 2 and like that used in Golub et al, Science, 1999. In Golub, the authors use several metrics of classifier quality, including error rate, rejection rate at fixed threshold, and classification confidence. Each value is computed both on the independent test set and using the leave-one-out method on the training set. The leave-one-out method consists of removing one example from the training set, constructing the decision function on the basis only of the remaining training data and then testing on the removed example. In this method, one tests all examples of the training data and measures the fraction of error over the total number of training examples.

The methods of using the learning machine comprise modifications of the above metrics. The classification decision was carried out according to the sign of the SVM output. The magnitude of the output is indicative of classification confidence.

Four metrics of classifier quality were used. (see FIG. 14)

Error (B1+B2)=number of errors ("bad") at zero rejection.

Reject (R1+R2)=minimum number of rejected samples to obtain zero error.

Extremal margin (E/D)=difference between the smallest output of the positive class samples and the largest output of the negative class samples (rescaled by the largest difference between outputs).

Median margin (M/D)=difference between the median output of the positive class samples and the median output of the negative class samples (rescaled by the largest difference between outputs).

Each value is computed both on the training set with the leave-one-out method and on the test set.

The error rate is the fraction of examples that are misclassified (corresponding to a diagnostic error). It is complemented by the success rate. The rejection rate is the fraction of examples that are rejected (on which no decision is made because of low confidence). It is complemented by the acceptance rate. Extremal and median margins are measurements of classification confidence.

This method of computing the margin with the leave-one-out method or on the test set differed from the margin computed on training examples sometimes used in model selection criteria.

A method for predicting the optimum subset of genes comprised defining a criterion of optimality that uses information derived from training examples only. This was checked by determining whether the predicted gene subset performed best on the test set.

A criterion that is often used in similar "model selection" problems is the leave-one-out success rate $V_{suc}$. In the present example, it was of little use since differentiation between many classifiers that have zero leave-one-out error is not allowed. Such differentiation is obtained by using a criterion that combines all of the quality metrics computed by cross-validation with the leave-one-out method:

$$Q = V_{suc} + V_{acc} + V_{ext} + V_{med}$$

where $V_{suc}$ is the success rate, $V_{acc}$ the acceptance rate, $V_{ext}$ the extremal margin, and $V_{med}$ is the median margin.

Theoretical consideration yielded us to modify this criterion to penalize large gene sets. Indeed, the probability of observing large differences between the leave-one-out error and the test error increases with the size d of the gene set, using the formula below $$\epsilon(d) = \operatorname{sqrt}(-\log(\alpha) + \log(G(d))) \cdot \operatorname{sqrt}(p(1-p)/n)$$

where $(1-\alpha)$ is the confidence (typically 95%, i.e., $\alpha=0.05$), p is the "true" error rate ($p \leq 0.01$), and n is the size of the training set.

Following the guaranteed risk principle (Vapnik, 1974), we subtracted from criterion Q a quantity proportional to $\epsilon(d)$ to obtain a new criterion:

$$C = Q - 2\epsilon(d)$$

The coefficient of proportionality was computed heuristically, assuming that $V_{suc}$, $V_{acc}$, $V_{ext}$ and $V_{med}$ are independent random variables with the same error bar $\epsilon(d)$ and that this error bar is commensurate to a standard deviation. Since in that case variances would be additive, the error bar should be multiplied by sqrt(4).

A more detailed discussion of the methods of a preferred embodiment follow. An SVM Recursive Feature Elimination (RFE) was run on the raw data to assess the validity of the method. The colon cancer data samples were split randomly into 31 examples for training and 31 examples for testing. The RFE method was run to progressively downsize the number of genes by each time dividing it by 2. The preprocessing of the data was that for each gene expression value, the mean was subtracted and then the resultant was divided by the standard deviation.

The leave-one-out method with the classifier quality criterion was used to estimate the optimum number of genes. Example 2 also illustrates use of the leave-one-out method. The leave-one-out method comprises taking out one example of the training set. Training is performed on the remaining examples. The left out example is used to test. The procedure is iterated over all the examples. Every criteria is computed as an average over all examples. The overall classifier quality criterion is the sum of 4 values: the leave-one-out success rate (at zero rejections), the leave-one-out acceptance rate (at zero error), the leave-one-out extremal margin, and the leave-one-out median margin. The classifier is a linear classifier with hard margin.

Results of the above steps show that at the optimum predicted by the method using training data only, the leave-one-out error is zero and the test performance is actually optimum. Four genes are discovered and they are:

L07648 Human MXI1 mRNA, complete cds.
T47377 71035 S-100P PROTEIN (HUMAN).
M76378 Human cysteine-rich protein (CRP) gene, exons 5 and 6.
Z50753 H.sapiens mRNA for GCAP-II/uroguanylin precursor.

Figure 14:
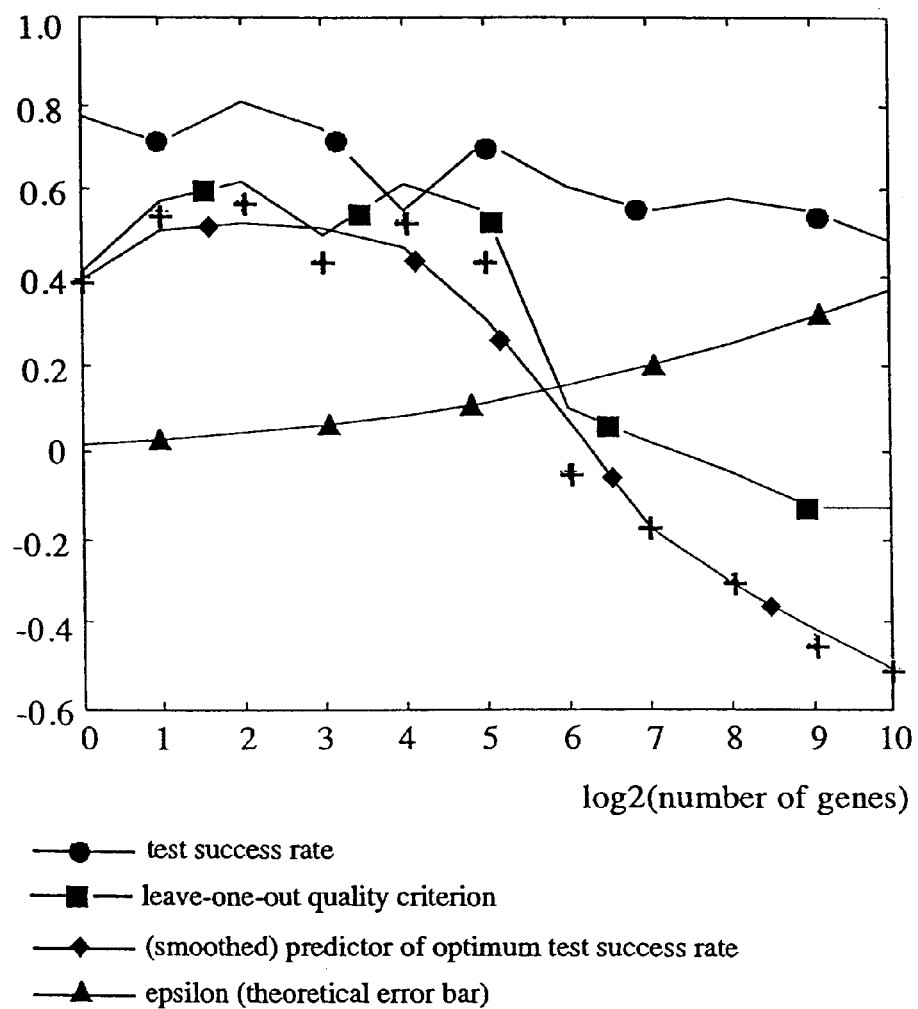
FIG. 14 shows graphs of the results of using RFE with information similar to Example 2.
Figure 15A:
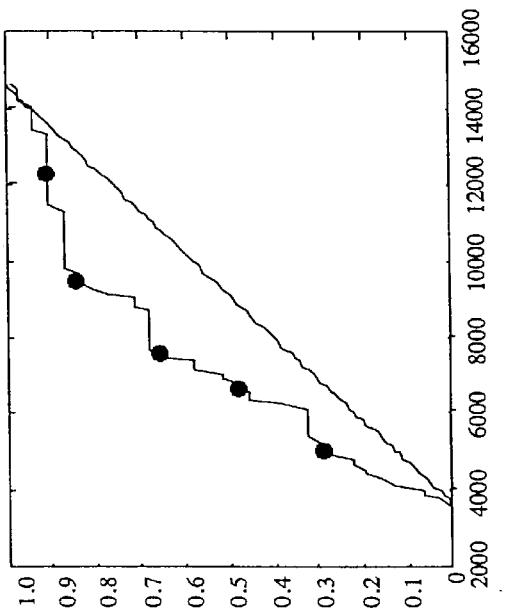
FIGS. 15A, 15B, 15C and 15D show the distribution of gene expression values across tissue samples for two genes.
Figure 15B:
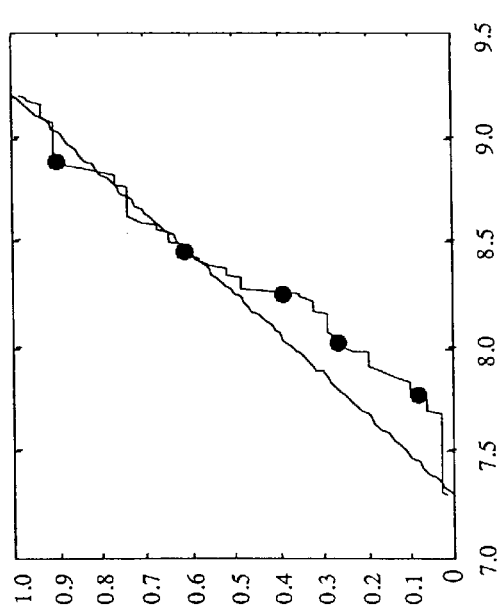
Figure 15C:
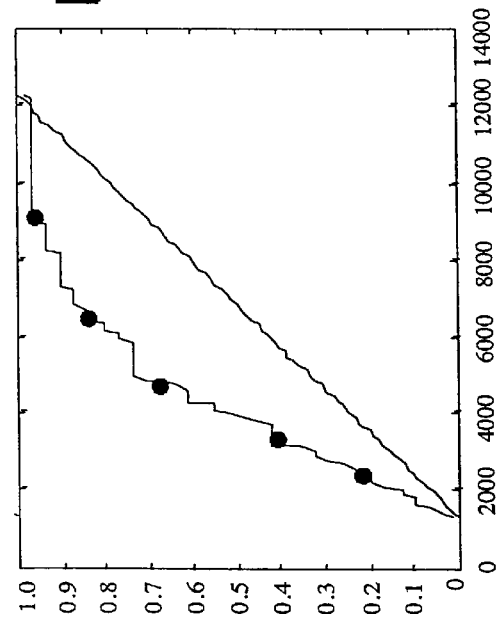
Figure 15D:
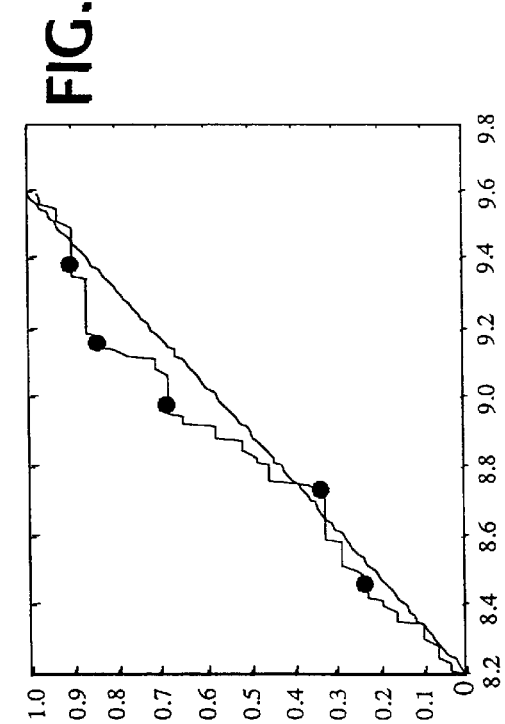

The optimum test performance had an 81% success rate. This result was consistent with the results reported in the original paper by Alon et al. Moreover, the errors, except for one, were identified by Alon et al. as outliers. The errors were 8, 36, 34, 12, −36, and −30, with 36 being the error not identified by Alon et al. as an outlier. The number identifies the tissue and the sign indicates presence or absence of tumor (negative=tumor, positive or no sign=normal. No direct performance comparison was made because Alon et al are using unsupervised learning on the entire data set whereas this embodiment used supervised learning on half of the data set. The plot of the performance curves at a function of gene number is shown in FIG. 14. The description of the graph of FIG. 14 is as follows: Horizontal axis=log2(number of genes). Curves: circle=test success rate; square=leave-one-out quality criterion; triangle= epsilon (theoretical error bar); diamonds=square−triangle (smoothed) predictor of optimum test success rate, the optimum of the diamond curve is at log2(num genes)=2= →num genes=4. It coincides with the optimum of the circle curve.

Preprocessing Steps

Taking the Log

The initial preprocessing steps of the data were described by Alon et al. The data was further preprocessed in order to make the data distribution less skewed. FIG. 15A, 15B, 15C and 15D show the distributions of gene expression values across tissue samples for two random genes (cumulative number of samples of a given expression value) which is compared with a uniform distribution. Each line represents a gene. 15A and 15B show the raw data; 15C and 15D are the same data after taking the log. By taking the log of the gene expression values the same curves result and the distribution is more uniform. This may be due to the fact that gene expression coefficients are often obtained by computing the ratio of two values. For instance, in a competitive hybridization scheme, DNA from two samples that are labeled differently are hybridized onto the array. One obtains at every point of the array two coefficients corresponding to the fluorescence of the two labels and reflecting the fraction of DNA of either sample that hybridized to the particular gene. Typically, the first initial preprocessing step that is taken is to take the ratio a/b of these two values. Though this initial preprocessing step is adequate, it may not be optimal when the two values are small. Other initial preprocessing steps include (a−b)/(a+b) and (log a−log b)/(log a+log b).

Subtracting the Array Mean

FIGS. 16A and 16B show the distribution of gene expression values across genes for all tissue samples. 16A shows the raw data and 16B shows the inv erf. The shape is roughly that of an erf function, indicating that the density follows approximately the Normal law. Indeed, passing the data through the inverse erf function yields almost straight parallel lines. Thus, it is reasonable to normalize the data by subtracting the mean. This preprocessing step is also suggested by Alon et al. This preprocessing step is supported by the fact that there are variations in experimental conditions from microarray to microarray. Although standard deviation seems to remain fairly constant, the other preprocessing step selected was to divide the gene expression values by the standard deviation to obtain centered data of standardized variance.

Normalizing Each Gene Expression Across Tissue Samples

Figure 17:
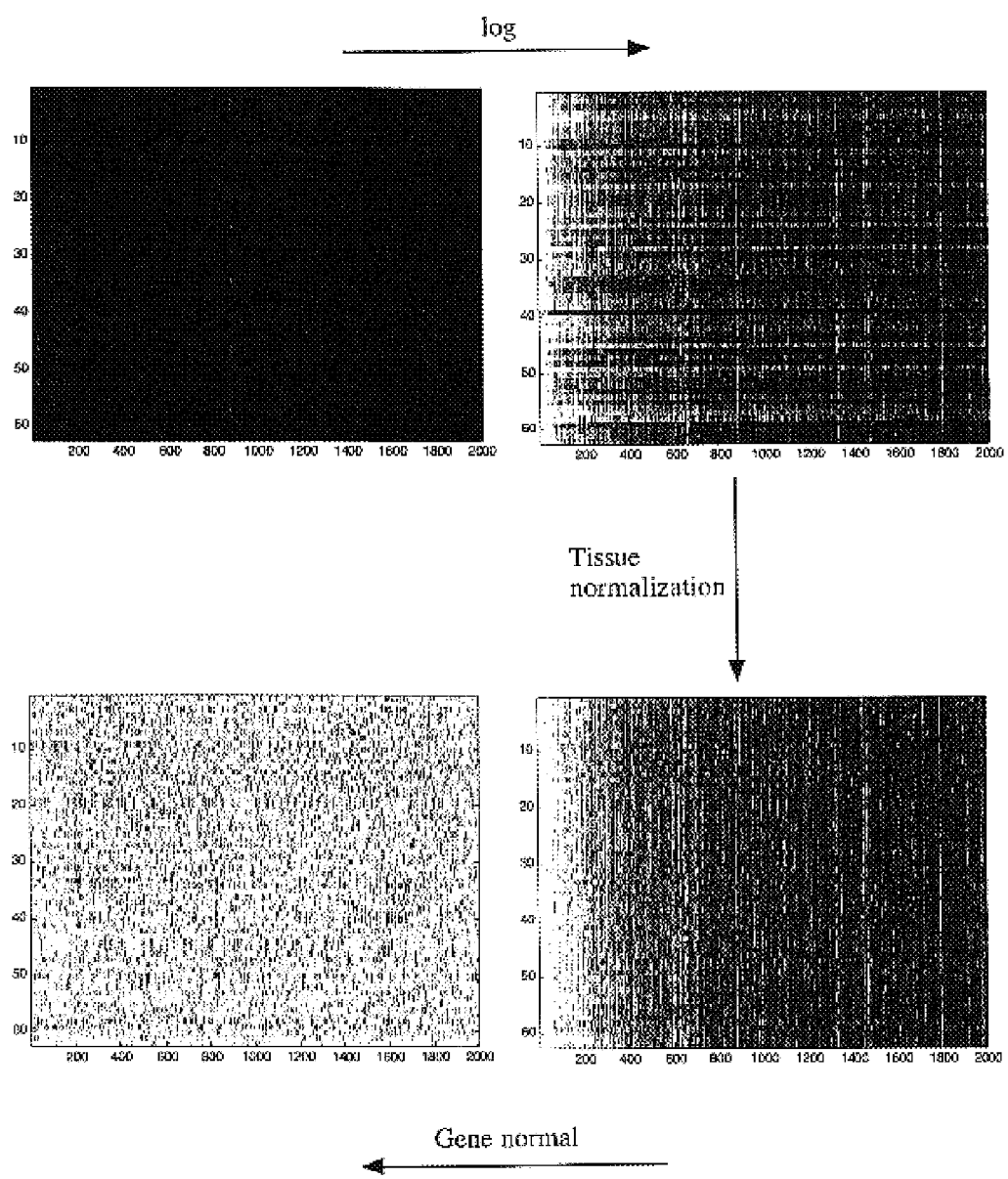
FIG. 17 shows the data matrices representing gene expression values from microarray data for colon cancer.

Using training data only, the mean expression value and standard deviation for each gene was computed. For all the tissue sample values of that gene (training and test), that mean was then subtracted and the resultant value was divided by the standard deviation. FIG. 17 shows the results of these preprocessing steps. FIG. 17 shows the data matrices representing gene expression values from microarray data for colon cancer wherein the lines represent 62 tssues and the columns represent the 2000 genes.

In some experiments, an additional preprocessing step was added by passing the data through a squashing function to diminish the importance of the outliers.

New RFE Results

The data was preprocessed as described above and summarized in FIG. 17 to produce new and improved results. In this method, there are modifications from those used in Example 2. First, the code was optimized such that RFE can be run by eliminating one gene at a time. In Example 2, chunks of genes at a time were eliminated. The chunk size was divided by 2 at every iteration. This processing modification of this embodiment provides a finer ranking that allows for various analyses but does not significantly affect classification accuracy. It runs in about 10–15 minutes, for example, on a Pentium III 333, 256 MB RAM.

A second modification, different from the methods of Example 2, was that the gene selection cross-validation process used a regular SVM. In Example 2, a reduced capacity SVM was used by projecting first the data on the first principal component.

Figure 18:
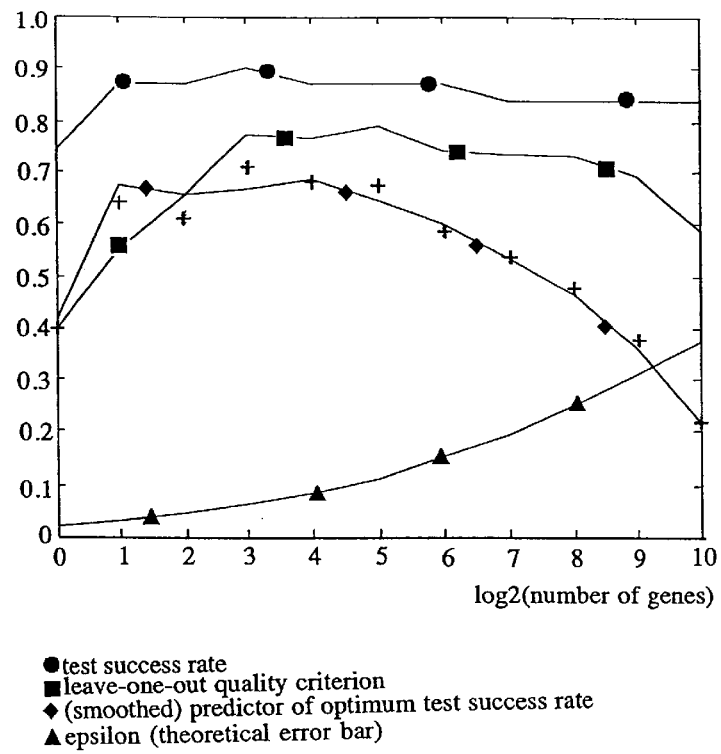
FIG. 18 shows the results of RFE after preprocessing.

The results of FIG. 18 show a significant improvement over those of FIG. 14. FIG. 18 shows the results of RFE after preprocessing. The description for FIG. 18 is as follows: Horizontal axis=log2(number of genes). Curves: circle=test success rate; square=leave-one-out quality criterion; triangle=epsilon (theoretical error bar); diamond=square–triangle (smoothed) predictor of optimum test success rate the optimum of the diamond curve is at log2(num genes)= 4→num genes=16. Reduced capacity SVM used in FIG. 14 is replaced by plain SVM. Although a log scale is still used for gene number, RFE was run by eliminating one gene at a time. The best test performance is 90% classification accuracy (8 genes). The optimum number of genes predicted from the classifier quality based on training data information only is 16. This corresponds to 87% classification accuracy on the test set. The same test performance is also achieved with only 2 genes as follows:

J02854: Myosin regulatory light chain 2, smooth muscle isoform human); contains element TAR1 repetitive element.

R55310: S36390 Mitochondrial processing peptidase.

Neither of these two genes appears at the top of the list in the first experiment.

The top gene found is a smooth muscle gene, which is a gene characteristic of tissue composition and is probably not related to cancer.

Comparison with Golub's Method

Figure 19:
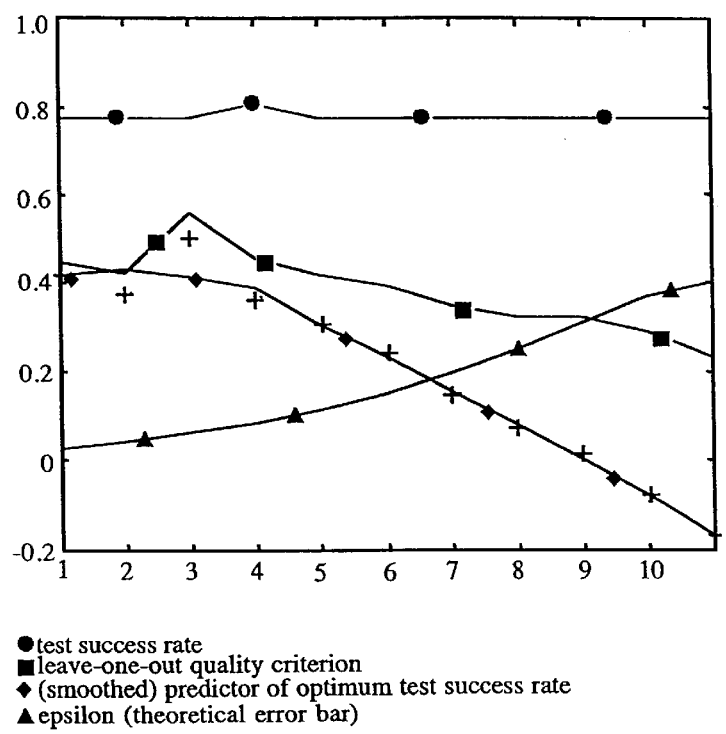
FIG. 19 shows a graphical comparison with the present invention and the methods of Golub.

Golub's gene selection method is a ranking method where genes are ordered according to the correlation between vectors of gene expression values for all training data samples and the vector of target values (+1 for normal sample and −1 for cancer sample). Golub et al select m/2 top ranked and m/2 bottom ranked genes to obtain one half of genes highly correlated with the separation and one half anti-correlated. Golub et .al use a linear classifier. To classify an unknown sample, each gene "votes" for cancer or normal according to its correlation coefficient with the target separation vector. The top gene selected by Golub's method was J02854 (smooth muscle related). FIG. 19 illustrates the comparison of this embodiment's use of the baseline method with Golub et al. The same curves as were used in FIG. 18 are shown in FIG. 19. The description for FIG. 19 is as follows: Horizontal axis=log2(number of genes). Curves: circle=test success rate; square=leave-one-out quality criterion; triangle=epsilon (theoretical error bar); diamond= square–triangle (smoothed) predictor of optimum test success rate. The data, pre-processed identically in FIGS. 18 and 19, was then treated by Golub's method and graphed in FIG. 19. It is the novel finding of the present inventors to select an optimum number of genes to use with learning machines such as SVMs.

To compare the results of the methods of this embodiment of the present invention and Golub, a statistical test was used that determines with what confidence $(1-\alpha)$ that one classifier is better than the other, using the formula:

$$(1-\alpha)=0.5+0.5 \text{ erf}(z_\alpha/\text{sqrt}(2))$$

$$z_\alpha = \epsilon n/\text{sqrt}(v)$$

where n is the number of test examples, v is the total number of errors that only one of the 2 classifiers makes, and $\epsilon$ is the difference in error rate. (or in rejection rate).

This formula was applied to the results summarized in Table 1. In either case, $\epsilon=3/31$ and v=3. The total number of test examples is n=31. On the basis of this test, the methods of this embodiment of the present invention were better than Golub with 95.8% confidence.

TABLE 1

Error rates comparisons between the methods of this embodiment of the present invention and Golub's method. The list of errors is shown between brackets. The numbers indicate the patients. The sign indicates cancer (negative) or normal (positive). For this embodiment of the present invention, the best performance was at 8 genes and the optimum predicted at 16 genes. For Golub, the best performance was at 16 genes and the optimum predicted at 4 genes. Note that there was only one error difference between the best performance and the optimum predicted in either case.

| Method | Optimum error rate {errors made} | Error rate at the optimum number of genes {errors made} |
| --- | --- | --- |
| Embodiment of Present Invention | 9.68 {29, 1, −17} | 12.90 {29, 1, −17, −35} |
| Golub | 19.35 {39, 29, 1, −17, −35, −29} | 22.58 {39, 29, 1, −21, −17, −35, −29} |

Combining Clustering and Gene Selection

Because of data redundancy, it was possible to find many subsets of genes that provide a reasonable separation. To analyze the results, it was optimal to understand how these genes are related. Though not wishing to be bound by any particular theory, it was the initial theory that the problem of gene selection was to find an optimum number of genes, preferably small, that separates normal tissues from cancer tissues with maximum accuracy.

SVM recursive feature elimination (RFE) used a subset of genes that were complementary and thus carried little redundant information. No other information on the structure and nature of the data was provided. Because data were very redundant, a gene that had not been selected may nevertheless be informative for the separation.

Correlation methods such as Golub's method provide a ranked list of genes. The rank order characterizes how correlated the gene is with the separation. Generally, a gene highly ranked taken alone provides a better separation than a lower ranked gene. It is therefore possible to set a threshold (e.g. keep only the top ranked genes) that separates "highly informative genes" from "less informative genes".

Figure 20A:
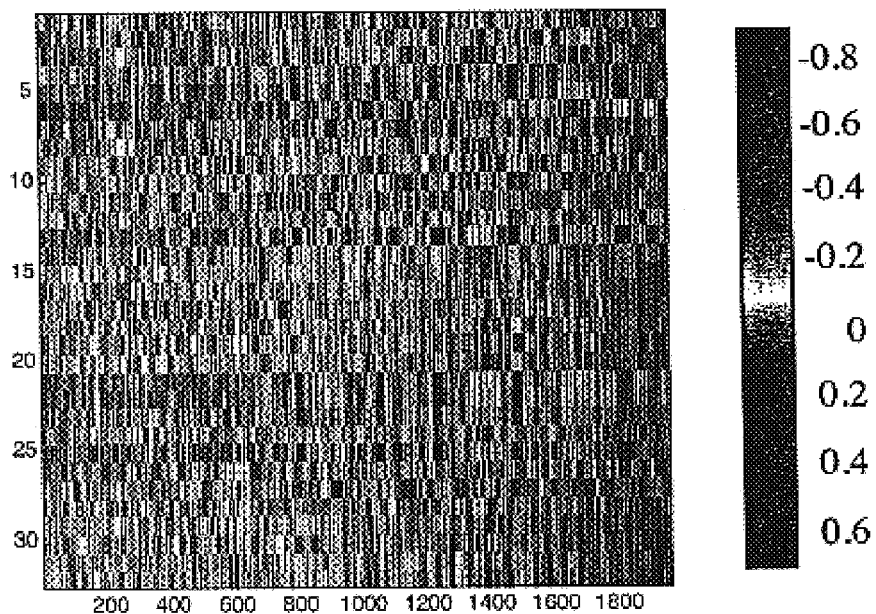
FIGS. 20A and 20B show the correlation between the best 32 genes and all other genes.
Figure 20B:
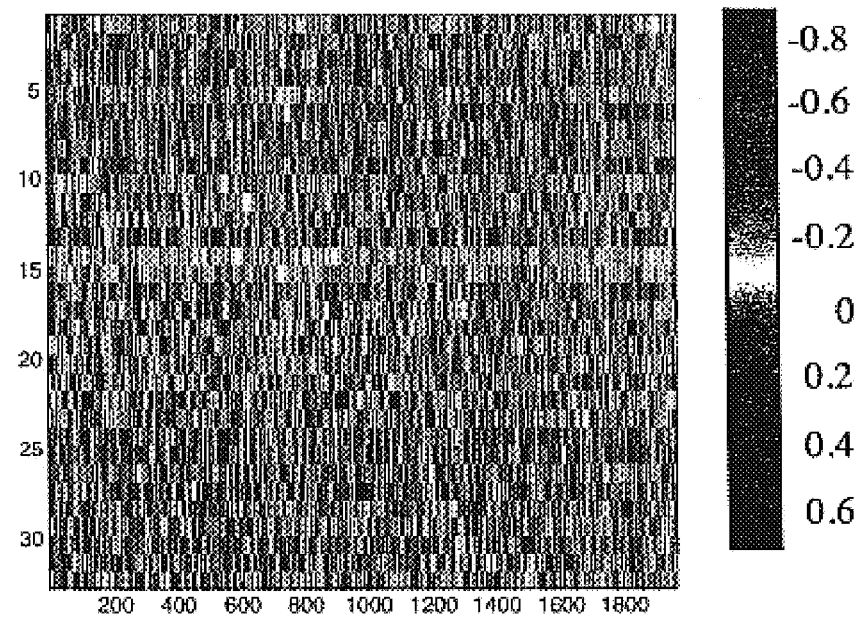

The methods of the present invention such as SVM RFE provide subsets of genes that are both smaller and more discriminant. The SVM gene selection method using RFE also provides a ranked list of genes. With this list, nested subsets of genes of increasing sizes can be defined. However, the fact that one gene has a higher rank than another gene does not mean that that factor alone characterizes the better separation. In fact, genes that are eliminated very early on may be very informative but redundant with others that were kept. These differences between Golub's method and SVM's method are illustrated in FIG. 20A and 20B. The figures represent the matrices of Pearson correlation coefficients. 20A shows the Golub method. Genes of increasing rank have increasing correlation (or anti-correlation) with the target separation. The absolute values of correlation coefficients are larger between the 32 best genes and the other genes that have highest rank. 20B shows the SVM method. The 32 best genes as a whole provide a good separation but individually may not be very correlated with the target separation. Gene ranking allows for a building nested subsets of genes that provide good separations. It is not informative for how good an individual gene is. Genes of any rank may be correlated with the 32 best genes. They may been ruled out at some point because the their redundancy with some of the remaining genes, not because they did not carry information relative to the target separation.

The gene ranking alone is insufficient to characterize which genes are informative and which ones are not, and also to determine which genes are complementary and which ones are redundant.

Unsupervised Clustering

To overcome the problems in gene ranking alone, the data was preprocessed with an unsupervised clustering method. Genes were grouped according to resemblance (with a given metric). Cluster centers are then used instead of genes themselves and processed by SVM RFE. The result was nested subsets of cluster centers. An optimum subset size can be chosen with the same cross-validation method used before. The cluster centers can then be replaced either element of the cluster.

Figure 21:
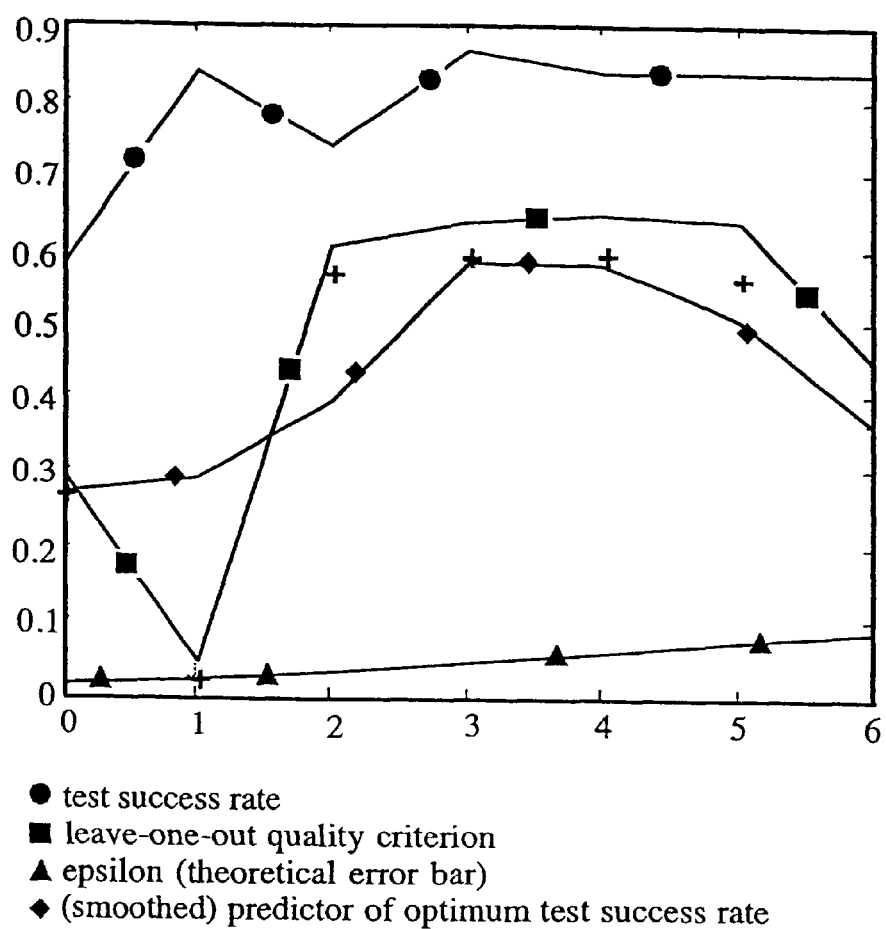
FIG. 21 shows the results of RFE when training on 100 dense QT_clust clusters.

Using the data, the QT_clust clustering algorithm was used to produce 100 dense clusters. The similarity measure used was Pearson's correlation coefficient (as commonly used for gene clustering). FIG. 21 shows the performance curves. FIG. 21 shows the results of RFE when training on 100 dense QT_clust clusters. Horizontal axis=log2 (number of gene cluster centers). Curves: circle=test success rates; square=leave-one-out quality criterion; triangle=epsilon (theretical error bar); diamond=square–traingle (smoothed) predictor of optimum test success rate the optimum of the diamond curve is at log2(number of gene cluseter centers)= 3→number of gene cluster centers=8.

Figure 22A:
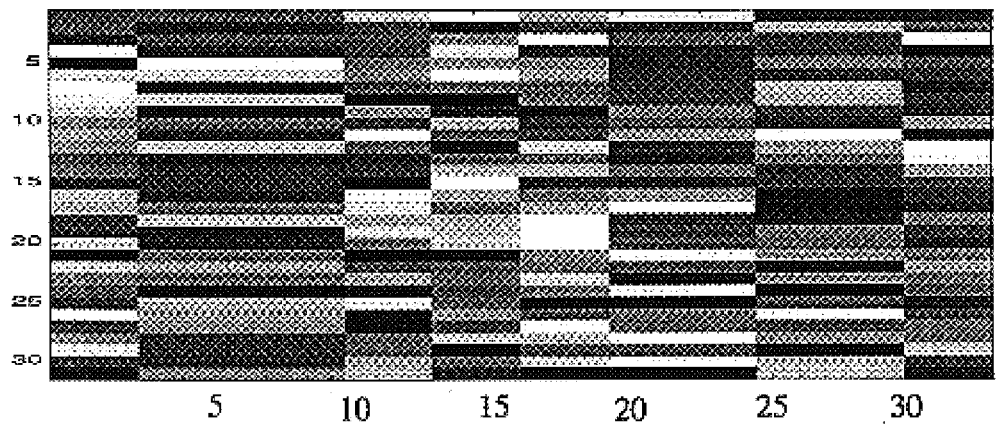
FIG. 22A and 22B show the top 8 QT_clust clusters chosen by SVM RFE.
Figure 22B:
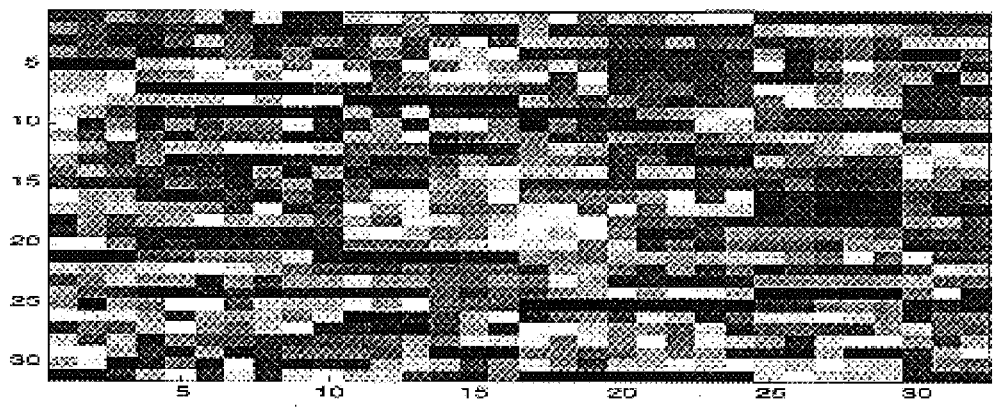

They are comparable to those of FIG. 18. FIG. 22 shows the top 8 QT_lust clusters chosen by SVM RFE. In FIG. 22A and 22B, the gene expression for the 32 tissues of the training set (columns) for 8 clusters (lines) are represented. Positive gene expressions are red and negative gene expressions are blue. Small values have lighter color. 22A shows cluster centers; 22B shows cluster elements. The cluster elements are listed in Table 2.

TABLE 2

QT_clust clusters selected with RFE. The higher the cluster rank (Rk), the more important the cluster. Min correl is the minimum correlation coefficient between cluster elements. GAN = Gene Accession Number.

| Rk | Min correl | GAN | Description |
|---|---|---|---|
| 1 | 0.82 | X54163 | TROPONIN I, CARDIAC MUSCLE (HUMAN);contains element MER22 repetitive element |
| | | D23672 | Human mRNA for biotin-[propionyl-CoA-carboxylase(ATP-hydrolysing)] ligase, complete cds. |
| | | Y00970 | |
| 2 | 0.82 | T51023 | 75127 HEAT SHOCK PROTEIN HSP 90-BETA (HUMAN). |
| | | T69446 | 82983 EUKARYOTIC INITIATION FACTOR 4A-I (HUMAN);. |
| | | R37428 | 26100 Human unknown protein mRNA, partial cds. |
| | | H89087 | 253224 SPLICING FACTOR SC35 (Homo sapiens) |
| | | R96357 | 197929 POLYADENYLATE-BINDING PROTEIN (Xenopus laevis) |
| | | T96873 | 121343 HYPOTHETICAL PROTEIN IN TRPE 3REGION (Spirochaeta aurantia) |
| | | H72234 | 213492 DNA-(APURINIC OR APYRIMIDINIC SITE) LYASE (HUMAN);. |
| 3 | 0.83 | T85247 | 111192 CYTOCHROME C OXIDASE POLYPEPTIDE VIC PRECURSOR (HUMAN);. |
| | | R08021 | 127104 INORGANIC PYROPHOSPHATASE (Bos taurus) |
| | | M22760 | Homo sapiens nuclear-encoded mitochondrial cytochrome c oxidase Va subunit mRNA, complete cds. |
| 4 | 0.84 | T94579 | 119384 Human chitotriosidase precursor mRNA, complete cds. |
| | | T83361 | 116665 GAMMA INTERFERON INDUCED MONOKINE PRECURSOR (Homo sapiens) |
| | | R89377 | 196061 NEDD5 PROTEIN (Mus musculus) |
| 5 | 0.85 | R51749 | 39237 TRANS-ACTING TRANSCRIPTIONAL PROTEIN ICP4 (Equine herpesvirus type 1) |
| | | R10620 | 128901 TYROSINE-PROTEIN KINASE CSK (Homo sapiens) |
| | | H29483 | 49967 INTERCELLULAR ADHESION MOLECULE-2 PRECURSOR (HUMAN);. |
| 6 | 0.82 | X55187 | Human mRNA for alpha-actinin, partial cds. |
| | | X74295 | H.sapiens mRNA for alpha 7B integrin. |
| | | R48303 | 153505 TYROSINE RICH ACIDIC MATRIX PROTEIN (Bos taurus) |
| | | X86693 | H.sapiens mRNA for hevin like protein. |
| | | H06524 | 44386 GELSOLIN PRECURSOR, PLASMA (HUMAN);. |
| 7 | 0.87 | H61410 | 211590 PLATELET GLYCOPROTEIN IV (Homo sapiens) |
| | | H67764 | 229939 ESTROGEN SULFOTRANSFERASE (Bos taurus) |
| | | U06698 | Human neuronal kinesin heavy chain mRNA, complete cds. |

TABLE 2-continued

QT_clust clusters selected with RFE. The higher the cluster rank (Rk), the more important the cluster. Min correl is the minimum correlation coefficient between cluster elements. GAN = Gene Accession Number.

| Rk | Min correl | GAN | Description |
|----|-----------|-----|-------------|
|    |           | R39209 | 23464 HUMAN IMMUNODEFICIENCY VIRUS TYPE I ENHANCER-BINDING PROTEIN 2 (*Homo sapiens*) |
|    |           | R39209 | 23464 HUMAN IMMUNODEFICIENCY VIRUS TYPE I ENHANCER-BINDING PROTEIN 2 (*Homo sapiens*) |
| 8  | 0.82      | R10066 | 128808 PROHIBITIN (*Homo sapiens*) |
|    |           | U09564 | Human serine kinase mRNA, complete cds. |
|    |           | R62549 | 138906 PUTATIVE SERINE/THREONINE-PROTEIN KINASE B0464.5 IN CHROMOSOME III (*Caenorhabditis elegans*) |

With unsupervised clustering, a set of informative genes is defined, but there is no guarantee that the genes not retained do not carry information. When RFE was used on all QT_clust clusters plus the remaining non-clustered genes (singleton clusters), the performance curves were quite similar, though the top set of gene clusters selected was completely different and included mostly singletons. The genes selected in Table 1 are organized in a structure: within a cluster, genes are redundant, across clusters they are complementary.

The cluster centers can be substituted by any of their members. This factor may be important in the design of some medical diagnosis tests. For example, the administration of some proteins may be easier than that of others. Having a choice of alternative genes introduces flexibility in the treatment and administration choices.

Ten random choices were tested, in that one gene of each of the 8 clusters was selected randomly. The average test set accuracy was 0.80 with a standard deviation of 0.05. This is to be compared with 0.87 for the cluster centers. One of the random choice tests yielded an accuracy that was superior to that of the centers (0.90): D23672, T51023, T85247, R89377, R51749, X55187, R39209, U09564.

Hierarchical clustering instead of QT_clust clustering was used to produce lots of small clusters containing 2 elements on average. Because of the smaller cluster cardinality, there were fewer gene alternatives from which to choose. In this instance, hierarchical clustering did not yield as good a result as using QT_clust clustering. The present invention contemplates use of any of the known methods for clustering, including but not limited to hierarchical clustering, QT_clust clustering and SVM clustering. The choice of which clustering method to employ in the invention is affected by the initial data and the outcome desired, and can be determined by those skilled in the art.

Figure 23:
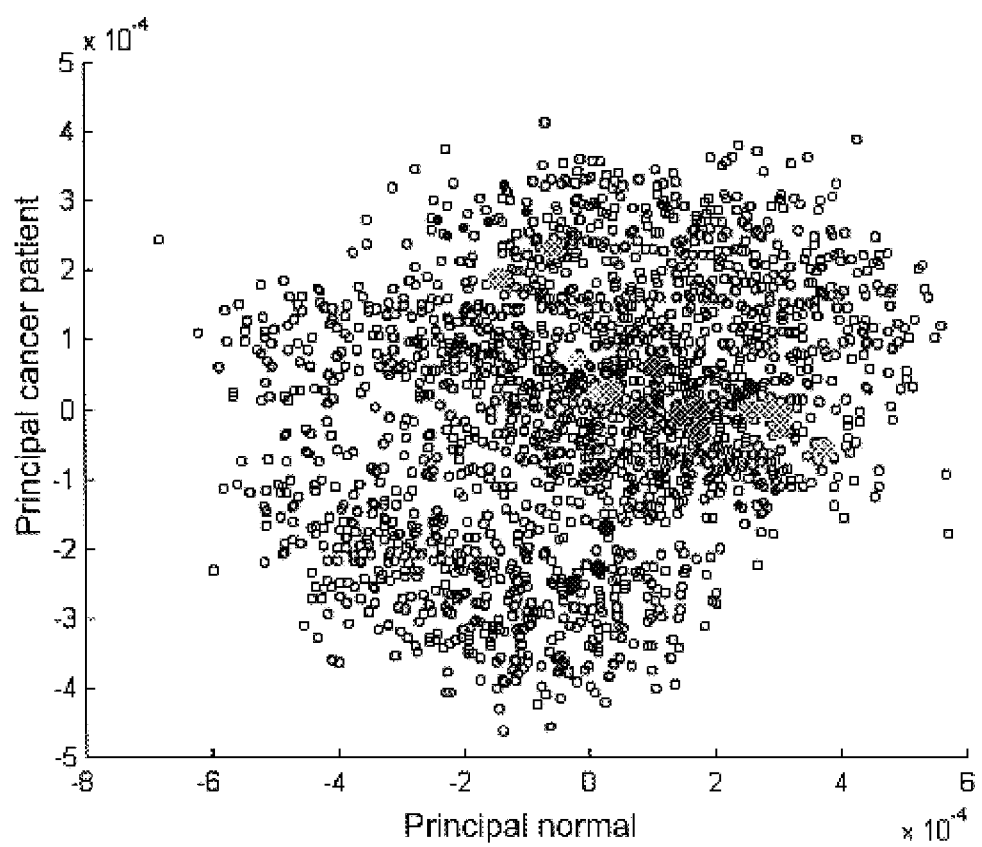
FIG. 23 shows the QT_clust top gene scatter plot

A scatter plot of the selected genes from the 8 clusters in Table 2, shown in color and the rest are circles, is shown in FIG. 23. Each dot represent the gene expression value of average patients obtained by principal component analysis. The colored dots are the genes selected by SVM RFE using QT_clust clusters. Each cluster is assigned a randomly selected color. The dot size is proportional to the cluster rank. To obtain this scatter plot, all normal tissue was replaced by a single average normal tissue (first principal component called "principal normal tissue"). The same was done for the cancer tissues. Each point represents a gene expression in the principal cancer tissue/principal normal tissue two-dimensional space.

Supervised Clustering

Another method used with the present invention was to use clustering as a post-processing step of SVM RFE. Each gene selected by running regular SVM RFE on the original set of gene expression coefficients was used as a cluster center. For example, the results described in FIG. 18 were used. For each of the top eight genes, the correlation coefficient was computed with all remaining genes. The parameters were that the genes clustered to gene i were the genes that met the following two conditions: must have higher correlation coefficient with gene i than with other genes in the selected subset of eight genes, and must have correlation coefficient exceeding a threshold θ.

In the Figures and Tables presented herein the results for 8 genes were presented. An optimally predicted number of 16 genes were not presented because displaying the results for 16 genes yields bigger tables and does not provide more insight into the method.

Figure 24A:
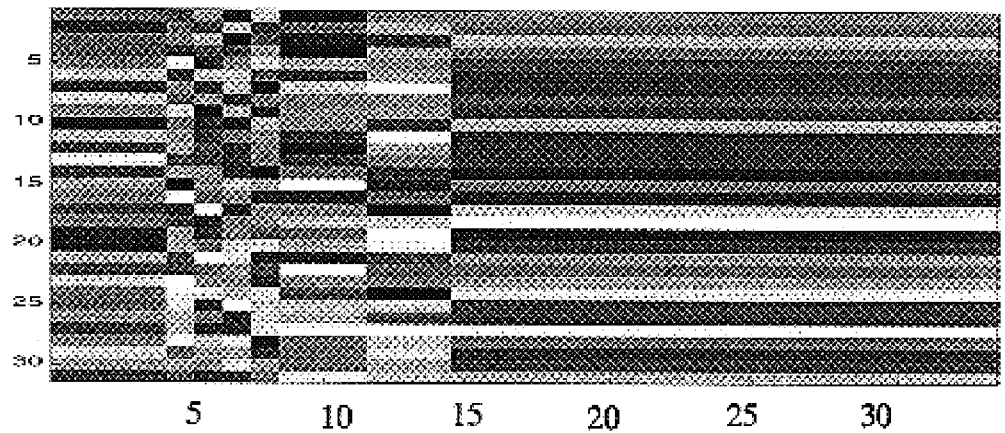
FIG. 24A and 24B show supervised clustering.
Figure 24B:
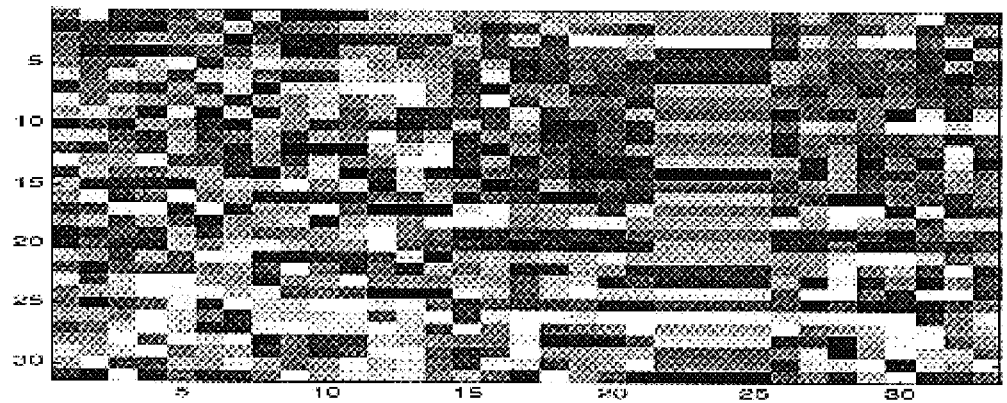

The clustered genes are shown in FIGS. 24A and 24B and listed in Table 3.

TABLE 3

Supervised clustering. Clusters were built around the best genes found by regular SVM RFE. Parameter θ is 0.8 (see text). The higher the cluster rank (Rk), the more "relevant" the cluster should be. Min correl is the minimum correlation coefficient between cluster elements. GAN = Gene Accession Number. The cluster centers are preceded by a star. In cluster 8, we omitted 8 "control" values that show in the middle of the last cluster in FIGS. 24A and 24B.

| Rk | Min correl | GAN | Description |
|----|-----------|-----|-------------|
| 1  | 0.74      | *Z50753 | *H.sapiens* mRNA for GCAP-II/uroguanylin precursor. |
|    |           | M36634  | Human vasoactive intestinal peptide (VIP) mRNA, complete cds. |
|    |           | T95018  | 120032 40S RIBOSOMAL PROTEIN S18 (*Homo sapiens*) |
|    |           | M36981  | Human putative NDP kinase (nm23-H2S) mRNA, complete cds. |
| 2  | 1         | *L34657 | *Homo sapiens* platelet/endothelial cell adhesion molecule-1 (PECAM-1) gene, exon 16 and complete cds. |
| 3  | 1         | *L07648 | Human MXI1 mRNA, complete cds. |
| 4  | 1         | *T51571 | 72250 P24480 CALGIZZARIN. |
| 5  | 1         | *R88740 | 194984 ATP SYNTHASE COUPLING FACTOR 6, MITOCHONDRIAL PRECURSOR (HUMAN);. |
| 6  | 0.81      | *X70326 | *H.sapiens* MacMarcks mRNA. |
|    |           | X12671  | Human gene for heterogeneous nuclear ribonucleoprotein (hnRNP) core protein A1. |
|    |           | D59253  | Human mRNA for NCBP interacting protein 1. |
| 7  | 0.78      | *R55310 | 154810 S36390 MITOCHONDRIAL PROCESSING PEPTIDASE;. |
|    |           | H09137  | 46399 UBIQUINOL-CYTOCHROME C REDUCTASE CORE PROTEIN 2 PRECURSOR (HUMAN);. |
|    |           | T51250  | 70115 CYTOCHROME C OXIDASE POLYPEPTIDE VIII-LIVER/HEART (HUMAN). |
| 8  | 0.58      | *J02854 | MYOSIN REGULATORY LIGHT CHAIN 2, SMOOTH MUSCLE ISOFORM (HUMAN);contains element TAR1 repetitive element;. |
|    |           | M26697  | Human nucleolar protein (B23) mRNA, complete cds. |
|    |           | X15882  | Human mRNA for collagen VI alpha-2 C-terminal globular domain. |

TABLE 3-continued

Supervised clustering. Clusters were built around the best genes found by regular SVM RFE. Parameter θ is 0.8 (see text). The higher the cluster rank (Rk), the more "relevant" the cluster should be. Min correl is the minimum correlation coefficient between cluster elements. GAN = Gene Accession Number. The cluster centers are preceded by a star. In cluster 8, we omitted 8 "control" values that show in the middle of the last cluster in FIGS. 24A and 24B.

| Rk | Min correl | GAN | Description |
|---|---|---|---|
| | | M81635 | *Homo sapiens* erythrocyte membrane protein mRNA, complete cds. |
| | | R78934 | 146232 ENDOTHELIAL ACTIN-BINDING PROTEIN (*Homo sapiens*) |
| | | T60155 | 81422 ACTIN, AORTIC SMOOTH MUSCLE (HUMAN);. |
| | | M64110 | Human caldesmon mRNA, complete cds. |
| | | M22382 | MITOCHONDRIAL MATRIX PROTEIN P1 PRECURSOR (HUMAN);. |
| | | T60778 | 76539 MATRIX GLA-PROTEIN PRECURSOR (*Rattus norvegicus*) |
| | | M91463 | Human glucose transporter (GLUT4) gene, complete cds. |
| | | T92451 | 118219 TROPOMYOSIN, FIBROBLAST AND EPITHELIAL MUSCLE-TYPE (HUMAN);. |
| | | T67077 | 66563 SODIUM/POTASSIUM-TRANSPORTING ATPASE GAMMA CHAIN (*Ovis aries*) |
| | | X86693 | *H.sapiens* mRNA for hevin like protein. |
| | | U09564 | Human serine kinase mRNA, complete cds. |
| | | M63391 | Human desmin gene, complete cds. |

FIG. 24A and 24B show the gene expression for the 32 tissues of the training set (columns) for 8 clusters (lines. Positive gene expressions are red and negative gene expressions are blue. Small values have lighter color. 24A shows the top 8 genes obtained by regular SVM RFE are used as cluster centers. 24B shows all the elements of the clusters. Cluster elements may be highly correlated or anti-correlated to the cluster center.

Compared to the unsupervised clustering method and results, the supervised clustering method, in this instance, does not give better control over the number of examples per cluster. Therefore, this method is not as good as unsupervised clustering if the goal is to be able to select from a variety of genes in each cluster. However, supervised clustering may show specific clusters that have relevance for the specific knowledge being determined. In this particular embodiment, in particular, a very large cluster of genes was found that contained several muscle genes that may be related to tissue composition and may not be relevant to the cancer vs. normal separation. Thus, those genes are good candidates for elimination from consideration as having little bearing on the diagnosis or prognosis for colon cancer.

Factoring Out Tissue Composition Related Genes

The following method was directed to eliminating the identified tissue composition related genes automatically. Those genes complicate the analysis of the results because it was not possible to differentiate them from genes that are informative for the cancer vs. normal separation. The results with the unsupervised learning preprocessing showed that the top ranked genes did not contain the key words "smooth muscle" that were used to detect potential tissue composition related genes. A cardiac muscle gene was still selected under this method.

Using the training set/test set split that was described earlier, other methods were used. For example, some of the top ranked genes were eliminated and the gene selection process was run again until there were no more "smooth muscle" genes or other muscle genes in the top ranked genes. But, the performance on the test set deteriorated and there was no automatic criterion that would allow the determination of when the gene set was free of tissue composition related genes.

In a most preferred method of the present invention, the gene selection process was performed on the entire data set. With a larger number of training samples, the learning machine, such as the SVM used here, factored out tissue composition related genes. Though not wishing to be bound by any particular theory, it is theorized that the SVM property of focusing on borderline cases (support vectors) may take advantage of a few examples of cancer tissue rich in muscle cells and of normal tissues rich in epithelial cells (the inverse of the average trend).

The resulting top ranking genes were free of muscle related genes, including the genes that were clustered with supervised clustering. In contrast, Golub's method obtains 3 smooth muscle related genes in the 7 top ranking gene cluster alone. Further, the top ranking genes found by SVM RFE were all characterizing the separation, cancer vs. normal (Table 4). The present invention is not only making a quantitative difference on this data set with better classification accuracy and smaller gene subset, but is also making a qualitative difference: the gene set is free of tissue composition related genes.

TABLE 4

The 7 top ranked genes discovered by the methods of the present invention, in order of increasing importance. Rk: rank. Sgn: sign of correlation with the target separation, − for over-expressed in most cancer tissues; + for over-expressed in most normal tissues; GAN: Gene Accession Number; The possible function is derived from a keyword search involving "colon cancer" or "cancer" and some words in the gene description.

| Rk | Sgn | GAN | Description | Possible function/relation to colon cancer |
|---|---|---|---|---|
| 1 | − | H08393 | COLLAGEN ALPHA 2(XI) CHAIN (*Homo sapiens*) | Collagen is involved in cell adhesion. Colon carcinoma cells have collagen degrading activity as part of the metastatic process. |
| 2 | − | M59040 | Human cell adhesion molecule (CD44) mRNA, complete cds. | CD44 is upregulated when colon adenocarcinoma tumor cells transit to the metastatic state. |
| 3 | − | T94579 | Human chitotriosidase precursor mRNA, complete cds. | Another chitinase (BRP39) was found to play a role in breast cancer. Cancer cells overproduce this chitinase to survive apoptosis. |
| 4 | + | H81558 | PROCYCLIC FORM SPECIFIC POLYPEPTIDE B1-ALPHA PRECURSOR (*Trypanosoma brucei brucei*) | It was shown that patients infected by Trypanosoma (a colon parasite) develop resistance against colon cancer. |
| 5 | + | R88740 | ATP SYNTHASE COUPLING FACTOR 6, MITO-CHONDRIA L PRECURSOR (HUMAN) | ATP synthase is an enzyme that helps build blood vessels that feed the tumors. |

TABLE 4-continued

The 7 top ranked genes discovered by the methods of the present invention, in order of increasing importance. Rk: rank. Sgn: sign of correlation with the target separation, – for over-expressed in most cancer tissues; + for over-expressed in most normal tissues; GAN: Gene Accession Number; The possible function is derived from a keyword search involving "colon cancer" or "cancer" and some words in the gene description.

| Rk Sgn | GAN | Description | Possible function/relation to colon cancer |
|---|---|---|---|
| 6 – | T62947 | 60S RIBOSOMAL PROTEIN L24 (Arabidopsis thaliana) | May play a role in controlling cell growth and proliferation through the selective translation of particular classes of mRNA. |
| 7 + | H64807 | PLACENTAL FOLATE TRANSPORTER (Homo sapiens) | Diminished status of folate has been associated with enhanced risk of colon cancer. |

Figure 25:
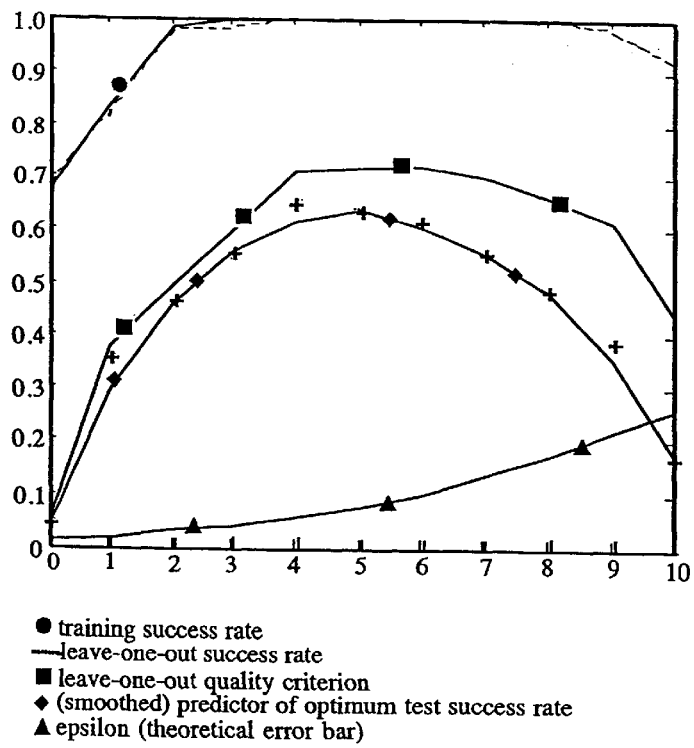
FIG. 25 shows the results of SVM RFE when training on the entire data set.

FIG. 25 shows the results of the methods of the present invention using SVM RFE after training on the whole data set. In FIG. 25, the graph is as follows: Horizontal axis=log2(number of gene cluster centers). Curves: solid circle=training success rate; dashed black=leave-one-out success rate; square=leave-one-out quality criterion; triangle=epsilon (theoretical error bar); diamond=square–triangle (smoothed) predictor of optimum test success rate the optimum of the diamond curve is at log2(num genes)=5→num genes=32.

Figure 26:
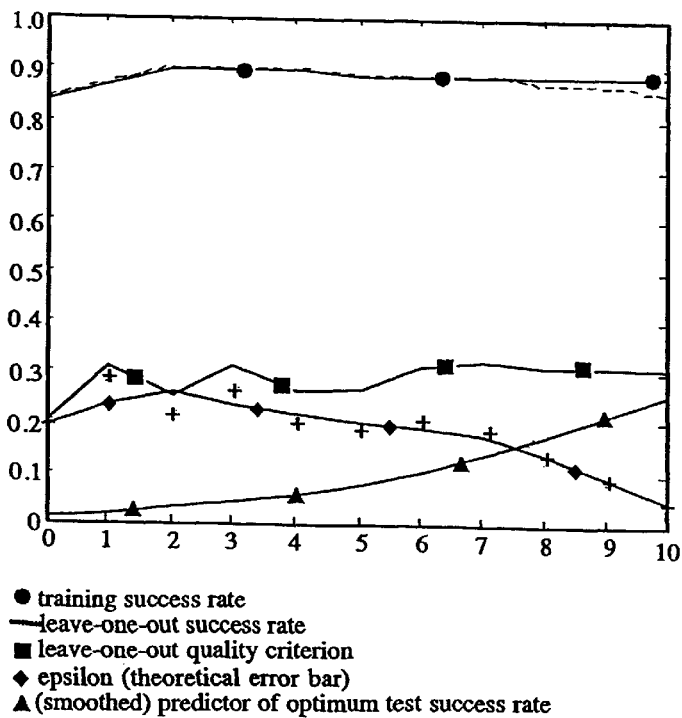
FIG. 26 shows the results of Golub's method when training on the entire data set.

For comparison, FIG. 26 shows the results obtained with Golub's method when training on the entire data set. Horizontal axis=log2(number of gene cluster centers). Curves: circle=training success rate; dashed black=leave-one-out success rate; square=leave-one-out quality criterion; triangle=epsilon (theoretical error bar); diamond=square–triangle (smoothed) predictor of optimum test success rate the optimum of the diamond curve is at log2(num genes)=2→num genes=4.

The best leave-one-out performance is 100% accuracy for SVMs and only 90% for Golub's method (6 errors={39, 29, 1, –12, –35, –29}). Using the statistical test that determines with what confidence (1–α) that one classifier is better than the other, using the formula:

$$(1-\alpha) = 0.5 + 0.5 \ \mathrm{erf}(z_\alpha/\mathrm{sqrt}(2))$$

$$z_\alpha = \epsilon n/\mathrm{sqrt}(v)$$

where n is the number of test examples, v is the total number of errors that only one of the 2 classifiers makes, and ϵ is the difference in error rate. (or in rejection rate)

The methods of the present invention are better than Golub with a 99.3% confidence rate.

Figure 27:
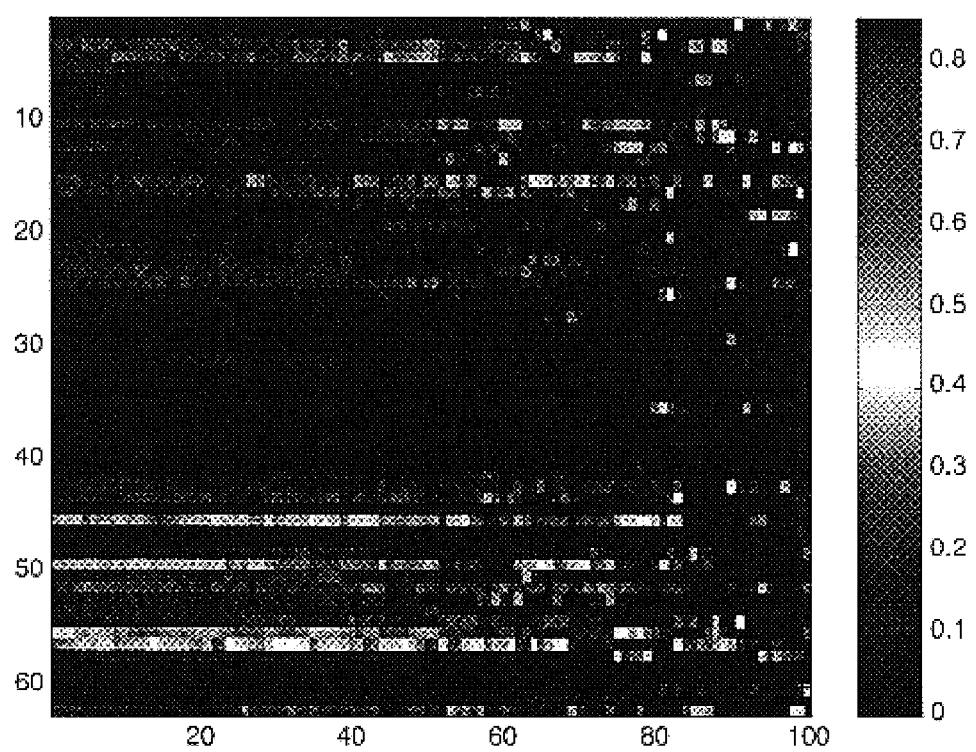
FIG. 27 shows the weighting coefficients of the support vectors.

The optimum number of genes predicted by our leave-one-out criterion is 32 genes in FIG. 25. A finer plot in the small number of genes area reveals an optimum at 21 genes. FIG. 27 shows the weighting coefficients of the support vectors (the "alpha's") in the last 100 iterations of SVM RFE. The alpha vectors have been normalized. It is interesting to see that the alphas do not vary much until the very last iterations. The number of support vectors goes through a minimum at 7 genes for 7 support vectors.

In Table 5, we show the "muscle index" values of these 7 support vectors. The muscle index is a quantity computed by Alon et al on all samples that reflects the muscle cell contents of a sample. Most normal samples have a higher muscle index than tumor samples. However, the support vectors do not show any such trend.

There is a mix of normal and cancer samples with either high or low muscle index.

More importantly, an analysis of the genes discovered reveals that the first smooth muscle gene ranks 5 for Golub's method and only 41 for SVMs. Furthermore, the optimum number of genes for SVM predcted is 32 genes on a log plot and 21 genes on a linear plot. Therefore, SVMs were able to avoid relying on tissue composition-related genes to perform the separation. As confimerd by biological data, the top ranking genes discovered by SVMs are all related to cancer vs. normal separation. In contrast, Golub's method selects genes that are related to tissue composition and not to the distinction of cancer vs. normal in its top ranking genes.

TABLE 5

Muscle index of the support vectors of the SVM trained on the top 7 genes selected by SVM RFE. Samples with a negative sign are tumor tissues. Samples with positive signs are normal tissues. Samples were ranked in ordered of increasing muscle index. In most samples in the data set, normal tissues have higher muscle index than tumor tissues because tumor tissues are richer in epithelial (skin) cells. This was not the case for support vectors which show a mix of all possibilities.

| Sample | –6 | 8 | 34 | –37 | 9 | –30 | –36 |
|---|---|---|---|---|---|---|---|
| Muscle index | 0.009 | 0.2 | 0.2 | 0.3 | 0.3 | 0.4 | 0.7 |

In Table 6, the 7 top ranked genes discovered by the present invention and the genes that clustered to them at threshold θ=0.75. The same was done with Golub's method in Table 7. FIGS. 28 and 29 graphically display those genes.

FIGS. 28A, 28B, and 28C show the top ranked genes discovered by SVM RFE in order of increasing importance from left to right. The gene expression of all 62 tissues (columns) for the 7 clusters (lines) are represented. The top 22 tissues are normal, the 40 last ones are cancerous. Positive gene expressions are red and negative gene expressions are blue. Small values have lighter color. 28A shows cluster centers. 28B shows output of the SVM (weighted sum of the genes of A). The separation is errorless. The genes of FIGS. 28A, 28B and 28C do not look as orderly as those of FIGS. 29A, 29B and 29C because they are individually less correlated with the target separation, although together they carry more information. 28C shows genes clustered to the centers at threshold θ=0.75.

FIGS. 29A, 29B and 29C show the 7 top ranked genes discovered by Golub's methods in order of increasing improtance from left to right. The gene expression of all 62 tissues (columns) for the 7 clusters (lines) are represented. The top 22 tissues are normal, the 40 last ones are cancerous. Positive gene expressions are red and negative gene expressions are blue. Small values have lighter color. 29A shows cluster centers. 29B shows output of the Golub classifier (weighted sum of the genes of A). The separation is not errorless. 29C shows genes clustered to the centers at threshold θ=0.75.s

TABLE 6

SVM top ranked clusters when using all 62 tissues. Clusters are built around the best genes with threshold θ = 0.75.The higher the cluster rank (Rk), the more "relevant" the cluster should be. Min correl is the minimum correlation coefficient between cluster elements. Sgn: sign of correlation with the target separation, − for over-expressed in most cancer tissues; + for over-expressed in most normal tissues; GAN: Gene Accession Number. The cluster centers are preceded by a star. None of the genes seem to be tissue composition related.

| Rk | Min correl | Sgn | GAN | Description |
|---|---|---|---|---|
| 1 | 0.75 | − | *H08393 | COLLAGEN ALPHA 2(XI) CHAIN (*Homo sapiens*) |
|  |  | − | T48804 | 40S RIBOSOMAL PROTEIN S24 (HUMAN) |
|  |  | − | T51529 | ELONGATION FACTOR 1-DELTA (*Artemia salina*) |
| 2 | 0.61 | − | *M59040 | Human cell adhesion molecule (CD44) mRNA, complete cds. |
|  |  | − | H04802 | DIHYDROPYRIDINE-SENSITIVE L-TYPE, SKELETAL MUSCLE CALCIUM CHANNEL GAMMA SUBUNIT (*Homo sapiens*) |
|  |  | − | T65740 | SINGLE-STRANDED DNA BINDING PROTEIN P9 PRECURSOR (*Mus musculus*) |
|  |  | − | L39874 | *Homo sapiens* deoxycytidylate deaminase gene, complete cds. |
|  |  | − | R44740 | DUAL SPECIFICITY MITOGEN-ACTIVATED PROTEIN KINASE KINASE 1 (*Xenopus laevis*) |
| 3 | 0.54 | − | *T94579 | Human chitotriosidase precursor mRNA, complete cds. |
|  |  | − | T63539 | INHIBIN BETA A CHAIN PRECURSOR (*Mus musculus*) |
|  |  | − | T54360 | GRANULINS PRECURSOR (HUMAN). |
|  |  | + | X17273 | Human HLA G (HLA 6.0) mRNA for non classical class I transplantation antigen. |
|  |  | + | T57882 | MYOSIN HEAVY CHAIN, NONMUSCLE TYPE A (*Homo sapiens*) |
|  |  | − | R89377 | NEDD5 PROTEIN (*Mus musculus*) |
|  |  | − | M19283 | Human cytoskeletal gamma-actin gene, complete cds. |
|  |  | − | T83361 | GAMMA INTERFERON INDUCED MONOKINE PRECURSOR (*Homo sapiens*) |
|  |  | − | H66786 | ESTROGEN SULFOTRANSFERASE (*Bos taurus*) |
|  |  | − | T51849 | TYROSINE-PROTEIN KINASE RECEPTOR ELK PRECURSOR (*Rattus norvegicus*) |
|  |  | − | T86444 | PROBABLE NUCLEAR ANTIGEN (*Pseudorabies virus*) |
| 4 | 1 | + | *H81558 | PROCYCLIC FORM SPECIFIC POLYPEPTIDE B1-ALPHA PRECURSOR (*Trypanosoma brucei brucei*) |
| 5 | 0.81 | + | *R88740 | ATP SYNTHASE COUPLING FACTOR 6, MITOCHONDRIAL PRECURSOR (HUMAN);. |
|  |  | + | T54670 | P13621 ATP SYNTHASE OLIGOMYCIN SENSITIVITY CONFERRAL PROTEIN PRECURSOR, MITOCHONDRIAL. |
| 6 | 0.61 | − | *T62947 | 60S RIBOSOMAL PROTEIN L24 (*Arabidopsis thaliana*) |
|  |  | − | T61609 | LAMININ RECEPTOR (HUMAN);. |
|  |  | − | T70062 | Human nuclear factor NF45 mRNA, complete cds. |
|  |  | − | U14971 | Human ribosomal protein S9 mRNA, complete cds. |
|  |  | − | T57619 | 40S RIBOSOMAL PROTEIN S6 (*Nicotiana tabacum*) |
|  |  | − | U30825 | Human splicing factor SRp30c mRNA, complete cds. |
|  |  | − | L10284 | *Homo sapiens* integral membrane protein, calnexin, (IP90) mRNA, complete cds. |
|  |  | − | D00763 | PROTEASOME COMPONENT C9 (HUMAN);. |
|  |  | − | T58861 | 60S RIBOSOMAL PROTEIN L30E (*Kluyveromyces lactis*) |
| 7 | 1 | + | *H64807 | PLACENTAL FOLATE TRANSPORTER (*Homo sapiens*) |

TABLE 7

Golub top ranked clusters when using all 62 tissues. Clusters are built around the best genes with threshold θ = 0.75.The higher the cluster rank (Rk), the more "relevant" the cluster should be. Min correl is the minimum correlation coefficient between cluster elements. Sgn: sign of correlation with the target separation, − for over-expressed in most cancer tissues; + for over-expressed in most normal tissues; GAN: Gene Accession Number. The cluster centers are preceded by a star. The highlighted genes are genes that may be tissue composition related.

| Rk | Min correl | Sgn | GAN | Description |
|---|---|---|---|---|
| 1 | 0.66 | + | *H06524 | GELSOLIN PRECURSOR, PLASMA (HUMAN);. |
|  |  | + | X55187 | Human mRNA for alpha-actinin, partial cds. |
|  |  | + | X68277 | *H.sapiens* CL 100 mRNA for protein tyrosine phosphatase. |
|  |  | + | X74295 | *H.sapiens* mRNA for alpha 7B integrin. |
|  |  | + | X86693 | *H.sapiens* mRNA for hevin like protein. |
| 2 | 0.59 | − | *X12671 | Human gene for heterogeneous nuclear ribonucleoprotein (hnRNP) core protein A1. |
|  |  | − | T57630 | S34195 RIBOSOMAL PROTEIN L3-. |
|  |  | − | T57633 | 40S RIBOSOMAL PROTEIN S8 (HUMAN). |
|  |  | − | L41559 | *Homo sapiens* pterin-4a-carbinolamine dehydratase (PCBD) mRNA, complete cds. |
|  |  | − | D31885 | Human mRNA (KIAA0069) for ORF (novel proetin), partial cds. |
|  |  | − | U26312 | Human heterochromatin protein HP1Hs-gamma mRNA, partial cds. |
| 3 | 0.52 | + | *J02854 | MYOSIN REGULATORY LIGHT CHAIN 2, SMOOTH MUSCLE ISOFORM (HUMAN);contains element TAR1 repetitive element;. |
|  |  | + | X12496 | Human mRNA for erythrocyte membrane sialoglycoprotein beta (glycophorin C). |
|  |  | + | T60778 | MATRIX GLA-PROTEIN PRECURSOR (*Rattus norvegicus*) |
|  |  | + | R78934 | ENDOTHELIAL ACTIN-BINDING PROTEIN (*Homo sapiens*) |
|  |  | + | T60155 | ACTIN, AORTIC SMOOTH MUSCLE (HUMAN) |
|  |  | + | T67077 | SODIUM/POTASSIUM-TRANSPORTING ATPASE GAMMA CHAIN (*Ovis aries*) |
|  |  | − | X14958 | Human hmgI mRNA for high mobility group protein Y. |
|  |  | − | M26697 | Human nucleolar protein (B23) mRNA, complete cds. |
|  |  | + | T92451 | TROPOMYOSIN, FIBROBLAST AND EPITHELIAL MUSCLE-TYPE (HUMAN);. |

TABLE 7-continued

Golub top ranked clusters when using all 62 tissues.
Clusters are built around the best genes with threshold θ = 0.75. The higher the cluster rank (Rk), the more "relevant" the cluster should be. Min correl is the minimum correlation coefficient between cluster elements. Sgn: sign of correlation with the target separation, - for over-expressed in most cancer tissues; + for over-expressed in most normal tissues; GAN: Gene Accession Number. The cluster centers are preceded by a star. The highlighted genes are genes that may be tissue composition related.

| Rk | Min correl | Sgn | GAN | Description |
|---|---|---|---|---|
| | | - | M22382 | MITOCHONDRIAL MATRIX PROTEIN P1 PRECURSOR (HUMAN);. |
| 4 | 0.47 | + | *M63391 | Human desmin gene, complete cds. |
| | | + | U19969 | Human two-handed zinc finger protein ZEB mRNA, partial cds. |
| | | + | X12369 | TROPOMYOSIN ALPHA CHAIN, SMOOTH MUSCLE (HUMAN);. |
| | | + | Z49269 | H.sapiens gene for chemokine HCC-1. |
| | | + | Z49269 | H.sapiens gene for chemokine HCC-1. |
| | | - | T86473 | NUCLEOSIDE DIPHOSPHATE KINASE A (HUMAN);. |
| | | + | M76378 | Human cysteine-rich protein (CRP) gene, exons 5 and 6. |
| | | + | M76378 | Human cysteine-rich protein (CRP) gene, exons 5 and 6. |
| 5 | 0.63 | + | *M36634 | Human vasoactive intestinal peptide (VIP) mRNA, complete cds. |
| | | + | R48303 | TYROSINE RICH ACIDIC MATRIX PROTEIN (Bos taurus) |
| | | + | H77597 | H.sapiens mRNA for metallothionein (HUMAN);. |
| | | + | R44301 | MINERALOCORTICOID RECEPTOR (Homo sapiens) |
| 6 | 0.81 | + | *Z50753 | H.sapiens mRNA for GCAP-II/uroguanylin precursor. |
| | | + | D25217 | Human mRNA (KIAA0027) for ORF, partial cds. |
| 7 | 0.68 | + | *R87126 | MYOSIN HEAVY CHAIN, NONMUSCLE (Gallus gallus) |
| | | - | X54942 | H.sapiens ckshs2 mRNA for Cks1 protein homologue. |
| | | + | M76378 | Human cysteine-rich protein (CRP) gene, exons 5 and 6. |

As a feature selection method, SVM RFE differed from Golub's method in two respects: the mutual information between features was used by SVMs while Golub's method makes implicit independence assumptions; and the decision function was based only on support vectors that are "borderline" cases as opposed to being based on all examples in an attempt to characterize the "typical" cases. The use of support vectors is critical in factoring out irrelevant tissue composition related genes. SVM RFE was compared with RFE methods using other linear discriminant functions that do not make independence assumptions but attempt to characterize the "typical" cases. Two discriminant functions were chosen:

Fisher linear discriminant also called Linear Discriminant Analysis (LDA) (see e.g. Duda, 1973) because Golub's method approximates Fisher's linear discriminant by making independence assumptions, and Mean-Squared-Error (MSE) linear discriminant computed by Pseudo-inverse (see e.g. Duda, 1973) because when all training examples are support vectors the pseudo-inverse solution is identical to the SVM solution.

Figure 30:
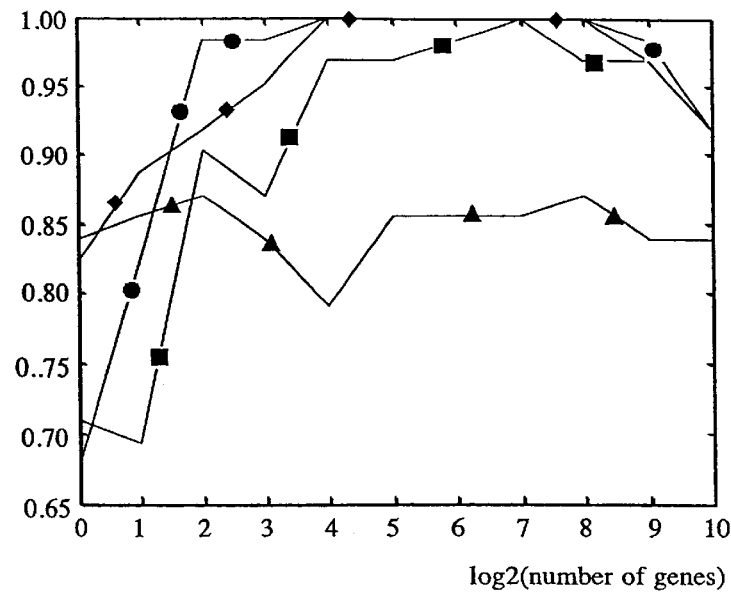
FIG. 30 shows a comparison of feature (gene) selection methods for colon cancer data using different methods.

The results of comparison of feature (gene) selection methods for colon cancer data are shown in FIG. 30. The number of genes selected by Recursive Feature Elimination (RFE) was varied and was tested with different methods. Training was done on the entire data set of 62 samples. The curves represent the leave-one-out success rate. The different methods are shown in FIG. 30 and the graph is described by lines having the elements as follows: Circle: SVM RFE. Square: Linear Discriminant Analysis RFE. Diamond: Mean Squared Error (Pseudo-inverse) RFE. Triangle: Baseline method (Golub, 1999). SVM RFE gives the best results down to 4 genes. An examination of the genes selected reveals that SVM eliminates genes that are tissue composition-related and keeps only genes that are relevant to the cancer vs. normal separation. Conversely, other methods keep smooth muscle genes in their top ranked genes which helps in separating most samples but is not relevant to the cancer vs. normal discrimination.

All methods that do not make independence assumptions outperform Golub's method and reach 100% leave-one-out accuracy for at least one value of the number of genes. LDA may be at a slight disadvantage on these plots because, for computational reasons, RFE was used by eliminating chunks of genes that decrease in size by powers of two. Other methods use RFE by eliminating one gene at a time.

Down to 4 genes, SVM RFE showed better performance than all the other methods. All the methods predicted with the criterion of the equation: $C=Q-2\ \epsilon(d)$; an optimum number of genes smaller or equal to 64. The genes ranking 1 through 64 for all the methods studied were compared. The first gene that was related to tissue composition and mentions "smooth muscle" in its description ranks 5 for Golub's method, 4 for LDA, 1 for MSE and only 41 for SVM. Therefore, this was a strong indication that SVMs make a better use of the data than the other methods. They are the only methods tested that effectively factors out tissue composition related genes while providing highly accurate separations with a small subset of genes.

Figure 35:
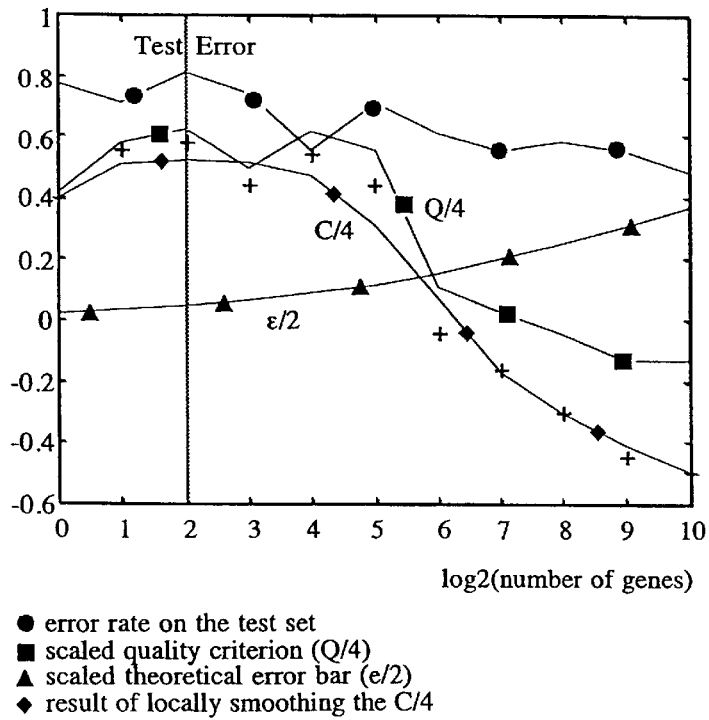
FIG. 35 shows the selection of an optimum number of genes for colon cancer data.

FIG. 35 shows the selection of an optimum number of genes for colon cancer data. The number of genes selected by recursive gene elimination with SVMs was varied. The lines of the graph are as follows: Circle: error rate on the test set. Square: scaled quality criterion (Q/4). Crosses: scaled criterion of optimality (C/4). Diamond curve: result of locally smoothing the C/4. Triangle: scaled theoretical error bar ($\epsilon/2$). The curves are related by $C=Q-2\epsilon$. The dashed line indicates the optimum of the green curve, which is the theoretically predicted optimum, based on training data only: $2^2=4$ genes.

The model selection criterion was established using leukemia data, its predictive power was correlated by using it on colon cancer data, without making any adjustment. The criterion also predicted the optimum accurately. The performance was not as accurate on that first trial because the same preprocessing as for the leukemia data of Example 2 was used. The results were improved substantially by adding several preprocessing steps and reached a success rate of 90% accuracy. These preprocessing steps included taking the logarithm of all values, normalizing sample vectors, normalizing feature vectors, and passing the result through a squashing function to diminish the importance of outliers. Normalization comprised subtracting the mean over all training values and dividing by the corresponding standard deviation.

The model selection criterion was used in a variety of other experiments using SVMs and other algorithms. The optimum number of genes was always predicted accurately, within a factor of two of the number of genes.

Results Correlated with the Biology Literature

SVM RFE eliminated from its top ranked genes the smooth muscle genes that are likely to be tissue composition related. The cancer related genes were limited to seven for convenience reasons. Additionally, the number seven corresponds to the minimum number of support vectors, a criterion also sometimes used for "model selection".

The best ranked genes code for proteins whose role in colon cancer has been long identified and widely studied. Such is the case of CD44, which is upregulated when colon adenocarcinoma tumor cells transit to the metastatic state (Ghina, 1998) and collagen which is involved in cell adhesion. Colon carcinoma cells have collagen degrading activity as part of the metastatic process (Karakiulakis, 1997). ATP synthase as an enzyme that helps build blood vessels to feed the tumors was published only a year ago (Mozer, 1999). Diminished status of folate has been associated with enhanced risk of colon cancer in a recent clinical study (Walsh, 1999). To this date, no known biochemical mechanism explains the role of folate in colon cancer. Knowing that gene H64807 (Placental folate transporter) was identified as one of the most discriminant genes in the colon cancer vs. normal separation shows the use of the methods of the present invention for identifying genes involved in biological changes.

In the case of human chitotriosidase, one needs to proceed by analogy with another homologous protein of the same family whose role in another cancer is under study: another chitinase (BRP39) was found to play a role in breast cancer. Cancer cells overproduce this chitinase to survive apoptosis (Aronson, 1999). Important increased chitotriosidase activity has been noticed in clinical studies of Gauchers disease patients, an apparently unrelated condition. To diagnose that other disease the chitotriosidase enzyme can be very sensitively measured. The plasma or serum prepared from less than a droplet of blood is highly sufficient for the chitotriosidase measurement (Aerts, 1996). This opens the door to a possible new diagnosis test for colon cancer as well.

The 60S ribosomal protein L24 (Arabidopsis thaliana) is a non-human protein that is homologous a human protein located on chromosome 6. Like other ribosomal proteins, it may play a role in controlling cell growth and proliferation through the selective translation of particular classes of mRNA.

A surprisingly novel finding is the identified gene for "procyclic form specific polypeptide B1-alpha precursor (Trypanosoma brucei brucei)". Trypanosoma is a parasitic protozoa indigenous to Africa and South America and patients infected by Trypanosoma (a colon parasite) develop resistance against colon cancer (Oliveira, 1999). Trypanosomiasis is an ancient disease of humans and animals and is still endemic in Africa and South America.

EXAMPLE 2

Leukemia Gene Discovery

The data set, which consisted of a matrix of gene expression vectors obtained from DNA microarrays, was obtained from cancer patients with two different types of leukemia. The data set was easy to separate. After preprocessing, it was possible to find a weighted sum of a set of only a few genes that separated without error the entire data set, thus the data set was linearly separable. Although the separation of the data was easy, the problems present several features of difficulty, including small sample sizes and data differently distributed between training and test set.

In Golub, 1999, the authors present methods for analyzing gene expression data obtained from DNA micro-arrays in order to classify types of cancer. The problem with the leukemia data was the distinction between two variants of leukemia (ALL and AML). The data is split into two subsets: A training set, used to select genes and adjust the weights of the classifiers, and an independent test set used to estimate the performance of the system obtained. Golub's training set consisted of 38 samples (27 ALL and 11 AML) from bone marrow specimens. Their test set has 34 samples (20 ALL and 14 AML), prepared under different experimental conditions and including 24 bone marrow and 10 blood sample specimens. All samples have 7129 attributes (or features) corresponding to some normalized gene expression value extracted from the micro-array image. In this. Example, the exact same experimental conditions were retained for ease of comparison with their method.

In preliminary experiments, some of the large deviations between leave-one-out error and test error could not be explained by the small sample size alone. The data analysis revealed that there are significant differences between the distribution of the training set and the test set. Various hypotheses were tested and it was found that the differences can be traced to differences in data source. In all the experiments, the performance on test data from the various sources was followed separately. The results obtained were the same, regardless of the source.

Figure 31:
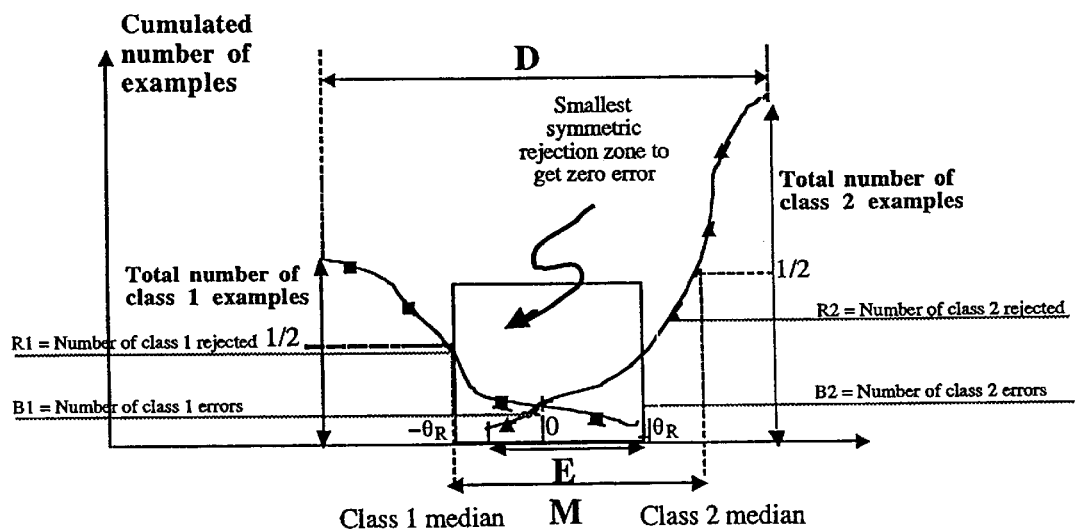
FIG. 31 shows the metrics of classifier quality. The triangle and circle curves represent example distributions of two classes: class 1 (negative class) and class 2 (positive class).

In Golub, the authors use several metrics of classifier quality, including error rate, rejection rate at fixed threshold, and classification confidence, as described in Example 1. See FIG. 31 which shows the metrics of classifier quality. The curves (square and triangle) represent example distributions of two classes: class 1 (negative class) and class 2 (positive class). Square: Number of examples of class 1 whose decision function value is larger than or equal to θ. Triangle: Number of examples of class 2 whose decision function value is smaller than or equal to θ. The number of errors B1 and B2 are the ordinates of θ=0. The number of rejected examples R1 and R2 are the ordinates of $-\theta_R$ and $\theta_R$ in the triangle and circle curves respectively. The decision function value of the rejected examples is smaller than $\theta_R$ in absolute value, which corresponds to examples of low classification confidence. The threshold $\theta_R$ is set such that all the remaining "accepted" examples are well classified. The extremal margin E is the difference between the smallest decision function value of class 2 examples and the largest decision function value of class 1 examples. On the example of the figure, E is negative. If the number of classification error is zero, E is positive. The median margin M is the difference between the median decision function value of the class 1 density and the median of the class 2 density.

In a first set of experiments, SVMs were compared with the baseline system of Golub et al on the leukemia data (Golub, 1999). A simple preprocessing step was performed. For each gene expression value, the mean was subtracted and the result was divided by its standard deviation.

Two experiments were conducted. First, the full set of 7129 genes (Table 8) was used. The measured values were as described earlier.

TABLE 8

Results of training classifiers on all genes (Leukemia data).
A set of 50 genes corresponding to the largest weights of the SVM trained
on all genes was selected. A new SVM was trained on these 50 genes. We
compared the results with the baseline system trained with the original set of
50 features reported the Golub et al paper (Table 9).

| | Leave-one-out (38 samples) | | | | Test set (34 samples) | | | |
|---|---|---|---|---|---|---|---|---|
| Classifier | Error # (0 reject) | Reject # (0 error) | Extremal margin | Median margin | Error # (0 reject) | Reject # (0 error) | Extremal margin | Median margin |
| SVM | 2 | 5 | 0.01 | 0.42 | 5 | 11 | −0.05 | 0.42 |
| Baseline | 4 | 20 | −0.25 | 0.28 | 5 | 22 | −0.24 | 0.34 |

A set of 50 genes was then selected. The 50 genes corresponded to the largest weights of the SVM trained on all genes. A new SVM was trained on these 50 genes. The results were compared with the baseline system trained with the original set of 50 features reported in the Golub et al. paper. See Table 9.

TABLE 9

Results of training on 50 genes (Leukemia data).

| | Leave-one-out (38 samples) | | | | Test set (34 samples) | | | |
|---|---|---|---|---|---|---|---|---|
| Classifier | Error # (0 reject) | Reject # (0 error) | Extremal margin | Median margin | Error # (0 reject) | Reject # (0 error) | Extremal margin | Median margin |
| SVM | 0 | 0 | 0.21 | 0.54 | 0 | 0 | 0.03 | 0.40 |
| Baseline | 0 | 0 | 0.04 | 0.41 | 1 | 5 | −0.09 | 0.49 |

In both cases, SVMs matched the performance of the baseline system or outperformed it. Using the detailed results of Tables 10 and 11, the statistical significance of the performance differences was checked with the following equation:

$$(1-\alpha)=0.5+0.5 \, \text{erf}(z_\alpha/\text{sqrt}(2))$$

$$z_\alpha=\epsilon n/\text{sqrt}(v)$$

TABLE 10

Detailed results of training on all genes (Leukemia data). The error id numbers are in brackets.

| | Test set (34 samples) | |
|---|---|---|
| Classifier | Error # (0 reject) | Reject # (0 error) |
| SVM | 5 {16,19,22,23,28} | 11 {2,4,14,16,19,20,22,23,24,27,28} |
| Baseline | 5 {16,19,22,27,28} | 22 {1,2,4,5,7,11,13,14,16–20,22–29,33} |

TABLE 11

Detailed results of training on 50 genes(Leukemia data) The error id numbers are in brackets.

| | Test set (34 samples) | |
|---|---|---|
| Classifier | Error # (0 reject) | Reject # (0 error) |
| SVM | 0 | 0 |
| Baseline | 1 {28} | 5 {16,22,23,28,29} |

According to the results of the test, the classifiers trained on 50 genes are better than those trained on all genes with high confidence (based on the error rate 97.7% confidence for Golub and 98.7% for SVM). Based on the error rate alone, the SVM classifier is not significantly better than the Golub classifier (50% confidence on all genes and 84.1% confidence on 50 genes). But, based on the rejections, the SVM classifier is significantly better than the Golub classifier (99.9% confidence on all genes and 98.7% confidence on 50 genes).

In a second set of experiments, a more in-depth comparison between the method of Golub et al and SVMs on the leukemia data was made. In particular, two aspects of the problem were de-coupled: selecting a good subset of genes and finding a good decision function. The performance improvements obtained with SVMs can be traced to the SVM feature (gene) selection method. The particular decision function that was trained with these features mattered less than selecting an appropriate subset of genes.

Rather than ranking the genes once with the weights of an SVM classifier as was done in the first set of experiments, instead, the Recursive Feature Elimination (RFE) method was used. At each iteration, a new classifier is trained with the remaining features. The feature corresponding to the smallest weight in the new classifier is eliminated. The order of elimination yields a particular ranking. By convention, the last feature to be eliminated is ranked first. Chunks of genes were eliminated at a time. At the first iteration, the number of genes which is the closest power of 2 were reached. At subsequent iterations, half of the remaining genes were eliminated. Nested subsets of genes of increasing informative density were obtained.

The quality of these subsets of genes was then assessed by training various classifiers, including a regular SVM, the Golub et al classifier, and Fisher's linear discriminant (see e.g. (Duda, 1973)). An SVM trained after projecting the data along the first principal component of the training examples was also used. This amounts to setting a simple bias value, which was placed at the center of gravity of the two extreme examples of either class, weighted by the number of examples per class. This classifier was called a "reduced-capacity-SVM".

Figure 32A:
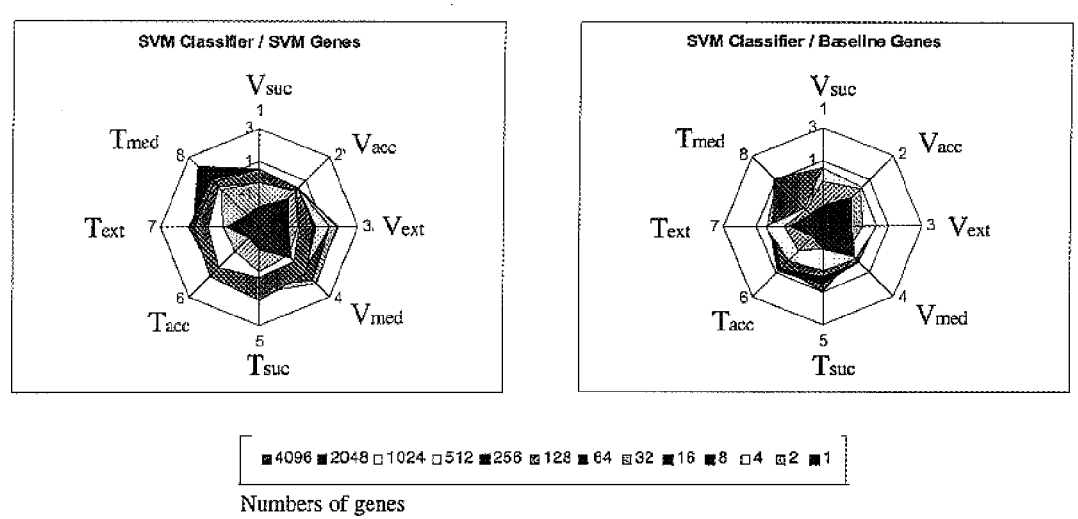
FIGS. 32A and 32B show the performance comparison between SVMs and the baseline method for leukemia data.
Figure 32B:
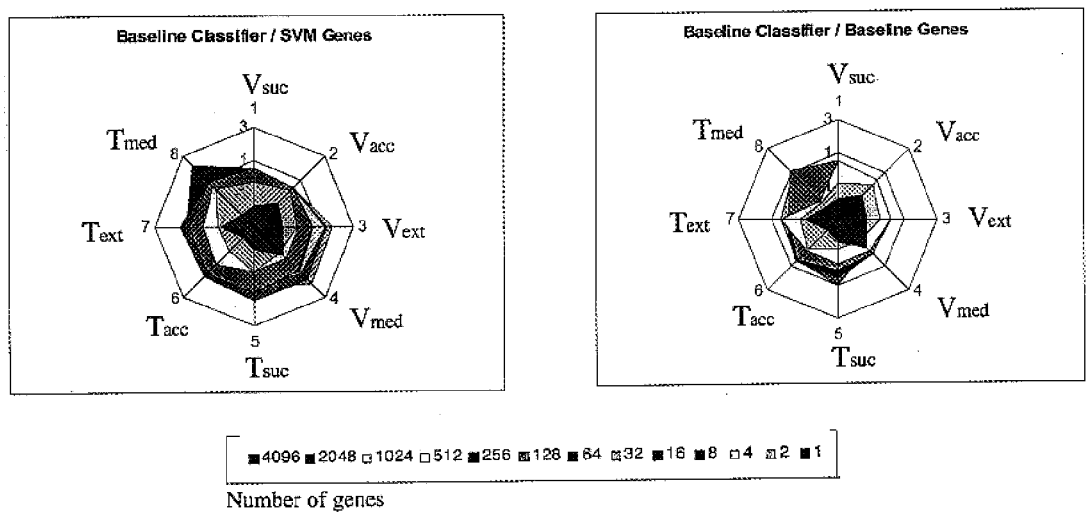

The various classifiers that were tried did not yield significantly different performance. The results of the classifier of Golub, 1999 and the reduced-capacity-SVM were reported herein. Several cross tests were performed with the baseline method to compare gene sets and classifiers. See FIG. 32A which show SVMs trained on SVM selected genes or on baseline genes and FIG. 32B which shows a baseline classifier trained on SVM selected genes or on baseline genes. Classifiers have been trained with subsets of genes selected with SVMs and with the baseline method on the training set of the Leukemia data. The number of genes is color coded and indicated in the legend. The quality indicators are plot radially: channel 1–4=cross-validation results with the leave-one-out method; channels 5–8=test set results; suc=success rate; acc=acceptance rate; ext=extremal margin; med=median margin. The coefficients have been rescaled such that the average value of each indicator has zero mean an variance 1 across all four plots. For each classifier, the larger the colored area, the better the classifier. The figure shows that there is no significant difference between classifier performance on this data set, but there is a significant difference between the gene selections.

In Table 12, the best results obtained on the test set for each combination of gene selection and classification method are summarized. The classifiers give identical results, given a gene selection method. In contrast, the SVM selected genes yield consistently better performance than the baseline genes for both classifiers. The significance of the difference was tested with the following equation:

$$(1-\alpha)=0.5+0.5 \ \mathrm{erf}(z_\alpha/\mathrm{sqrt}(2))$$

$$z_\alpha=\epsilon n/\mathrm{sqrt}(v)$$

Whether SVM or baseline classifier, SVM genes were better with 84.1% confidence based on test error rate and 99.2% based on the test rejection rate.

TABLE 12

Best classifier on test data (Leukemia data). The performance of the classifiers performing best on test data are reported. For each combination of SVM or Baseline genes and SVM or Baseline classifier, the corresponding number of genes, the number of errors and the number of rejections are shown in the table. The patient id numbers are shown in bracket.

| Genes Classifier | SVM | | | Baseline | | |
|---|---|---|---|---|---|---|
| | # genes | Error # | Reject # | # genes | Error # | Reject # |
| SVM | 8, 16 | 0 {} | 0 {} | 64 | 1 {28} | 6 {4,16,22,23,28,29} |
| Baseline | 64 | 0 {} | 0 {} | 64 | 1 {28} | 6 {4,16,22,23,28,29} |

To compare the top ranked genes, the fraction of common genes in the SVM selected subsets and the baseline subsets (Table 13) were computed. At the optimum number of 16 genes found for SVMs in this example, only 19% of the genes were common.

TABLE 13

Fraction of common genes between the sets selected with the baseline method and SVM recursive gene elimination (Leukemia data). The fraction of common genes decreases approximately exponentially as a function of the number of genes (linearly in a log scale). Only 19% of the genes were common at the optimum SVM gene set number 16.

| Number of genes | Fraction of common genes (percent) |
|---|---|
| All 7129 | 100 |
| 4096 | 71 |
| 2048 | 60 |
| 1024 | 55 |
| 512 | 40 |
| 256 | 39 |
| 128 | 32 |
| 64 | 33 |
| 32 | 28 |
| 16 | 19 |
| 8 | 25 |
| 4 | 25 |
| 2 | 0 |
| 1 | 0 |

FIGS. 33A, 33B, 33C and 33D show the best set of 16 genes for the leukemia data. In matrices (a) and (c), the columns represent different genes and the lines different patients from the training set. The 27 top lines are ALL patients and the 11 bottom lines are AML patients. The gray shading indicates gene expression: the lighter the stronger. 33A shows SVM best 16 genes. Genes are ranked from left to right, the best one at the extreme left. All the genes selected are more AML correlated. 33B shows the weighted sum of the 16 SVM genes used to make the classification decision. A very clear ALL/AML separation is shown. 33C shows baseline method 16 genes. The method imposes that half of the genes are AML correlated and half are ALL correlated. The best genes are in the middle. 33D shows the weighted sum of the 16 baseline genes used to make the classification decision. The separation is still good, but not as good as the SVM separation.s FIGS. 33A and 33C show the expression values for the patients in the training set of the 16 gene subsets. At first sight, the genes selected by the baseline method looked a lot more orderly. This was because they were strongly correlated with either AML or ALL. There was a lot of redundancy in this gene set. In essence, all the genes carried the same information. Conversely, the SVM selected genes carrying complementary information. This was reflected in the output of the decision function (FIG. 33B and 33D) which was a weighted sum of the 16 gene expression values. The SVM output more clearly separated AML patients from ALL patients. Tables 14 and 15 list the genes that were selected by the two methods.

TABLE 14

Top ranked 16 SVM genes (Leukemia data). Rk = rank. GAN = Gene Accession Number. Correlation = gene correlates most with the class listed. The genes were obtained by recursively eliminating the least promising genes. Nested subsets of genes are obtained.

| Rk | GAN | Description | Correlation |
|----|-----|-------------|-------------|
| 1 | U50136-ma1-at | Leukotriene C4 synthase (LTC4S) gene | AML |
| 2 | X95735-at | Zyxin | AML |
| 3 | M27891-at | CST3 Cystatin C (amyloid angiopathy and cerebral hemorrhage) | AML |
| 4 | M23197-at | CD33 antigen (differentiation antigen) | AML |
| 5 | M19507-at | MPO Myeloperoxidase | AML |
| 6 | M68891-at | GATA2 GATA-binding protein 2 | AML |
| 7 | U63289-at | RNA-binding protein CUG-BP/hNab50 (NAB50) mRNA | AML |
| 8 | M20902-at | APOC1 Apolipoprotein C1 | AML |
| 9 | L36847-at | GB DEF = (clone p17/90) rearranged iduronate-2-sulphatase homologue gene | AML |
| 10 | Y00339-s-at | CA2 Carbonic anhydrase II | AML |
| 11 | X70297-at | CHRNA7 Cholinergic receptor, nicotinic, alpha polypeptide 7 | AML |
| 12 | D49950-at | Liver mRNA for interferon-gamma inducing factor(IGIF) | AML |
| 13 | M98399-s-at | CD36 CD36 antigen (collagen type I receptor, thrombospondin receptor) | AML |
| 14 | U43292-at | MDS1B (MDS1) mRNA | AML |
| 15 | M22960-at | PPGB Protective protein for beta-galactosidase (galactosialidosis) | AML |
| 16 | Y07604-at | Nucleoside-diphosphate kinase | AML |

TABLE 15

Top ranked 16 baseline genes (Leukemia data). GAN = Gene Accession Number. Correlation = gene correlates most with the class listed. The 8 genes on the left correlate most with ALL and the 8 genes on the right with AML. The top ones are the best candidates. Golub et al mixed equal proportions of ALL-correlated and AML-correlated genes in their experiments.

| Rank | GAN | Correlation | Rank | GAN | Correlation |
|------|-----|-------------|------|-----|-------------|
| 1 | U22376-cds2-s-at | ALL | 1 | M55150-at | AML |
| 2 | X59417-at | ALL | 2 | U50136-rna1-at | AML |
| 3 | U05259-rna1-at | ALL | 3 | X95735-at | AML |
| 4 | M92287-at | ALL | 4 | M16038-at | AML |
| 5 | X74262-at | ALL | 5 | M23197-at | AML |
| 6 | L13278-at | ALL | 6 | M84526-at | AML |
| 7 | M31211-s-at | ALL | 7 | Y12670-at | AML |
| 8 | U09087-s-at | ALL | 8 | U82759-at | AML |

An Optimum Subset of Genes can be Predicted

The problem of predicting an optimum subset of genes was addressed. The criterion defined in the equation below derived from training examples only was used.

$$C = Q - 2\epsilon(d)$$

Whether the predicted gene subset performed best on the test set was checked. The tests were carried out using SVM Recursive Feature Elimination. The number of features was reduced progressively by a factor of two at every iteration. An SVM classifier was trained on all the intermediate subsets found.

Figure 34:
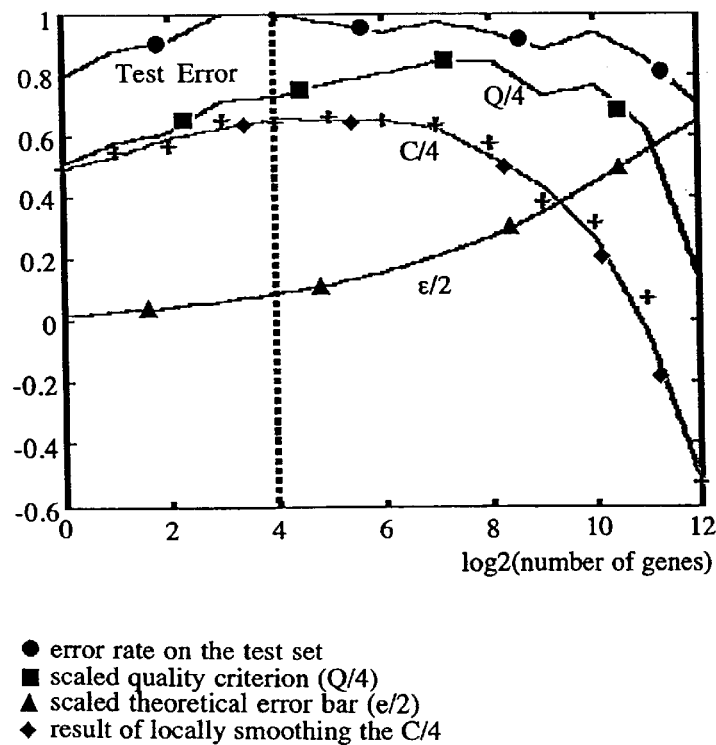
FIG. 34 shows the selection of an optimum number of genes for leukemia data.

As shown in FIG. 34, an optimum number of 16 genes was found. The number of genes selected by recursive gene elimination with SVMs was varied. The description of the lines of the graph is as follows: Circle: error rate on the test set. Square: scaled quality criterion (Q/4). crosses: scaled criterion of optimality (C/4). Diamond curve: result of locally smoothing the C/4. Circle: scaled theoretical error bar ($\epsilon/2$). The curves are related by $C = Q - 2\epsilon$. The dashed line indicates the optimum of the diamond curve, which is the theoretically predicted optimum, based on training data only: $2^4 = 16$ genes. Zero test error is obtained at this optimum.

It turned out that the performance on the test set was also optimum at that value. The details of the results are reported in Table 16.

TABLE 16

SVM classifier trained on SVM genes obtained with the RFE method (Leukemia data). The criterion of classifier selection C was the classifier quality Q minus the error bar $\epsilon$. These quantities were computed based on training data only. The success rate (at zero rejection), the acceptance rate (at zero error), the extreme margin and the median margin were reported for the leave-one-out method on the 38 sample training set (V results) and the 34 sample test set (T results). Where the number of genes was 16 was the best classifier predicted by the locally smoothed C criterion calculated using training data only.

| Num genes | 2 $\epsilon$ | Q | Q-2 $\epsilon$ | Training set (38 samples) | | | | Test set (34 samples) | | | |
|-----------|------|---|------|-------|-------|-------|-------|-------|-------|-------|-------|
| | | | | $V_{suc}$ | $V_{acc}$ | $V_{ext}$ | $V_{med}$ | $T_{suc}$ | $T_{acc}$ | $T_{ext}$ | $T_{med}$ |
| 4096 | 2.59 | 0.50 | -2.09 | 0.82 | 0.05 | -0.67 | 0.30 | 0.71 | 0.09 | -0.77 | 0.34 |
| 2048 | 2.20 | 2.46 | 0.26 | 0.97 | 0.97 | 0.00 | 0.51 | 0.85 | 0.53 | -0.21 | 0.41 |
| 1024 | 1.78 | 3.07 | 1.29 | 1.00 | 1.00 | 0.41 | 0.66 | 0.94 | 0.94 | -0.02 | 0.47 |
| 512 | 1.40 | 2.94 | 1.54 | 0.97 | 0.97 | 0.20 | 0.79 | 0.88 | 0.79 | 0.01 | 0.51 |

TABLE 16-continued

SVM classifier trained on SVM genes obtained with the RFE method (Leukemia data). The criterion of classifier selection C was the classifier quality Q minus the error bar $\epsilon$. These quantities were computed based on training data only. The success rate (at zero rejection), the acceptance rate (at zero error), the extreme margin and the median margin were reported for the leave-one-out method on the 38 sample training set (V results) and the 34 sample test set (T results). Where the number of genes was 16 was the best classifier predicted by the locally smoothed C criterion calculated using training data only.

| Num genes | C = 2$\epsilon$ | Q | Q-2$\epsilon$ | Training set (38 samples) | | | | Test set (34 samples) | | | |
|---|---|---|---|---|---|---|---|---|---|---|---|
| | | | | $V_{suc}$ | $V_{acc}$ | $V_{ext}$ | $V_{med}$ | $T_{suc}$ | $T_{acc}$ | $T_{ext}$ | $T_{med}$ |
| 256 | 1.08 | 3.37 | 2.29 | 1.00 | 1.00 | 0.59 | 0.79 | 0.94 | 0.91 | 0.07 | 0.62 |
| 128 | 0.82 | 3.36 | 2.54 | 1.00 | 1.00 | 0.56 | 0.80 | 0.97 | 0.88 | −0.03 | 0.46 |
| 64 | 0.62 | 3.20 | 2.59 | 1.00 | 1.00 | 0.45 | 0.76 | 0.94 | 0.94 | 0.11 | 0.51 |
| 32 | 0.46 | 3.10 | 2.64 | 1.00 | 1.00 | 0.45 | 0.65 | 0.97 | 0.94 | 0.00 | 0.39 |
| 16 | 0.34 | 2.91 | 2.57 | 1.00 | 1.00 | 0.25 | 0.66 | 1.00 | 1.00 | 0.03 | 0.38 |
| 8 | 0.24 | 2.87 | 2.63 | 1.00 | 1.00 | 0.21 | 0.66 | 1.00 | 1.00 | 0.05 | 0.49 |
| 4 | 0.17 | 2.45 | 2.28 | 0.97 | 0.97 | 0.01 | 0.49 | 0.91 | 0.82 | −0.08 | 0.45 |
| 2 | 0.11 | 2.32 | 2.20 | 0.97 | 0.95 | −0.02 | 0.42 | 0.88 | 0.47 | −0.23 | 0.44 |
| 1 | 0.06 | 2.03 | 1.97 | 0.92 | 0.84 | −0.19 | 0.45 | 0.79 | 0.18 | −0.27 | 0.23 |

At the optimum, the SVM is 100% accurate on the test set, without any rejection.

Comparison results with the baseline system at the predicted optimum are shown in Table 17.

TABLE 17

Best classifier selected with criterion C (Leukemia data). The performance of the classifiers corresponding to the optimum of criterion C, computed solely on the basis of training examples, were reported. For each combination of SVM or Baseline genes and SVM or Baseline classifier, the corresponding number of genes, the number of errors and the number of rejections are shown in the table. The patient id numbers are shown in bracket.

| Genes Classifier | SVM | | | Baseline | | |
|---|---|---|---|---|---|---|
| | # genes | Error # | Reject # | # genes | Error # | Reject # |
| SVM | 16 | 0 {} | 0 {} | 8 | 3 {22, 28,29} | 5 {14,19,22, 28,29} |
| Baseline | 16 | 2 {22,28} | 3 {19, 22,28} | 8 | 3 {19, 22,28} | 6 {14,19,22,23, 28,29} |

The overall difference obtained between the SVM system (optimum SVM classifier trained on SVM features) and the baseline system (optimum baseline classifier trained on baseline features) was quite significant: 95.8% for the error rate and 99.2% for the rejection rate. From cross-test analysis, it was seen that these differences can be traced mostly to a better set of features rather than a better classifier.

The leukemia data was treated by running the gene selection method on the entire data set of 72 samples. The four top ranked genes are shown in Table 18.

TABLE 18

SVM RFE top ranked genes (Leukemia data). The entire data set of 72 samples was used to select genes with SVM RFE. Genes were ranked in order of increasing importance. The first ranked gene is the last gene left after all other genes have been eliminated. Expression: ALL > AML indicates that the gene expression level is higher in most ALL samples; AML > ALL indicates that the gene expression level is higher in most AML samples; GAN: Gene Accession Number. All the genes in this list have some plausible relevance to the AML vs. ALL separation.

| Rk | Expres-sion | GAN | Description | Possible function/relation to Leukemia |
|---|---|---|---|---|
| 4 | AML > ALL | U59632 | Cell division control related protein (hCDCrel-1) mRNA | hCDCrel-1 is a partner gene of MLL in some leukemias (Osaka, 1999). |
| 3 | AML > ALL | U82759 | GB DEF = Homeodomain protein HoxA9 mRNA | Hoxa9 collaborates with other genes to produce highly aggressive acute leukemic disease (Thorsteinsdottir, 1999). |
| 2 | ALL > AML | HG1612 | MacMarcks | Tumor necrosis factor-alpha rapidly stimulate Marcks gene transcription in human promyelocytic leukemia cells (Harlan, 1991). |
| 1 | ALL > ALL | X95735 | Zyxin | Encodes a LIM domain protein localized at focal contacts in adherent erythroleukemia cells (Macalma, 1996). |

The number of four genes corresponds the minimum number of support vectors (5 in this case). All four genes have some relevance to leukemia cancer and can be used for discriminating between AML and ALL variants.

In this last experiment, the smallest number of genes that separate the whole data set without error is two. For this set of genes, there is also zero leave-one-out error, In contrast, Golub's method always yields at least one training error and one leave-one-out error. One training error can be achieved with a minimum of 16 genes and one leave-one-out error with a minimum of 64 genes.

In summary, the fastest methods of feature selection were correlation methods: for the data sets under study, several thousands of genes can be ranked in about one second by the baseline method of Golub with a Pentium processor. The second fastest methods use the weights of a classifier trained only once with all the features as ranking criterion./ Training algorithms such SVMs or Pseudo-inverse/MSE require first the computation of the (n,n) matrix K of all the scalar products between the n training patterns. The computation of K increases linearly with the number of features (gene) and quadratically with the number of training patterns. After that, the training time is of the order of the time to invert matrix K. For optimized SVM algorithms, training may be faster than inverting K, if the number support vectors is small compared to n. For the data sets under study, the solution is found in a couple of seconds on a Pentium processor with non-optimized Matlab code.

Recursive Feature Elimination (RFE) requires training multiple classifiers on subsets of feature of decreasing size. The training time scales linearly with number of classifiers to be trained. Part of the calculations can be reused. Matrix K does not need to be re-computed entirely. The partial scalar products of the eliminated features can be subtracted. Also, the coefficients a can be initialized to their previous value. The Matlab® software (from Math Works, Inc., Natick, Mass.) implementation of an SVM RFE of the present invention on a Pentium processor returns a gene ranking in about 15 minutes for the entire colon dataset (2000 genes, 62 patients) and 3 hours for the leukemia dataset (7129 genes, 72 patients). Given that the data collection and preparation may take several months or years, it is quite acceptable that the data analysis take a few hours.

All of the feature selection experiments using various classifiers (SVM, LDA, MSE) indicated that better features were obtained by using RFE than by using the weights of a single classifier. Similarly, better results were obtained by eliminating one feature at a time than by eliminating chunks of features. However, there are only significant differences for the smaller subset of genes (less than 100). Though not wishing to be bound by any particular theory, it is theorized that, without trading accuracy for speed, one can use RFE by removing chunks of features in the first few iterations and then remove one feature at a time once the feature set reaches a few hundred in number. The RFE algorithm is made sub-linear in the total number of features. This is used in embodiments wherein the number of genes approaches millions, as is expected to happen in the near future.

Other embodiments were employed with the SVM. One embodiment is to formulate the optimization problem so that a large number of weights will be forced to zero. The following linear programming formulation was used:

$$cw_1 + w_1^* + C\Sigma_1 \zeta_1$$

Subject to:

$$y_1[(w^* - w).x + b] \geq 1 - \zeta_1$$

$$w_1 > 0$$

$$w_1^* > 0$$

$$I = 1 \ldots n$$

where C is a positive constant.

SVM RFE improves feature selection based on feature ranking by eliminating the independence assumptions of correlation methods. It generates nested subsets of features. This means that the selected subset of d features is included in the subset of d+1 features. Feature ranking methods may miss a singleton that provides the best possible separation. These is no guarantee that the best feature pair will incorporate that singleton.

Combinatorial search is a computationally intensive alternative to feature ranking. To seek an optimum subset of d features or less, all combinations of d features or less are tried. The combination which yield the best classification performance is selected. One embodiment of the present invention comprises using combinatorial methods.

A combinatorial search was used to refine the optimum feature set, starting with a subset of genes selected with SVM RFE. The leukemia data was used in its training/test data split version. The model selection criterion of the equation $C = Q - 2 \epsilon(d)$. computed with the training dataset only, attempts were made to predict which combination would perform best on test data., The triplet of genes which ranked first provided 100% classification accuracy on both the training set and the test set.

Other embodiments of the present invention comprise use of non-linear classifiers. The SVM RFE of the present invention is used with kernel SVMs with decision functions of the form:

$$D(x) = \Sigma_1 \alpha_1 y_1 K(x_1, x)$$

The ranking criterion used was the weights of vector $w = \Sigma_1 \alpha_1 y_1 x_1$. Note w is not longer the weight vector of the classifier.

Other embodiments of SVM RFE also include use in problems of regression such as medical prognosis and for problems of density estimation or estimation of the support of a density.

Though not wishing to be bound by any particular theory, RFE ranking can be thought of as producing nested subsets of features of increasing size that are optimal in some sense. Individually, a feature that is ranked better than another one may not separate the data better. In fact, there are features with any rank that are highly correlated with the first ranked feature. One way of adding a correlation dimension to the simple linear structure provided by SVM RFE is to cluster genes according to a given correlation coefficient. Unsupervised clustering in pre-processing for SVM RFE was shown in the present application. The cluster centers were then used as features to be ranked. Supervised clustering was also used as a post-processing for SVM RFE. Top ranking features were also used as cluster centers. The remaining rejected features were clustered to those centers.

SVMs lend themselves particularly well to the analysis of broad patterns of gene expression from DNA microarray data. They can easily deal with a large number of features, such as thousands of genes, and a small number of training patterns, such as a small number of patients. Baseline methods were outperformed in only two days work by SVMs.

The two cancer databases showed that not taking into account the mutual information between genes in the process of selecting subsets of genes impairs classification performance. Significant improvements over the baseline methods that make implicit independence assumptions were obtained. The top ranked genes found via SVM were all relevant to cancer. In contrast, other methods selected genes that were correlated with the separation at hand but were nor relevant to cancer diagnosis.

The present invention was demonstrated with linear SVM classifiers, but the present invention comprises non-linear classifiers to regression and to density estimation. Other SVM gene selection methods, such as combinatorial search, are also included in the present invention. Preferred methods of the present invention comprise use of linear classifiers and such classifiers are preferred because of the large ratio number of features over the number training patterns.

It should be understood, of course, that the foregoing relates only to preferred embodiments of the present invention and that numerous modifications or alterations may be made therein without departing from the spirit and the scope of the invention as set forth in the appended claims. Such alternate embodiments are considered to be encompassed within the spirit and scope of the present invention. Accordingly, the scope of the present invention is described by the appended claims and is supported by the foregoing description.

(Alon, et al., 1999) Broad patterns of gene expression revealed by clustering analysis of tumor and normal colon cancer tissues probed by oligonucleotide arrays. PNAS vol. 96 pp. 6745–6750, June 1999, Cell Biology.

(Eisen, M. B., et al., 1998) Cluster analysis and display of genome-wide expression patterns *Proc. Natl. Acad. Sci. USA*, Vol. 95, pp. 14863–14868, December 1998, Genetics.

(Alizadeh, A. A., et al., 2000) Distinct types of diffuse large B-cell lymphoma identified by gene expression profiling. Nature, Vol. 403, Issue 3, February, 2000.

(Brown, M. P. S., et al. 2000) Knowledge-based analysis of microarray gene expression data by using support vector machines. PNAS, Vol. 97, no. 1: 262–267, January, 2000.

(Perou, C. M., et al., 1999) Distinctive gene expression patterns in human mammar epithelial cells and breast cancers, Proc. Natl. Acad. Sci. USA, Vol. 96, pp. 9212–9217, August 1999, Genetics (Ghina, C., et al., 1998) Altered Expression of Heterogeneous Nuclear Ribonucleoproteins and SR Factors in Human, Cancer Research, 58, 5818–5824, Dec. 15, 1998.

(Duda, R. O., et al., 1973) Pattern classification and scene analysis. Wiley. 1973.

(Golub, et al., 1999) Molecular Classification of Cancer: Class Discovery and Class Prediction by Gene Expression Monitoring. Science Vol 286, Oct 1999.

(Guyon, I., et al., 1992) Structural risk minimization for character recognition. Advances in Neural Information Processing Systems 4 (NIPS 91), pages 471–479, San Mateo Calif., Morgan Kaufmann. 1992.

(Guyon, I., et al., 1996) Discovering informative patterns and data cleaning. Advances in Knowledge Discovery and Data Mining, pages 181–203. MIT Press. 1996.

(Vapnik, V. N., 1998) Statistical Learning Theory. Wiley Interscience. 1998.

(Guyon, I. et al., 1998) What size test set gives good error rate estimates? PAMI, 20 (1), pages 52–64, IEEE. 1998.

(Boser, B. et al., 1992) An training algorithm for optimal margin classifiers. In Fifth Annual Workshop on Computational Learning Theory, pages 144–152, Pittsburgh, ACM. 1992.

(Cristianini, N., et al., 1999) An introduction to support vector machines. Cambridge University Press. 1999.

(Kearns, M., et al. 1997). An experimental and theoretical comparison of model selection methods. Machine Learning 27: 7–50. 1997.

(Shürmann, J., 1996) Pattern Classification. Wiley Interscience. 1996.

(Mozer, T., et al. 1999) Angiostatin binds ATP synthase on the surface of human endothelial cells, PNAS, Vol. 96, Issue 6, 2811–2816, Mar. 16, 1999. Cell Biology.

(Oliveira, E. C., 1999) Chronic Trypanosoma cruzi infection associated to colon cancer. An experimental study in rats. Resumo di Tese. Revista da Sociedade Brasileira de Medicina Tropical 32(1):81–82, January–February, 1999.

(Karakiulakis, G., 1997) Increased Type IV Collagen-Degrading Activity in Metastases Originating from Primary Tumors of the Human Colon, Invasion and Metastasis, Vol. 17, No. 3, 158–168, 1997.

(Aronson, 1999) Remodeling the Mammary Gland at the Termination of Breast Feeding: Role of a New Regulator Protein BRP39, The Beat, University of South Alabama College of Medicine, July, 1999.

(Macalma, T., et al. 1996) Molecular characterization of human zyxin. Journal of Biological Chemistry. Vol. 271, Issue 49, 31470–31478, December, 1996.

(Harlan, D. M., et al. 1991) The human myristoylated alanine-rich C kinase substrate (MARCKS) gene (MACS). Analysis of its gene product, promoter, and chromosomal localization. Journal of Biological Chemistry, Vol. 266, Issue 22, 14399–14405, August, 1991.

(Thorsteinsdottir, U., et al. 1999) The oncoprotein E2A-Pbx1a collaborates with Hoxa9 to acutely transform primary bone marrow cells. Molecular Cell Biology, Vol. 19, Issue 9, 6355–66, September, 1999.

(Osaka, M., et al. 1999) MSF (MLL septin-like fusion), a fusion partner gene of MLL, in a therapy-related acute myeloid leukemia with a t(11;17)(q23;q25). Proc Natl Acad Sci USA. Vol. 96, Issue 11, 6428–33, May, 1999.

(Walsh, J. H., 1999) Epidemiologic Evidence Underscores Role for Folate as Foiler of Colon Cancer. Gastroenterology News. Gastroenterology. 116:3–4, 1999.

(Aerts, H., 1996) Chitotriosidase—New Biochemical Marker. Gauchers News, March, 1996.

(Fodor, S. A., 1997) Massively Parallel Genomics. Science. 277:393–395, 1997.

(Schölkopf, B., et al. 1999) Estimating the Support of a High-Dimensional Distribution, in proceeding of NIPS 1999.

What is claimed is:

1. A method for enhancing knowledge discovered from biological data using a learning machine comprising the steps of:

a) pre-processing a training data set derived from biological data to expand each of a plurality of training data points;

training the learning machine using the pre-processed training data set;

pre-processing a test data set derived from biological data to expand each of a plurality of test data points;

testing the trained learning machine using the pre-processed test data set to generate a test output; and in response to receiving the test output of the trained learning machine, post-processing the test output to determine if the knowledge discovered from the pre-processed test data set is desirable.

2. The method of claim 1, wherein pre-processing the training data set to expand each of the plurality of training data points comprises adding dimensionality to each of the plurality of training data points.

3. The method of claim 2, wherein each training data point comprises a vector having one or more original coordinates; and wherein adding dimensionality to each training data point comprises adding one or more new coordinates to the vector.

4. The method of claim 3, wherein the new coordinate added to the vector is derived by applying a transformation to one of the original coordinates.

5. The method of claim 4, wherein the transformation is based on expert knowledge.

6. The method of claim 4, wherein the transformation is computationally derived.

7. The method of claim 4, wherein the training data set comprises a continuous variable; and wherein the transformation comprises optimally categorizing the continuous variable of training data set.

8. The method of claim 1, wherein post-processing the test output comprises interpreting the test output into a format that may be compared with the plurality of test data points.

9. The method of claim 1, wherein the knowledge to be discovered from the data relates to a regression or density estimation; and wherein post-processing the test output comprises optimally categorizing the test output to derive cutoff points in the continuous variable.

10. The method of claim 1, wherein the knowledge to be discovered from the data relates to a regression or density estimation;

wherein the training output comprises a continuous variable; and wherein the method further comprises the steps of:

in response to training the learning machine, receiving a training output from the learning machine, and post-processing the training output by optimally categorizing the test output to derive cutoff points in the continuous variable.

11. The method of claim 1, wherein the knowledge discovered from biological data comprises diagnosis or prognosis of a disease state.

12. The method of claim 1, wherein the knowledge discovered from biological data comprises efficacy of treatment of a disease state.

13. A method for enhancing knowledge discovered from biological data using a support vector machine comprising the steps of:

pre-processing a training data set derived from biological data to add meaning to each of a plurality of training data points;

training the support vector machine using the pre-processed training data set;

pre-processing a test data set derived from biological data to expand each of a plurality of test data points;

testing the trained support vector machine using the pre-processed test data set to generate a test output; and in response to receiving the test output of the trained support vector machine, post-processing the test output to determine if the test output is an optimal solution.

14. The method of claim 13, wherein each training data point comprises a vector having one or more coordinates; and wherein pre-processing the training data set to add meaning to each training data point comprises:

determining that the training data point is dirty; and in response to determining that the training data point is dirty, cleaning the training data point.

15. The method of claim 14, wherein cleaning the training data point comprises deleting, repairing or replacing the data point.

16. The method of claim 13, wherein each training data point comprises a vector having one or more original coordinates; and wherein pre-processing the training data set to add meaning to each training data point comprises adding dimensionality to each training data point by adding one or more new coordinates to the vector.

17. The method of claim 16, wherein the one or more new coordinates added to the vector are derived by applying a transformation to one or more of the original coordinates.

18. The method of claim 17, wherein the transformation is based on expert knowledge.

19. The method of claim 17, wherein the transformation is computationally derived.

20. The method of claim 17, wherein the training data set comprises a continuous variable; and wherein the transformation comprises optimally categorizing the continuous variable of the training data set.

21. The method of claim 13, wherein post-processing the test output comprises interpreting the test output into a format that may be compared with the test data set.

22. The method of claim 13, wherein the knowledge to be discovered from the data relates to a regression or density estimation;

wherein a training output comprises a continuous variable; and wherein the method further comprises the step of post-processing the training output by optimally categorizing the training output to derive cutoff points in the continuous variable.

23. The method of claim 13, further comprising the steps of:

selecting a kernel for the support vector machine prior to training the support vector machine;

in response to post-processing the test output, determining that the test output is not the optimal solution;

adjusting the selection of the kernel; and in response to adjusting the selection of the kernel, retraining and retesting the support vector machine.

24. The method of claim 23, wherein the selection of a kernel is based on prior performance or historical data and is dependent on the nature of the knowledge to be discovered from the data or the nature of the data.

25. The method of claim 13, further comprising the steps of:

in response to post-processing the test output, determining that the test output is the optimal solution;

collecting a live data set;

pre-processing the live data set to expand each of a plurality of live data points;

inputting the pre-processed live data set to the support vector machine for processing; and receiving the live output of the trained support vector machine.

26. The method of claim 25, further comprising the step post-processing the live output by interpreting the live output into a computationally derived alphanumerical classifier.

27. The method of claim 13, wherein the knowledge discovered from biological data comprises diagnosis or prognosis of a disease state.

28. The method of claim 13, wherein the knowledge discovered from biological data comprises efficacy of treatment of a disease state.

29. A system for enhancing knowledge discovered from biological data using a support vector machine comprising:

a storage device for storing a training data set and a test data set;

a processor for executing a support vector machine;

the processor further operable for:

collecting the training data set from the database, pre-processing the training data set to add meaning to each of a plurality of training data points, training the support vector machine using the pre-processed training data set;

in response to training the support vector machine, collecting the test data set from the database, pre-processing the test data set to expand each of a plurality of test data points, testing the trained support vector machine using the pre-processed test data set to generate a test output, and in response to receiving the test output of the trained support vector machine, post-processing the test output to determine if the test output is an optimal solution.

30. The system of claim 29, further comprising a communications device for receiving the test data set and the training data set from a remote source; and wherein the processor is further operable to store the training data set in the storage device prior to collection and pre-processing of the training data set and to store the test data set in the storage device prior to collection and pre-processing of the test data set.

31. The system of claim 29, further comprising a display device for displaying the post-processed test data.

32. The system of claim 29, wherein each training data point comprises a vector having one or more original coordinates; and wherein pre-processing the training data set to add meaning to each training data point comprises adding dimensionality to each training data point by adding one or more new coordinates to the vector.

33. The system of claim 32, wherein the one or more new coordinates added to the vector are derived by applying a transformation to one or more of the original coordinates.

34. The system of claim 33, wherein the transformation is based on expert knowledge.

35. The system of claim 33, wherein the transformation is computationally derived.

36. The system of claim 33, wherein the training data set comprises a continuous variable; and wherein the transformation comprises optimally categorizing the continuous variable of the training data set.

37. The system of claim 29, wherein the test output comprises a continuous variable; and wherein post-processing the test output comprises optimally categorizing the continuous variable of the test data set.

38. The system of claim 29, wherein the knowledge to be discovered from the data relates to a regression or density estimation;

wherein a training output comprises a continuous variable; and wherein the processor is further operable for post-processing the training output by optimally categorizing the continuous variable of the training output.

39. The system of claim 38, wherein optimally categorizing the training output comprises determining optimal cutoff points in the continuous variable based on entropy calculations.

40. The system of claim 29, wherein the processor is further operable for:

selecting a kernel for the support vector machine prior to training the support vector machine;

in response to post-processing the test output, determining that the test output is not the optimal solution;

adjusting the selection of the kernel; and in response to adjusting the selection of the kernel, retraining and retesting the support vector machine.

41. The system of claim 40, wherein the selection of a kernel is based on prior performance or historical data and is dependant on the nature of the knowledge to be discovered from the data or the nature of the data.

42. The system of claim 29, wherein a live data set is stored in the storage device; and wherein the processor is further operable for:

in response to post-processing the test output, determining that the test output is the optimal solution, collecting the live data set from the storage device;

pre-processing the live data set to expand each of a plurality of live data points;

inputting the pre-processed live data set to the support vector machine for processing to generate live output; and receiving the live output of the trained support vector machine.

43. The system of claim 42, wherein the processor is further operable for post-processing the live output by interpreting the live output into a computationally derived alphanumerical classifier.

44. The system of claim 43, wherein the communications device is further operable to send the alphanumerical classifier to the remote source or another remote source.

45. The system of claim 29, wherein the knowledge discovered from biological data comprises diagnosis or prognosis of a disease state.

46. The system of claim 29, wherein the knowledge discovered from biological data comprises efficacy of treatment of a disease state.

47. A method for diagnosing disease, comprising, using a learning machine comprising, a) pre-processing a training data set derived from biological data to expand each of a plurality of training data points;

training the learning machine using the pre-processed training data set;

pre-processing a test data set derived from biological data to expand each of a plurality of test data points;

testing the trained learning machine using the pre-processed test data set to generate a test output; and in response to receiving the test output of the trained learning machine, post-processing the test output to determine if the knowledge discovered from the pre-processed test data set is desirable.

48. The method of claim 47, wherein the disease is cancer.

49. The method of claim 48, wherein the cancer is colon cancer.

50. The method of claim 48, wherein the cancer is breast cancer.

51. The method of claim 47, wherein the knowledge discovered from the test data set comprises genes associated with the disease.

* * * * *